US011273172B2

(12) United States Patent
Prabhakar et al.

(10) Patent No.: US 11,273,172 B2
(45) Date of Patent: Mar. 15, 2022

(54) SYNERGISTIC COMBINATION OF OLIGONUCLEOTIDES AND CHEMOTHERAPEUTIC FOR TREATING CANCER

(71) Applicant: THE BOARD OF TRUSTEES OF THE UNIVERSITY OF ILLINOIS, Urbana, IL (US)

(72) Inventors: Bellur Prabhakar, Oak Brook, IL (US); Sidney Hopps, River Forest, IL (US); Aditi Mathur, Buffalo Grove, IL (US); Fei Yue, North Riverside, IL (US); Shikha Saini, Chicago, IL (US)

(73) Assignees: The Board of Trustees of the University of Illinois, Urbana, IL (US); Jivana Biotechnology Inc., Miami, FL (US)

( * ) Notice: Subject to any disclaimer, the term of this patent is extended or adjusted under 35 U.S.C. 154(b) by 43 days.

(21) Appl. No.: 16/662,588

(22) Filed: Oct. 24, 2019

(65) Prior Publication Data

US 2020/0038426 A1 Feb. 6, 2020

Related U.S. Application Data

(63) Continuation-in-part of application No. PCT/US2018/026173, filed on Apr. 5, 2018, and a continuation-in-part of application No. PCT/US2018/026177, filed on Apr. 5, 2018, and a continuation-in-part of application No. PCT/US2018/026181, filed on Apr. 5, 2018, and a continuation-in-part of application No. PCT/US2018/026182, filed on Apr. 5, 2018, and a continuation-in-part of application No. PCT/US2018/026231, filed on Apr. 5, 2018.

(60) Provisional application No. 62/489,056, filed on Apr. 24, 2017, provisional application No. 62/489,061, filed on Apr. 24, 2017, provisional application No. 62/489,097, filed on Apr. 24, 2017, provisional application No. 62/489,069, filed on Apr. 24, 2017, provisional application No. 62/489,050, filed on Apr. 24, 2017.

(51) Int. Cl.

| | |
|---|---|
| ***C07H 21/02*** | (2006.01) |
| ***C07H 21/04*** | (2006.01) |
| ***A61K 31/7105*** | (2006.01) |
| ***C12N 15/113*** | (2010.01) |
| ***A61P 35/00*** | (2006.01) |
| ***A61K 9/127*** | (2006.01) |
| ***C12N 15/63*** | (2006.01) |
| ***A61P 31/00*** | (2006.01) |
| *A61K 45/06* | (2006.01) |

(52) U.S. Cl.

CPC .......... *A61K 31/7105* (2013.01); *A61K 9/127* (2013.01); *A61P 31/00* (2018.01); *A61P 35/00* (2018.01); *C12N 15/113* (2013.01); *C12N 15/63* (2013.01); *A61K 45/06* (2013.01); *C12N 2310/11* (2013.01); *C12N 2310/14* (2013.01); *C12N 2310/531* (2013.01); *C12N 2320/31* (2013.01)

(58) Field of Classification Search

CPC ........................ C12N 15/113; C12N 2310/531

See application file for complete search history.

(56) References Cited

U.S. PATENT DOCUMENTS

| | | | |
|---|---|---|---|
| 7,910,723 | B2 | 3/2011 | Prabhakar et al. |
| 8,722,637 | B2 | 5/2014 | Prabhakar |
| 2004/0096436 | A1 | 5/2004 | Carson et al. |
| 2009/0075929 | A1 | 3/2009 | Prabhakar et al. |
| 2011/0117627 | A1 | 5/2011 | Prabhakar et al. |
| 2012/0135408 | A1 | 5/2012 | Epstein et al. |

OTHER PUBLICATIONS

Mulherkar et al. (Oncogene, 2006, 25, 6252-6261).*
Siegel et al. (Hepatology, 52, 1, 2010, 360-369).*
Shen et al. (Mol. Pharmaceutics, 2014, 11, 3342-3351).*
Adeeb et al. (2001) "Contrasting Effects of IG20 and Its Splice Isoforms, MADD Contrasting Effects of IG20 and Its Splice Isoforms, MADD and DENN-SV, on Tumor Necrosis Factor α-induced Apoptosis and Activation of Caspase-8 and -3," Journal of Biological Chemistry 276(50):47202-47211.
International Preliminary Report on Patentability in PCT/US2018/026231 dated Oct. 29, 2019.
International Search Report and Written Opinion in PCT/US2018/026231 dated Aug. 21, 2018.
International Preliminary Report on Patentability in PCT/US2018/026182 dated Oct. 29, 2019.
International Search Report and Written Opinion in PCT/US2018/026182 dated Aug. 10, 2018.
International Preliminary Report on Patentability in PCT/US2018/026181 dated Oct. 29, 2019.

(Continued)

*Primary Examiner* — Amy H Bowman
(74) *Attorney, Agent, or Firm* — Licata & Tyrrell P.C.

(57) ABSTRACT

Compositions and methods for treating cancers are provided which comprise administering a combination of antineoplastic agents, wherein the combination comprises protein kinase inhibitor, anthracycline, nucleoside analog, apoptosis-inducing molecular therapeutic or alkylating agent chemotherapeutics and one or more nucleic acid molecules capable of down-regulating expression of at least one splice variant of the IG20 gene, and wherein not all splice variants of the IG20 gene are down-regulated. Preferably, the splice variant of the IG20 gene is a MADD splice variant and the nucleic acid molecules are siRNA, shRNA and antisense oligonucleotides which comprise a nucleic acid sequence complementary to a nucleic acid sequence of exon 13L of the MADD splice variant or to an mRNA transcript of exon 13L of the MADD splice variant.

18 Claims, 1 Drawing Sheet

Specification includes a Sequence Listing.

(56) References Cited

OTHER PUBLICATIONS

International Search Report and Written Opinion in PCT/US2018/026181 dated Aug. 24, 2018.

International Preliminary Report on Patentability in PCT/US2018/026177 dated Oct. 29, 2019.

International Search Report and Written Opinion in PCT/US2018/026177 dated Jul. 23, 2018.

International Preliminary Report on Patentability in PCT/US2018/026173 dated Oct. 29, 2019.

International Search Report and Written Opinion in PCT/US2018/026173 dated Oct. 31, 2018.

Efimova et al. (2004) "IG20, in contrast to DENN-SV, (MADD splice variants) suppresses tumor cell survival, and enhances their susceptibility to apoptosis and cancer drugs," Oncogene 23(5):1076-1087.

Kurada et al. (2009) "MADD, a Splice Variant of IG20, Is Indispensable for MAPK Activation and Protection against Apoptosis upon Tumor Necrosis Factor-α Treatment," Journal of Biological Chemistry 284(20):13533-13541.

Lim et al. (2002) "Induction of marked apoptosis in mammalian cancer cell lines by antisense DNA treatment to abolish expression of DENN (differentially expressed in normal and neoplastic cells)," Molecular Carcinogenesis 35:110-126.

Lim et al. (2004) "Antisense abrogation of DENN expression induces apoptosis of leukemia cells in vitro, causes tumor regression in vivo and alters the transcription of genes involved in apoptosis and the cell cycle," International Journal of Cancer 109(1):24-37.

Turner et al. (2013) "MADD Knock-Down Enhances Doxorubicin and TRAIL Induced Apoptosis in Breast Cancer Cells," PLoS One 8(2): e56817.

Zheng et al. (2014) "Effects of doxorubicin and gemcitabine on the induction of apoptosis in breast cancer cells," 32(6):2719-25.

* cited by examiner

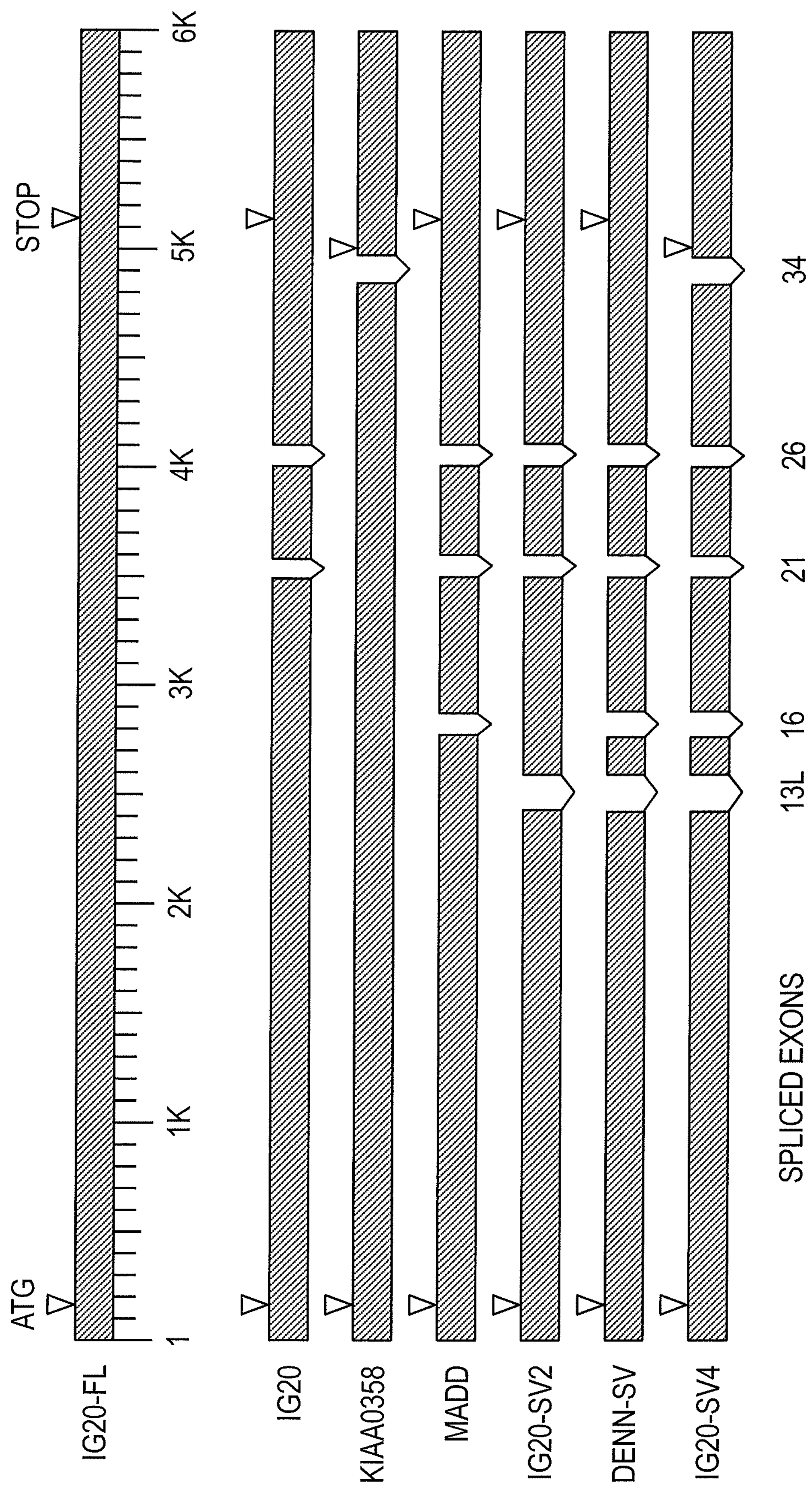
IG20-FL
ATG
STOP
1
1K
2K
3K
4K
5K
6K
IG20
KIAA0358
MADD
IG20-SV2
DENN-SV
IG20-SV4
SPLICED EXONS
13L
16
21
26
34

SYNERGISTIC COMBINATION OF OLIGONUCLEOTIDES AND CHEMOTHERAPEUTIC FOR TREATING CANCER

INTRODUCTION

This application is a continuation-in-part application of PCT International Application No. PCT/US2018/026173, filed Apr. 5, 2018, which claims the benefit of priority from U.S. Provisional Application Ser. No. 62/489,056, filed Apr. 24, 2017; PCT International Application No. PCT/US2018/026177, filed Apr. 5, 2018, which claims the benefit of priority from U.S. Provisional Application Ser. No. 62/489,061, filed Apr. 24, 2017; PCT International Application No. PCT/US2018/026181, filed Apr. 5, 2018, which claims the benefit of priority from U.S. Provisional Application Ser. No. 62/489,097, filed Apr. 24, 2017; PCT International Application No. PCT/US2018/026182, filed Apr. 5, 2018, which claims the benefit of priority from U.S. Provisional Application Ser. No. 62/489,069, filed Apr. 24, 2017; and PCT International Application No. PCT/US2018/026231, filed Apr. 5, 2018, which claims the benefit of priority from U.S. Provisional Application Ser. No. 62/489,050, filed Apr. 24, 2017, the contents of which are incorporated herein by reference in their entireties.

BACKGROUND

The Insulinoma-Glucagonoma (IG20) gene plays an important role in cancer cell proliferation, apoptosis and survival (Chow & Lee (1996) *DNA Seq.* 6:263-273; Chow, et al. (1998) *Genome* 41:543-552; Schievella, et al. (1997) *J. Biol. Chem.* 272:12069-12075; Brinkman, et al. (1999) *J. Biol. Chem.* 274:30882-30886; Murakami-Mori, et al. (1999) *J. Immunol.* 162:3672-3679; Telliez, et al. (2000) *Biochem. Biophys. Acta* 1478:280-288; Al-Zoubi, et al. (2001) *J. Biol. Chem.* 276:47202-47211; Lim & Chow (2002) *Mol. Carcinog.* 35:110-126; Efimova, et al. (2004) *Oncogene* 23:1076-1087; Efimova, et al. (2003). *Cancer Res.* 63:8768-8776; Lim, et al. (2004) *Int. J. Cancer* 109:24-37; Ramaswamy, et al. (2004) *Oncogene* 23:6083-6094). Additionally, it plays an important role in neurotransmission (Zhang, et al. (1998) *Proc. Natl. Acad. Sci. USA* 95:2586-2591; Tanaka, et al. (2001) *Mol. Biol. Cell* 12:1421-1430; Yamaguchi, et al. (2002). *Proc. Natl. Acad. Sci. USA* 99:14536-14541), neurodegeneration (Del Villar & Miller (2004) *Proc. Natl. Acad. Sci. USA* 101:4210-4215) and guanine nucleotide exchange (Wada, et al. (1997) *J. Biol. Chem.* 272:3875-3878; Brown & Howe (1998) *Curr. Biol.* 8:R191; Iwasaki & Toyonaga (2000) *EMBO J.* 19:4806-4816; Levivier, et al. (2001) *Biochem. Biophys. Res. Commun.* 287:688-695). These divergent functions are most likely mediated through alternative splicing of the IG20 gene to provide splice variants and protein diversity (Chow, et al. (1998) *Genome* 41:543-552; Al-Zoubi, et al. (2001) *J. Biol. Chem.* 276:47202-47211; Efimova, et al. (2004) *Oncogene* 23:1076-1087). Down-regulation of all endogenous IG20 splice variants, using anti-sense oligonucleotides, has been shown to result in spontaneous apoptosis of cancer cells in vitro and in vivo, but not in normal cells (Lim & Chow (2002) *Mol. Carcinog.* 35:110-126; Lim, et al. (2004) *Int. J. Cancer* 109:24-37).

U.S. Pat. No. 8,722,637 describes "IG20 and IG20-[SV2], and the previously reported KIAA0358, MADD, and DENN-SV are splice variants of the IG20 gene, which is localized to chromosome 11p11 and consists of 36 exons. Differences among the above variants are due to alternative splicing of exons 13L, 16, 21, 26 and 34." The IG20, MADD, SV2 and DENN-SV isoforms may be considered to be described by Adeeb, et al. (2001) *J. Biol. Chem.* 276(50):47202-47211). Subsequent to the disclosure in Al-Zoubi, et al., longer isoforms were identified, including KIAA0358. Consequently, the IG20 splice variant identified by Al-Zoubi, et al. as IG20 became known as IG20pa because, as U.S. Pat. No. 8,722,637 explains, the IG20 expression protein is a pro-apoptotic signaling molecule which is distinct from the IG20-FL or full-length variant (col. 5, lns. 43-45).

It has further been suggested that all seven variants of IG20 identified to date arise from alternative splicing of exons 13L, 16, 21, 26 and 34. The full-length cDNA of IG20 (IG20-FL) (accession number AF440100) is 5995 base pairs (bps) long, consists of all 36 exons and represents the longest variant (Efimova, et al. (2004) *Oncogene* 23:1076-1087). These splice variants may be graphically represented as in FIG. 1. Splicing of exon 34 alone generates KIAA0358 (accession number AB002356) that consists of 5942 bps. Splicing of exons 21 and 26, and splicing of exons 16, 21 and 26 generate 5878 bps long IG20 accession number AF440101) and 6002 bps long MADD (accession number U77352), respectively. MADD is also known as DENN (accession number U44953) that is 5844 bps long. Splicing of exons 13L, 21 and 26, and 13L, 16, 21 and 26 generate 5749 bps long IG20-SV2 (accession number AF440102) and 5689 bps long IG20-SV3 (accession number AF440103) (earlier referred to as DENN-SV). Finally, splicing of all five exons (13L, 16, 21, 26 and 34) generates IG20-SV4 (accession number AF440434), which is the shortest variant and consists of 5619 bps.

At the time of filing of U.S. Pat. No. 8,722,637, it was determined that IG20pa, MADD, IG20-SV2 and DENN-SV are expressed in human tissues and, to a greater degree, in tumors (U.S. Pat. No. 8,722,637 at col. 5, lns. 1-2). Overexpression of DENN-SV was associated with enhanced cell replication and resistance to apoptosis induced by chemotherapy (U.S. Pat. No. 8,722,637 at col. 5, lns. 4-6). Overexpression of IG20pa was shown to override endogenous DENN-SV function, resulting in apoptosis (U.S. Pat. No. 8,722,637 at col. 5, lns. 16-17).

Through the experimentation performed in U.S. Pat. No. 8,722,637, it was determined that, "[b]ecause DENN-SV lacks both exons 13L and 16, MADD lacks exon 16 and IG20-SV2 lacks exon 13L, these results demonstrated that expression of both exons 13L and 16, as seen in IG20[pa], is required for anti-proliferative and pro-apoptotic properties, whereas deletion of both exons, as seen in DENN-SV, is required for pro-proliferative and anti-apoptotic properties." U.S. Pat. No. 8,722,637 at col. 17, lns. 38-44. Ultimately, U.S. Pat. No. 8,722,637 concludes that "[t]here is clear evidence to suggest that IG20[pa] and DENN-SV have contrasting effects on apoptosis and cell proliferation." U.S. Pat. No. 8,722,637 at col. 18, lns. 37-39. It is further concluded that "IG20 [pa] is a pro-apoptotic protein that can interact with DR4 and DR5 and significantly enhance TRAIL induced apoptosis by facilitating DISC formation with increased recruitment of FADD and caspase-8." U.S. Pat. No. 8,722,637 at col. 23, lns. 1-4. Finally, it was concluded that "IG20[pa] can render cells more susceptible to apoptosis and suppress cell growth. This raises the possibility of using IG20[pa] to render cells that are otherwise resistant to become more susceptible to various modalities of cancer therapy." U.S. Pat. No. 8,722,637 at col. 27, lns. 20-24.

As a result of the understanding achieved through over-expression of IG20 splice variants, it was concluded that "[c]ells transfected with IG20[pa] and DENN-SV were most susceptible and resistant to TNFα-induced apoptosis respectively, whereas cells transfected with MADD or IG20-SV2 did not show significant differences relative to cells transfected with a control plasmid. Because DENN-SV lacks both exons 13L and 16, MADD lacks exon 16 and IG20-SV2 lacks exon 13L, these results demonstrated that expression of both exons 13L and 16, as seen in IG20[pa], is required for anti-proliferative and pro-apoptotic properties, whereas deletion of both exons, as seen in DENN-SV, is required for pro-proliferative and anti-apoptotic properties." U.S. Pat. No. 8,722,637 at col. 17, lns. 34-44.

Therefore, prior to U.S. Pat. No. 8,722,637, the full complexity of IG20 splice variant expression, selective expression of different isoforms in different tissues and the unique functional attributes of each of the splice variants were not appreciated. Based on the experimentation into the over-expression of IG20 splice variants as disclosed in U.S. Pat. No. 8,722,637, the impact of indiscriminate knockdown of splice variants, not taking into account variant splicing at introns 16 (MADD), 13L and 16 (DENN-SV), 21 and 26 (MADD, DENN-SV, IG20pa) and 34 (KIAA0358, IG20-SV4), could prove vital for normal neuronal function and survival of the animal (i.e., KIAA0358), cancer cell survival (i.e., MADD) and proliferation (i.e., DENN-SV). Therefore, the patent provides a functional characterization of IG20 isoforms and explains the complexity in devising strategies which may selectively modulate various isoform expression while avoiding unintended lethal consequences.

The IG20pa splice variant is pro-apoptotic, anti-proliferative, and renders cells more susceptible to induced cell death (i.e., is a tumor suppressor). IG20pa, or a fragment thereof, may be overexpressed to control cell proliferation, cell cycle, and to render cells more susceptible to chemotherapy, radiation therapy or death receptor mediated cell death.

DENN-SV expression can be down-modulated to reduce cell proliferation, affect cell cycle and increase susceptibility to treatment with chemotherapy, radiation therapy and death receptor mediated cell death.

Differential expression of IG20pa and DENN-SV splice variants renders cells either more susceptible or resistant to induced cell death respectively, and the pro-apoptotic property of IG20pa variant may be exploited to render tumor cells that are otherwise chemotherapeutic resistant to become susceptible to killing by tumor necrosis factor-related apoptosis-inducing ligand (TRAIL) and/or chemotherapeutic agents.

When IG20pa was over-expressed in cells, the cells showed significantly reduced proliferation and were much more susceptible to spontaneous TNFα- and TRAIL-induced apoptosis. Thus, the pro-apoptotic property of the IG20pa splice variant may be exploited to render tumor cells which are otherwise resistant to become susceptible to killing by TRAIL and/or chemotherapeutic agents.

Down-modulation of expression of IG20 splice variants with siRNA was evaluated using siRNA targeting the mid-region of the IG20 mRNA, specifically exon 15, having the sequence (5'-GTACCAGCTTCAGTCTTTC-3'; SEQ ID NO:14) and siRNA targeting the Death Domain (DD) region of IG20 mRNA. Both the mid-region and the DD region are present in all IG20 splice variants.

Treatment of cells with siRNA against the mid-region of IG20 mRNA, but not against the death domain (DD) of IG20 mRNA suppresses the levels of DENN-SV (completely abrogates). Cells treated with siRNA against the mid-region, i.e., exon 15, of IG20 mRNA undergo spontaneous apoptosis. Moreover, the cells that fail to undergo spontaneous apoptosis after siRNA treatment against the mid-region, i.e., exon 15, of IG20 mRNA are more susceptible to TNF-α induced apoptosis.

It may be concluded that, to decrease cell replication, selection of siRNA to down-modulate DENN-SV expression, specifically, without affecting expression of IG20 splice variants which are necessary for normal cell function, in particular, neuronal function and survival (KIAA0358 and IG20-SV4 splice variants), is desired.

Moreover, contrasting prior art oligodeoxynucleotide sequences, which in many cases proved lethal, oligodeoxynucleotides which take into account the research of U.S. Pat. No. 8,722,637 may be optimized to bind to particular exons which are differentially expressed in different isoforms. Knockdown using such engineered oligodeoxynucleotides may knockdown only those isoforms in which that particular targeted exon is expressed, allowing for selective knockdown of intended isoforms and reducing unintended negative effects associated with knockdown of critical isoforms.

Map kinase Activating Death Domain (MADD) containing protein, a product of the MADD splice variant of the IG20 gene, is essential for cancer cell survival. MADD is expressed at much higher levels in cancer cells and tissues relative to their normal counterparts. MADD has been shown to bind to death receptor-4 (DR4) and death receptor-5 (DR5) and to confer resistance to TRAIL-induced apoptosis in thyroid, ovarian and cervical cancer cell lines (Mulherkar, et al. (2007) *J. Biol. Chem.* 282:11715-11721; Subramanian, et al. (2009) *J. Clin. Endocrinol. Metab.* 94:1467-1471; Prabhakar, et al. (2008) *Clin. Cancer. Res.* 14:347-351; Li, et al. (2011) *Am. J. Obstet. Gynecol.* 205: 362 e312-325).

Abrogation of MADD, but not the other IG20 splice variants, may render cancer cells more susceptible to spontaneous as well as TRAIL-induced apoptosis. Spontaneous as well as TRAIL-induced apoptosis in cells devoid of MADD may be inhibited by expression of CrmA or dominant-negative FADD, thereby suggesting that endogenous MADD may interfere with caspase-8 activation. Further, it has been found that MADD can directly interact with death receptors, but not with either caspase-8 or FADD, but nonetheless inhibits caspase-8 activation. MADD has been shown to interfere with recruitment of FADD to the cytoplasmic domain of death receptors (Mulherkar, et al. (2007) *J. Biol. Chem.* 282(16):11715-11721). This demonstrates the importance of MADD in the control of cancer cell survival/death and in conferring resistance to TRAIL-induced apoptosis.

The ERK (extracellular signal-related kinase) pathway is a drug target for cancer chemotherapy since, in approximately one-third of all human cancers, there is deregulation of the mammalian mitogen-activated protein kinase (MAPK) pathways leading to ERK activation. MAPKs are serine/threonine-specific protein kinases which respond to extracellular stimuli (mitogens) and regulate several important and critical cellular functions required for cell homeostasis like metabolism, cell cycle progression, expression of cytokines, motility and adherence. Hence MAPKs influence cell survival, proliferation, differentiation, development and apoptosis. Extracellular stimuli such as cytokines, growth factors and environmental stresses lead to the sequential activation of a signaling cascade composed of MAPKs.

When activated, ERK1/2 phosphorylates several nuclear and cytoplasmic substrates involved in a multitude of cellular processes, including transcriptional factors, signaling proteins, kinases and phosphatases, cytoskeletal proteins, apoptotic proteins and proteinases. Even though the ERK pathway may be activated by numerous extracellular signals, the pathways whereby cytokines and growth factors activate ERK signaling are of particular relevance to cancer. For example, TNF-α, a cytokine rich in tumor stroma binds to TNF receptor 1 (TNFR1) which is present on cancer cells and potently activates ERK MAPKs. In the absence of MADD this pro-survival signaling pathway may be converted into an apoptotic signaling pathway leading to cancer cell death (Kurada, et al. (2009) *J. Biol. Chem.* 284:13533-13541).

An extrinsic cell death inducing signaling pathway may be initiated upon death ligand (e.g., TRAIL) binding to its cognate death receptors. The death receptors undergo trimerization and recruit FADD resulting in subsequent caspase-8 activation followed by executioner caspase-3 activation leading to apoptosis. TRAIL normally binds to DR4 and DR5 on cancer cells resulting in death receptor (DR) oligomerization and subsequent recruitment of FADD and procaspase-8 to the DRs (Bodmer, et al. (2000) *Nat. Cell Biol.* 2:241-243; Sprick, et al. (2000) *Immunity* 12:599-609; Kischkel, et al. (2000) *Immunity* 12:611-620). Procaspase-8 then undergoes proximity induced cleavage and activation forming caspase-8 which then activates executioner caspase-3 which causes apoptotic cell death. However, in cancer cells where MADD is over-expressed, MADD binds to DR4 and DR5 and prevents FADD recruitment to the DRs. Upon MADD down-regulation, FADD is more readily recruited to the DRs, resulting in enhanced apoptosis (Mulherkar, et al. (2007) *J. Biol. Chem.* 282:11715-11721; Mulherkar, et al. (2006) *Oncogene* 25:6252-6261).

TRAIL is unique in that it generally does not adversely affect normal cells or tissues (Keane, et al. (1999) *Cancer Res.* 59:734-741). However, development of chemotherapy and TRAIL resistance due to the interference of different anti-apoptotic proteins remains a major challenge. MADD is one such anti-apoptotic protein demonstrating the utility of MADD down-regulation in rendering cancer cells susceptible to cell death (Mulherkar, et al. (2006) *Oncogene* 25:6252-6261).

MADD may have a dual function in regulating apoptosis depending on its phosphorylation by Akt. The tumor suppressor PTEN (phosphatase and tensin homolog deleted on chromosome 10) is a lipid phosphatase that negatively regulates the phosphatidylinositol 3-kinase (PI3K)-Akt signaling pathway. MADD can act as a pro-apoptotic factor to initiate apoptosis when its phosphorylation is attenuated by PTEN (Jayarama, et al. (2014) *J. Cell. Biochem.* 115(2):261-270). TRAIL induces an up-regulation of PTEN with a concomitant reduction in MADD phosphorylation. Down-regulation of PTEN interferes with TRAIL-induced reduction in pMADD levels. Non-phosphorylated MADD translocates from the plasma membrane to cytoplasm where it binds to 14-3-3 protein and displaces 14-3-3 associated Bax, which Bax translocates to mitochondria resulting in cytochrome-c release. Taken together, one may conclude that PTEN can convey the death signal by preventing MADD phosphorylation by Akt.

The extrinsic apoptotic pathway may be abrogated by phosphorylated MADD. Endogenous MADD is phosphorylated at three highly conserved sites by Akt, and only the phosphorylated MADD can directly interact with the TRAIL receptor DR4 thereby preventing FADD recruitment. However, in cells susceptible to TRAIL treatment, TRAIL induces a reduction in MADD phosphorylation levels resulting in MADD dissociation from, and FADD association with DR4, which allows death-inducing signaling complex (DISC) formation leading to apoptosis (Li, et al. (2010) *J. Biol. Chem.* 285(29):22713-22722). Thus, the pro-survival function of MADD is dependent upon its phosphorylation by Akt. Because Akt is active in most cancer cells and phosphorylated MADD confers resistance to TRAIL-induced apoptosis, co-targeting the Akt-MADD axis is likely to increase efficacy of therapeutics which involve DR4/5 binding, including TRAIL-based therapies.

The intrinsic apoptotic pathway is initiated when a death signal induces the release of mitochondrial pro-apoptotic proteins such as cytochrome-c (Li, et al. (1997) *Cell* 91(4):479-489), mitochondrial apoptosis-inducing factor (Susin, et al. (1999) *Nature* 397(6718):441-446) and Smac/Diablo (Du, et al. (2000) *Cell* 102(1):33-42; Verhagen, et al. (2000) *Cell* 102(1):43-53). Cytochrome-c forms a complex with Apaf-1 and procaspase-9 resulting in the activation of caspase-9. Smac/Diablo can associate with Inhibitor of Apoptosis Proteins (IAPs) and counteract their caspase inhibitory effects. The intrinsic pathway is regulated by the Bcl-2 family members. For example, in response to pro-apoptotic stimuli, the cytosolic Bax and Bad translocate to mitochondria to permeabilize the outer mitochondrial membrane leading to cytochrome-c release into the cytosol. In contrast, Bcl-2 and Bcl-xL can associate with Bax and Bad thereby preventing them from inducing death (Antignani & Youle (2006) *Curr. Opin. Cell Biol.* 18(6):685-689). Interestingly, non-phosphorylated MADD translocates from the plasma membrane to cytoplasm where it binds to 14-3-3 and displaces 14-3-3 associated Bax, which translocates to mitochondria resulting in cytochrome-c release (Jayarama, et al. (2014) *J. Cell. Biochem.* 115(2):261-270).

The MADD cDNA sequence is available on the GenBank database under accession number NM_130470, and is represented herein by the nucleotide sequence of SEQ ID NO:11 and the polypeptide sequence of SEQ ID NO:12. Interfering RNAs which down-regulate MADD, including siRNA, shRNA and antisense oligonucleotides, are designed to target a nucleic acid sequence of exon 13L of a splice variant of the IG20 gene, and include any allelic variants and naturally occurring mutants of MADD, and polymorphisms which occur in the MADD splice variant which may be found in a particular segment of the population. In other words, sequences which are highly similar (e.g., about 95% at the amino acid level and about 75% at the nucleic acid level) and which represent naturally occurring variations in the MADD splice variant are within the scope of the disclosure, wherein the siRNA, shRNA and antisense oligonucleotides disclosed herein are capable of down-regulating the expression of such sequences. Exon 13L of the MADD splice variant may comprise a nucleotide sequence represented by nucleotides 2699 to 2827 of SEQ ID NO:11. Nucleic acid sequences which are about 80% or 90% or 95% similar at the nucleic acid level to the MADD sequence disclosed herein may also be down-regulated. Nucleic acid sequences which generate siRNA and shRNA which comprise nucleic acid sequences complementary to a nucleic acid sequence of exon 13L of the MADD splice variant of the IG20 gene and/or an mRNA transcript of exon 13L of the MADD splice variant, as well as nucleic acid variations which may occur within the exon 13L target region are within the scope of the instant disclosure. Moreover, antisense oligonucleotides which comprise nucleic acid sequences complementary to a nucleic acid sequence of exon 13L of the MADD splice variant of the IG20 gene and/or an mRNA transcript of exon 13L of the MADD splice variant, as well as nucleic acid variations which may occur within the exon 13L target region are within the scope of the instant disclosure Methods for specifically down-regulating the expression of a splice variant of an IG20 gene have been shown to include: (a) obtaining a nucleic acid molecule which is capable of down-regulating MADD expression, wherein the nucleic acid molecule or a transcription product thereof is capable of selectively binding to an mRNA molecule, the mRNA molecule which includes a nucleic acid sequence of a MADD splice variant of the IG20 gene; and (b) contacting a cell which expresses the MADD splice variant of the IG20 gene with the nucleic acid molecule, wherein the nucleic acid molecule down-regulates the expression of the MADD splice variant. In the cytoplasm, nucleic acids selected from siRNA, expressed shRNAs, and antisense oligonucleotides bind to target exon 13L mRNA and lead to degradation of the target 13L mRNA which down-regulates expression of the MADD splice variant.

Specifically, down-regulating MADD expression has been shown to be a substantial downregulation, for example, more than 90% or 95% reduction of the endogenous MADD expression. In fact, downregulation of, for example, at least 40%, at least 50%, at least 60%, at least 70%, and at least 80% of endogenous MADD expression is desirable.

Isolated siRNA, shRNA and antisense oligonucleotides which selectively down-regulate the expression of a splice variant of an IG20 gene, wherein the splice variant is MADD, are disclosed in U.S. Pat. No. 7,910,723. The patent describes the development of "splice variant specific" nucleic acid molecules that selectively down-regulate one or more of the splice variants of the IG20 gene and their relative importance in cancer cell survival. Not all cancer cells express all IG20 splice variants and some express only the MADD and the DENN splice variants. Using cells which expressed four known splice variants or only the MADD and DENN splice variants, and different nucleic acid molecules selected from shRNAs, siRNAs and antisense oligonucleotides, which specifically targeted exon 13L (to down-regulate IG20pa and MADD), exon 16 (to down-regulate IG20pa and IG20-SV2) and exon 15 (exon 15 is expressed in all splice variants of the IG20 gene and therefore it can down-regulate expression of all splice variants), the critical requirement for MADD for cancer cell survival has been demonstrated. Although siRNA, shRNA and antisense oligonucleotides targeting exon 16 could knockdown IG20pa, only the siRNA, shRNA and antisense oligonucleotides targeting exon 13L could cause cancer cell death. This indicated for the first time that specifically MADD might be critical for cancer cell survival. An additional line of evidence which shows MADD to be essential and sufficient for cancer cell survival is demonstrated in cells transfected with Mid-shRNA resistant IG20 splice variants in which the 3$^{rd}$ base of the triple codons was replaced in the Mid-shRNA targeted region of the cDNA constructs, which DNA substitutions will not alter the amino acid sequence but renders them resistant to Mid-shRNA). When the expression of all endogenous IG20 splice variants was down-regulated using Mid-shRNA, only cells expressing a MADD splice variant could prevent cell death, whereas the other splice variants could not prevent cell death. Using cancer cells that expressed only MADD and DENN-SV splice variants, it was shown that MADD could be selectively down-regulated using siRNA, shRNA or antisense oligonucleotides which target exon 13L and it was shown that MADD, alone, is sufficient and required for cancer cell survival (Mulherkar, et al. (2006) *Oncogene* 25:6252-61).

Thus, none of the earlier research revealed the full complexity of IG20 gene expression, the differential expression of the splice variants in different tissues, the unique functional attributes of each of the splice variants (i.e., cancer cell survival (MADD) and proliferation (DENN). Therefore, it is the discovery of various splice variants, their functional characterization and the ability to identify specific nucleic acid molecules which can selectively down-regulate expression of splice variants which allowed the inventors to develop cancer therapeutics without unintended potential negative consequences.

U.S. Pat. No. 7,910,723 describes nucleic acid molecules which target exon 13L of the IG20 gene and the use of encoded siRNA, shRNA and antisense oligonucleotides in down-regulating expression of MADD protein. The patent describes how the nucleic acid selection may be optimized to achieve effective down-regulation of MADD expression, including selecting for nucleic acid molecules which consist essentially of a nucleotide sequence CGGCGAATCTATGACAATC (SEQ ID NO:1), and transcribed products thereof, encoding nucleic acid molecules consisting essentially of a nucleotide sequence CGGCGAAUCUAUGACAAUC (SEQ ID NO:2). Species nucleic acid molecules representative of such strategy include siRNA, shRNA and antisense oligonucleotides, which comprise less than 50% GC nucleotide content, high AU nucleotide content toward the 3' end and no inverted repeats within the siRNA region, which oligonucleotides constitute an array of nucleic acid molecules which may span the exon 13L nucleotide sequence. These encoded nucleic acid molecules and encoded siRNA, shRNA and antisense oligonucleotides are demonstrated to be sufficient to down-regulate the expression of MADD splice variants. Natural variations of MADD including specific SNPs, allelic variants, or mutations which may appear in one or more of sub-groups of cancer types may be targeted by such nucleic acid molecules.

Methods for down-regulating expression of MADD are described to include: (a) obtaining a nucleic acid molecule which selectively down-regulates MADD expression, wherein the nucleic acid molecule is capable of selectively binding to an mRNA molecule of a MADD splice variant of the IG20 gene; and (b) contacting a cancer cell which expresses the MADD splice variant of the IG20 gene with the nucleic acid molecule, wherein the nucleic acid molecule down-regulates the expression of the MADD splice variant in the cancer cell.

Moreover, representative nucleic acid molecules which are shown to down-regulate the MADD splice variant of IG20, allelic variations thereof, polymorphisms thereof, and genetic mutations thereof, include siRNA, shRNA, and anti-sense nucleic acid molecules which may comprise a nucleotide sequence CGGCGAAUCUAUGACAAUC (SEQ ID NO:2). The siRNA may be in the form of a duplex with the cognate antisense nucleic acid, which cognate antisense nucleic acid is complementary to a target MADD exon 13L nucleotide sequence and/or mRNA transcripts of MADD exon 13L.

Down-regulation of specific splice variants of the IG20 gene is difficult because of the very short target sequences which are differentially expressed in different splice variants. U.S. Pat. No. 7,910,723 explains that, in an embodiment of the invention, down-regulation may be achieved through the use of specially designed short hairpin RNA molecules (shRNA). shRNA comprise complementary sense and antisense sequences of the target gene linked by a loop structure. A dsDNA may be cloned into an expression vector for transfection which may then be transcribed to form shRNA, which is cleaved into siRNA, which may inhibit gene expression through RNA interference (RNAi). In an embodiment, nucleic acids encoding such an shRNA, including the structure:

$X_{sense}$-hairpin loop-$X_{anti\text{-}sense}$, wherein X (encoding siRNA) includes or consists essentially of a nucleic acid having the sequence CGGCGAATCTATGACAATC (SEQ ID NO:1). The nucleic acid is transcribed to form shRNA and may be cleaved to form siRNA which may ultimately inhibit MADD expression. Thus, RNA molecules which are transcribed in vitro or in vivo, e.g., in a cancer cell or tumors to form shRNA and siRNA are also included.

An exemplary dsDNA nucleic acid sequence encoding an shRNA inhibiting MADD expression may be CGGCGAATCTATGACAATCTTCAAGAGAGATTGTCATAGATTCGCCG (SEQ ID NO:13), wherein the hairpin loop region between $X_{sense}$ and $X_{anti\text{-}sense}$ is from positions 20-28 of the sequence. The hairpin loop region may contain any suitable sequence. To construct shRNA vectors, see McIntyre & Fanning (2006) *BMC Biotechnol.* 6:1.

In an embodiment, double-stranded RNA or dsRNA refers to a double-stranded RNA which matches a predetermined gene sequence which is capable of activating cellular enzymes which degrade corresponding messenger RNA transcripts of the gene. These dsRNAs comprise nucleic acid molecules which may be short interfering RNA (siRNA) and may be used to inhibit gene expression. The term "double-stranded RNA" or "dsRNA," as used herein, refers to a double-stranded RNA molecule capable of RNA interference "RNAi," including small interfering RNAs "siRNA."

siRNA, shRNA and antisense oligonucleotide molecules as described herein may also include nucleic acid modifications known in the art to enhance stability and to enhance cleavage destruction of the target mRNA. With respect to the embodied nucleic acid molecules, a representative example may comprise a 19-base core which includes 2 or 3 nucleotide overhanging 3' ends, such as a 3' terminal thymidines (TT). The overhangs may play a structural role for presenting a symmetrical duplex to the RNA-Induced Silencing Complex (RISC). Often dTdT is selected because it can confer nuclease resistance to nucleic acid molecules. Nevertheless, some investigators prefer UU overhangs or overhangs that are complementary to the authentic mRNA target. What is most important is the identity of the 19-base core of the nucleic acid molecules towards a unique mRNA target.

The siRNA, shRNA and antisense oligonucleotide molecules may also be chemically synthesized de novo. The synthesized nucleic acid molecules may be in the form of a single-stranded nucleic acid molecule or may be in the form of a duplex with the cognate antisense nucleic acid molecule. The siRNA, shRNA and antisense oligonucleotides comprise a nucleic acid sequence which is complementary to a target MADD exon 13L nucleotide sequence and/or mRNA transcripts of MADD exon 13L.

RNA interference is a conserved pathway found in most eukaryotes where dsRNAs down-regulate expression of genes with complementary sequences. Long dsRNAs are degraded by the endoribonuclease Dicer into small effector molecules called siRNAs. siRNAs are usually around 21 base pairs (bp) long with a central 19 bp duplex and 2-base 3'-overhangs (this could be TT) (Elbashir, et al. (2001) *Genes & Dev.* 15:188-200). In mammals, Dicer processing occurs in a multiprotein complex with the RNA-binding protein TRBP. The nascent siRNA associates with Dicer, TRBP, and Argonaute 2 (Ago2) to form the RISC. Once in RISC, one strand of the siRNA (the passenger strand/the strand that has the same sequence as the target mRNA) is degraded or discarded while the other strand (the guide strand/strand that is complementary to the targeted mRNA) remains to direct sequence specificity of the silencing complex. The Ago2 component of RISC is a ribonuclease that will cleave the target RNA under direction of the guide strand. Once the RISC complex is activated, it can move on to target additional mRNA targets. This effect amplifies gene silencing and allows the therapeutic effect to last for 3-7 days in rapidly dividing cells. Many researchers today employ synthetic RNA duplexes as their RNAi reagents, which mimic the natural siRNAs that result from Dicer processing of long substrate RNAs. These synthetic siRNA duplexes are transfected into cell lines where they mimic in vivo Dicer products.

The modulation of MADD expression and/or downregulation of MADD expression utilizing siRNA, shRNA or antisense oligonucleotides may augment traditional cancer therapies.

From a chemotherapeutic perspective, cancer chemotherapy has advanced dramatically in recent years. Numerous cancer chemotherapy substances have been identified which are effective in treating cancer. Nonetheless, many cancer chemotherapies are characterized by toxic side effects which are often encountered with administration of particular chemotherapeutics.

For example, the administration of many established chemotherapeutics is well-known to result in unwanted side-effects including nausea and vomiting, loss of appetite, change in taste, thinned or brittle hair, joint pain, nail change, and tingling in the hands or toes. More serious side effects such as impaired bowel movement, difficulty in swallowing, dizziness, shortness of breath, severe exhaustion, and chest pain may also occur. Consequently, there is an unmet need to provide care givers with a treatment regimen which is possessed of the advantages of the chemotherapeutic potential of various known chemotherapeutics, but without the unwanted side effects which limit compliance and efficacy.

Chemotherapeutics, such as protein kinase inhibitors, have been administered in the treatment of various forms of chronic myeloid leukemia, breast cancer, lung cancer, colorectal cancer, primary kidney cancer, liver cancer and thyroid cancer, and other types of solid tumor cancers as well as Kaposi's sarcoma with a good degree of success. Protein kinase inhibitors may be characterized as types of enzyme inhibitors which block the action of protein kinases which act by adding a phosphate group to a protein, thereby modulating its function. The protein kinases add phosphate groups to serine, threonine, or tyrosine amino acids on the protein. Most kinases act on both serine and threonine, tyrosine kinases act on tyrosine, and dual-specificity kinases act on all three. There are a few protein kinases that can phosphorylate other amino acids such as histidine kinases phosphorylate histidine residues. Protein kinase inhibitors act by directly interacting with the ATP binding site or by altering the kinase conformation to prevent productive ATP binding. Protein Kinase Inhibitors can be allosteric inhibitors, protein substrate competitive inhibitors, ATP competitive inhibitors or covalent bond forming inhibitors.

Representative protein kinase inhibitors include Imatinib, trastuzumab, bevacizumab, gefitinib, cetuximab, Sorafenib. Imatinib is an inhibitor of c-Abl and is used in the treatment of chronic myeloid leukemia. Trastuzumab is an inhibitor of HER2 and is used in the treatment of breast cancer. Bevacizumab is an inhibitor of vascular endothelial growth factor receptor and is used in the treatment of metastatic colorectal cancer. Gefitinib and Cetuximab are inhibitors of EGF receptors and used in the treatment of lung and colorectal cancer. Sorafenib is a small inhibitor of various tyrosine protein kinases such as VEGFR, PDGFR, and Raf family kinases, and used in the treatment of advanced renal cell carcinoma, hepatocellular carcinoma and radioactive iodine resistant advanced thyroid cancer. Erlotinib, like gefitinib, inhibits EGFR. Lapatinib is a dual inhibitor of EGFR and a subclass called Human EGFR type 2. EGFR is not the only growth factor targeted. Sunitinib is multi-targeted, inhibiting PDGFR and VEGF. Nilotinib inhibits the fusion protein bcr-abl and is typically prescribed when a patient has shown resistance to imatinib. More protein kinase inhibitors are currently in development. Three TKIs are currently showing promise in clinical trials. Bosutinib targets abl and src kinases. Neratinib, like lapatinib, inhibits EGFR and Human EGFR type 2. Vatalanib inhibits both VEGFR and PDGFR.

Protein kinase inhibitors also pose adverse effects on patients such as cardiovascular and dermatological toxicities. Myelosuppression and neutropenia are the most common adverse effects associated with c-Abl inhibitors such as Imatinib. For the EGFR-targeted inhibitors, most commonly observed side effects are fatigue, diarrhea, and the development of various dermatological toxicities such as acne-form-like rash, and hand-foot syndrome.

Chemotherapeutics, such as anthracyclines, are used in the treatment of various solid tumors and hematological malignancies. Anthracyclines work by inhibiting DNA and RNA synthesis by intercalating between base pairs of the DNA/RNA strand and thereby, preventing the replication of rapidly dividing cancer cells. They also work by inhibiting topoisomerase II enzyme, thereby preventing the relaxing of supercoiled DNA and hence, blocking DNA transcription and replication. Anthracyclines are among the most commonly used chemotherapeutic agents. The effect of anthracyclines in treating cancer could be attributed to their cytostatic and cytotoxic actions such as free radical formation, lipid peroxidation and direct membrane effects. The best characterized mechanisms are the interactions with the DNA topoisomerase II or DNA itself via intercalation or covalent binding formation and modification of the bases, which are responsible for disturbances in DNA replication and transcription, eventually leading to induction of apoptotic cell death. Anthracyclines are used in the treatment of cancers including leukemias, lymphomas, breast, stomach, uterine, ovarian, bladder cancer and lung cancers.

Representatives of anthracyclines include daunorubicin, doxorubicin, epirubicin, idarubicin and valrubicin. Daunomycin (daunorubicin) was the first anthracycline compound to be characterized structurally and stereochemically. Daunorubicin is used in treating acute lymphoblastic and myeloblastic leukaemias. Adriamycin (generic name doxorubicin) is a hydroxyl derivative of daunorubicin. Doxorubicin is one of the most widely used chemotherapeutic agents and is generally prescribed in combination with other drugs. Doxorubicin has a broad spectrum of activity. It is one of the most effective drugs for solid tumor treatment, e.g., breast cancer, small cell lung cancer and ovarian carcinoma treatments. It has significant activity against bladder, stomach, liver and thyroid tumors, Ewing's and osteogenic bone tumors, soft tissue sarcoma, neuroblastoma and Wilms tumor. It is also active against multiple myeloma, several types of leukemia and cutaneous T-cell lymphoma. It also plays an important role in treatment of Hodgkin's disease and non-Hodgkin's lymphomas. Epirubicin is an epimer of doxorubicin and differs only in the orientation of the C-4 hydroxyl group on the sugar. Because of this slight change in the structure, epirubicin has lower cardiotoxicity than doxorubicin. Epirubicin is used in the treatment of gastric and breast cancer and is also indicated for the treatment of carcinoid, endometrial, lung, ovarian, esophageal and prostate cancers as well as soft tissue sarcomas. Idarubicin is an analog of daunorubicin. It lacks the C-4 methoxy group and this increases its lipophilicity. Idarubicin has improved activity as induction therapy for acute myelogenous leukaemia. Valrubicin is N-trifluoroacetyl, 1-4-valerate derivative of doxorubicin. Valrubicin enters cells more rapidly than doxorubicin. It is used specifically in the treatment of early bladder cancer.

One of the major side effects of anthracyclines is the cardiotoxicity, which often presents as ECG changes and arrhythmias, or as a cardiomyopathy leading to heart failure. It is related to a patient's cumulative lifetime dose and therefore, treatment is usually stopped upon reaching the maximum cumulative dose of that particular anthracycline. Cardiotoxicity is further overcome by using Dexrazoxane, a cardioprotectant, or by using liposomal formulations of daunorubicin and doxorubicin or by using longer infusion rates.

Chemotherapeutics, such as nucleoside analogs, are synthetic, chemically-modified compounds that mimic their physiological counterparts and thereby interfere with the synthesis of nucleic acids by incorporating into DNA and RNA. They can also interact and inhibit essential enzymes such as DNA-dependent DNA polymerase, RNA-dependent DNA polymerase, RNA-dependent RNA polymerase, kinases, DNA methyltransferases, pyrimidine and purine nucleoside phosphorylase etc. Nucleoside analogues exert cytotoxic effect by being incorporated into and altering the DNA and RNA macromolecules themselves, by interfering with various enzymes involved in synthesis of nucleic acids, or by modifying the metabolism of physiological nucleosides.

Representative nucleoside analogues, such as Gemcitabine, 5-Fluorouracil and Cytarabine, are used in the treatment of breast cancer, non-small cell lung cancer, pancreatic cancer, bladder cancer, biliary tract cancer and colon cancer, esophageal cancer, stomach cancer, pancreatic cancer, breast cancer, cervical cancer, and other types of solid tumor cancers. The triphosphate analogue of gemcitabine replaces cytidine during DNA replication leading to arrest of tumor growth. 5-Fluorouracil acts as a thymidylate synthase inhibitor leading to blockage of synthesis of thymidine, which eventually inhibits DNA replication.

Nucleoside analogues also present certain unwanted side effects such as nausea, vomiting, poor appetite, low blood counts.

Chemotherapeutics and apoptosis-inducing molecules, have been administered in the treatment of various forms of circulatory cancers such as leukemia and lymphoma, melanoma, bladder and kidney cancers, and other types of solid tumor cancers with a good degree of success. Cytokines may be characterized as protein molecules that play a role in regulating and directing the immune system. For cancer therapy, cytokines are synthesized and injected in larger does than the body normally produces. There are 2 common cytokines that are used in cancer immunotherapy, namely Interleukin 2 (IL2) and Interferon-α (IFN-α). In cancer treatment, IL2 is designed to target adaptive immune cells, T-cells and B-cells, to respond to tumors and IFN-α helps the body to generate innate immune cells, such as dendritic cells and macrophages that are designed to target the unhealthy cells.

TRAIL is a well-known cytotoxic protein which induces apoptosis in tumor cells, but not in normal cells. Tumors develop resistance to treatments with biologics such as TRAIL, like they do against other modalities of treatment such as chemotherapeutic agents. Therefore, although TRAIL is a highly desirable biologic that induces selective apoptosis in tumor cells, the tumors often develop resistance to TRAIL and thus their therapeutic utility is limited. Thus, there is an unmet need for providing a treatment which would include the administration of a new class of drug which would help overcome resistance to TRAIL and cause remission without undesirable side effects.

Chemotherapeutics, such as alkylating agents, act by attaching an alkyl group to the guanine base of DNA, thereby disrupting the normal functioning. They can be used on a wide range of cancers due to their ability to have this effect on a cancer cell on any phase of its life cycle. They can be used in the treatment of lymphoma, leukemia, testicular cancer, melanoma, brain cancer and breast cancer. Alkylating agents act by irreversibly binding to DNA. Once bound, the altered molecule leads to disruption of normal action and replication of DNA, ultimately leading to apoptosis or arrest of cellular replication. Therefore, upon treatment with alkylating agents, they can limit tumor growth and lead to tumor destruction. The most beneficial effect of alkylating agents is that it can be used to treat slow growing solid tumors and leukemia. They can also be used to treat lung cancer, ovarian cancer, breast cancer, lymphomas, sarcomas, myelomas, and Hodgkin's disease.

Representatives of alkylating agents can be classified as classical alkylating agents such as cyclophosphamide, mechlorethane; alkylating-like agents such as cisplatin, carboplatin; and agents such as procarbazine, ifosfamide, melphalan, chlorambucil, cyclophosphamide, streptozocin, carmustine, lomustine, busulfan, and dacarbazine. Mechlorethamine, marketed under the tradename MUSTARGEN®, is given by injection to treat Hodgkin's disease and non-Hodgkin's lymphoma, and as a palliative therapy for breast and lung cancers, and given as a topical treatment for skin lesions of mycosis fungoides (cutaneous T-cell lymphoma). Ifosfamide, sold under the tradename IFEX®, is used to treat both Hodgkin's and non-Hodgkin's lymphoma, as well as recurrent testicular cancer and germ cell tumors, sarcomas, lung cancer, bladder cancer, head and neck cancer, and cervical cancer. It is administered intravenously. Melphalan is a chemotherapy drug sold under the tradename ALKERAN®, and is also referred to as L-PAM or phenylalanine mustard. It is used to treat multiple myeloma, ovarian cancer, neuroblastoma, rhabdomyosarcoma, and breast cancer. Chlorambucil is sold by the tradename LEUKERAN®, and is most widely used to treat chronic lymphocytic leukemia, malignant lymphomas including lymphosarcoma, giant follicular lymphoma, and Hodgkin's disease. It has also been successfully used to treat non-Hodgkin's lymphoma, breast, ovarian and testicular cancer, Waldenstrom's macroglobulinemia, thrombocythemia, and choriocarcinoma. It comes in coated tablet form. Cyclophosphamide is marketed under the tradename CYTOXAN® or NEOSAR®, and is used to treat Hodgkin's and non-Hodgkin's lymphoma, Burkitt's lymphoma, chronic lymphocytic leukemia, chronic myelocytic leukemia, acute myelocytic leukemia, acute lymphocytic leukemia, t-cell lymphoma, multiple myeloma, neuroblastoma, retinoblastoma, rhabdomyosarcoma, Ewing's sarcoma and breast, testicular, endometrial, ovarian, and lung cancers. Streptozocin is sold under the tradename ZANOSAR®, and is used to treat islet cell pancreatic cancer. Carmustine is sold under the tradename BICNU®, and is used for some kinds of brain tumors, glioblastoma, brainstem glioma, medulloblastoma, astrocytoma, ependymoma, and metastatic brain tumors. It is also used in treatment for multiple myeloma, Hodgkin's disease, non-Hodgkin's lymphoma, melanoma, lung cancer, and colon cancer. Lomustine, sold under the tradename CEENU®, is used to treat primary and metastatic brain tumors, Hodgkin's disease and non-Hodgkin's lymphoma, and has also been used for melanoma, lung, and colon cancer. Busulfan, sold under the tradenames BUSULFEX® and MYLERAN®, is used to treat chronic myelogenous leukemia. Dacarbazine is sold under the tradename DTIC-DOME® and is used to treat metastatic malignant melanoma, Hodgkin's disease, soft tissue sarcomas, neuroblastoma, fibrosarcomas, rhabdomyosarcoma, islet cell carcinoma, and medullary thyroid carcinoma. Temozolomide is sold under the tradename TEMODAR®, and is used to treat the specific types of brain tumors anaplastic astrocytoma and glioblastoma multiforme. Thiotepa, sold under the tradename THIOPLEX®, is an alkylating agent used to treat breast cancer, ovarian cancer, Hodgkin's disease, and non-Hodgkin's lymphoma. It is given by intravenous infusion. Altretamine is sold under the tradename HEXALEN® and is also called hexamethylmelamine or HMM. It is used to treat ovarian cancer.

Alkylating agents are also associated with side effects. They are toxic to normal cells as well, particularly rapidly dividing cells such as those in gastrointestinal tract and bone marrow. Long term use of alkylating agents can result in permanent infertility by reducing sperm production in males and leading to cessation of menstruation in females. Many alkylating agents can also lead to secondary cancers like acute myeloid leukemia.

Moreover, while the life expectancy under protein kinase inhibitor therapy, anthracycline therapy, nucleoside analog therapy, apoptosis-inducing molecular therapy or alkylating agent therapy is extended, it is not without undesirable side-effects effects of these drugs. Thus, there is an unmet need for providing a treatment which would include the administration of a new class of drug with a different mechanism of action, and which would result in a more complete remission profile without undesirable side effects.

SUMMARY OF THE INVENTION

This invention may be summarized inter alia to include:

A combination of antineoplastic agents useful for treating cancer comprising an effective amount of one or more nucleic acid molecules capable of down-regulating expression of at least one splice variant of the IG20 gene, wherein not all splice variants of the IG20 gene are down-regulated, and a chemotherapeutic selected from the group of one or more protein kinase inhibitor chemotherapeutics, one or more anthracycline chemotherapeutics, one or more nucleoside analogs, one or more apoptosis-inducing molecular therapeutics or one or more alkylating agent chemotherapeutics.

Such a combination, wherein the at least one splice variant of the IG20 gene is selected from a MADD splice variant, SNPs, allelic variations thereof, polymorphisms thereof, and genetic mutations thereof.

Such a combination, wherein the at least one splice variant of the IG20 gene is a MADD splice variant which exhibits exon 13L.

Such a combination, wherein the one or more nucleic acid molecules capable of down-regulating expression of the at least one splice variant of the IG20 gene is selected from siRNA, shRNA and antisense oligonucleotides.

Such a combination, wherein the siRNA, shRNA and antisense oligonucleotides comprise nucleic acids which are complementary to a nucleic acid sequence of exon 13L of a MADD splice variant, SNPs, allelic variations thereof, polymorphisms thereof, and genetic mutations thereof, and/or an mRNA transcript thereof.

Such a combination, wherein the nucleic acid molecule capable of down-regulating expression of at least one splice variant of the IG20 gene is comprised in an siRNA or shRNA.

Such a combination, wherein the siRNA and shRNA are encoded by a nucleic acid molecule which includes the structure:

$X_{sense}$–hairpin loop–$X_{anti\text{-}sense}$, wherein X includes or consists essentially of a nucleic acid sequence CGGCGAATCTATGACAATC (SEQ ID NO:1).

Such a combination, wherein the siRNA or shRNA comprises a nucleic acid having the sequence CGGCGAAUCUAUGACAAUC (SEQ ID NO:2).

Such a combination, wherein the siRNA or shRNA comprises a nucleic acid having the sequence CGGCGAAUCUAUGACAAUC (SEQ ID NO:2) and is in the form of a duplex with a cognate nucleic acid having the sequence GAUUGUCAUAGAUUCGCCG (SEQ ID NO:10).

Such a combination, wherein the shRNA and siRNA are encoded by a nucleic acid having the sequence CGAATCTATGACAATCTTCAAGAGAGATTGTCATAGATTCGCCG (SEQ ID NO:3), wherein a hairpin loop region is from positions 20-28 of the sequence.

Such a combination, wherein the siRNA, shRNA and antisense oligonucleotide comprising nucleic acids which are complementary to a nucleic acid sequence of exon 13L of a MADD splice variant of the IG20 gene and/or an mRNA transcript thereof comprises a nucleic acid having the sequence selected from GAUUGUCAUAGAUUCGCCGTT (SEQ ID NO:4) and GAUUGUCAUAGAUUCGCCG (SEQ ID NO:10).

Such a combination, wherein the one or more nucleic acid molecules capable of down-regulating expression of the at least one splice variant of the IG20 gene is comprised in a drug delivery system.

Such a combination, wherein the drug delivery system is a targeted liposome formulation or a lentivirus vector.

Such a combination, wherein the one or more protein kinase inhibitor chemotherapeutics is selected from imatinib, trastuzumab, bevacizumab, gefitinib, cetuximab, Sorafenib, toceranib, erlotinib, lapatinib, sunitinib, nilotinib, bosutinib, neratinib and vatalanib and the cancer is selected from chronic myeloid leukemia, breast cancer, lung cancer, colorectal cancer, primary kidney cancer, liver cancer and thyroid cancer, and other types of solid tumor cancers as well as Kaposi's sarcoma.

Such a combination, wherein the one or more anthracycline chemotherapeutics is selected from daunorubicin, doxorubicin, epirubicin, idarubicin and valrubicin and the cancer is selected from leukemias, lymphomas, breast, stomach, uterine, ovarian, bladder cancer and lung cancers, and other types of solid tumor cancers as well as Kaposi's sarcoma.

Such a combination, wherein the one or more nucleoside analog chemotherapeutic is selected from gemcitabine, 5-fluorouracil and cytarabine and the cancer is selected from breast cancer, non-small cell lung cancer, pancreatic cancer, bladder cancer, biliary tract cancer and colon cancer, esophageal cancer, stomach cancer, cervical cancer, and other types of solid tumor cancers.

Such a combination, wherein the one or more apoptosis-inducing molecular therapeutic is selected from Interleukin 2 (IL2), Interferon-α (IFN-α) and Tumor necrosis factor α-related apoptosis-inducing ligand (TRAIL) and the cancer is selected from circulatory cancers such as leukemia and lymphoma, melanoma, bladder and kidney cancers, and other types of solid tumor cancers.

Such a combination, wherein the one or more alkylating agent chemotherapeutic is selected cyclophosphamide, mechlorethane, cisplatin, carboplatin, procarbazine, ifosfamide, melphalan, chlorambucil, cyclophosphamide, streptozocin, carmustine, lomustine, busulfan, and dacarbazine and the cancer is selected from slow growing solid tumors and leukemia, lung cancer, ovarian cancer, breast cancer, lymphomas, sarcomas, myelomas, Hodgkin's disease, topical treatment for skin lesions of mycosis fungoides (cutaneous T-cell lymphoma), both Hodgkin's and non-Hodgkin's lymphoma, testicular cancer, germ cell tumors, bladder cancer, head and neck cancer, cervical cancer, multiple myeloma, neuroblastoma, rhabdomyosarcoma, lymphocytic leukemia, malignant lymphomas including lymphosarcoma, giant follicular lymphoma, Burkitt's lymphoma, chronic lymphocytic leukemia, chronic myelocytic leukemia, acute myelocytic leukemia, acute lymphocytic leukemia, t-cell lymphoma, multiple myeloma, retinoblastoma, Ewing's sarcoma, endometrial cancer, islet cell pancreatic cancer, brain tumors, glioblastoma, brainstem glioma, medulloblastoma, astrocytoma, ependymoma, and metastatic brain tumors, colon cancer, fibrosarcomas, anaplastic astrocytoma, and glioblastoma multiforme.

Such a combination, wherein the one or more protein kinase inhibitor chemotherapeutic, one or more anthracycline chemotherapeutic, one or more nucleoside analog chemotherapeutic, one or more apoptosis-inducing molecular therapeutic, or one or more alkylating agent chemotherapeutic is in the form of a pharmaceutically acceptable salt.

Moreover, a method of treating cancers selected from chronic myeloid leukemia, breast cancer, lung cancer, colorectal cancer, primary kidney cancer, liver cancer and thyroid cancer, and other types of solid tumor cancers as well as Kaposi's sarcoma in a subject in need thereof, comprising administering an effective amount of a combination of antineoplastic agents comprising an effective amount of one or more nucleic acid molecules capable of down-regulating expression of at least one splice variant of the IG20 gene, wherein not all splice variants of the IG20 gene are down-regulated, and one or more protein kinase inhibitor chemotherapeutic.

Such a method, wherein the one or more protein kinase inhibitor chemotherapeutic is selected from imatinib, trastuzumab, bevacizumab, gefitinib, cetuximab, sorafenib, toceranib, erlotinib, lapatinib, sunitinib, nilotinib, bosutinib, neratinib and vatalanib.

Moreover, a method of treating cancers selected from leukemias, lymphomas, breast, stomach, pancreas, uterine, ovarian, cervical, prostate, melanoma, esophageal, bladder cancer, liver cancer and thyroid tumors, and lung cancers, and other types of solid tumor cancers as well as Kaposi's sarcoma in a subject in need thereof, comprising administering an effective amount of a combination of antineoplastic agents comprising an effective amount of one or more nucleic acid molecules capable of down-regulating expression of at least one splice variant of the IG20 gene, wherein not all splice variants of the IG20 gene are down-regulated, and one or more anthracycline chemotherapeutic.

Such a method, wherein the one or more anthracycline chemotherapeutic is selected from daunorubicin, doxorubicin, epirubicin, idarubicin and valrubicin.

Moreover, a method of treating cancers selected from breast cancer, non-small cell lung cancer, pancreatic cancer, bladder cancer, biliary tract cancer and colon cancer, esophageal cancer, stomach cancer, pancreatic cancer, breast cancer, cervical cancer, and other types of solid tumor cancers in a subject in need thereof, comprising administering an effective amount of a combination of antineoplastic agents comprising an effective amount of one or more nucleic acid molecules capable of down-regulating expression of at least one splice variant of the IG20 gene, wherein not all splice variants of the IG20 gene are down-regulated, and one or more nucleoside analog chemotherapeutic.

Such a method, wherein the one or more nucleoside analog chemotherapeutic is selected from gemcitabine, 5-fluorouracil and cytarabine.

Moreover, a method of treating cancers selected from circulatory cancers such as leukemia and lymphoma, melanoma, bladder and kidney cancers, and other types of solid tumor cancers in a subject in need thereof, comprising administering an effective amount of a combination of antineoplastic agents comprising an effective amount of one or more nucleic acid molecules capable of down-regulating expression of at least one splice variant of the IG20 gene, wherein not all splice variants of the IG20 gene are down-regulated, and one or more apoptosis-inducing molecular therapeutic.

Such a method, wherein the one or more apoptosis-inducing molecular therapeutic is selected from Interleukin 2 (IL2), Interferon-α (IFN-α) and Tumor necrosis factor α-related apoptosis-inducing ligand (TRAIL).

Moreover, a method of treating cancers selected from slow growing solid tumors and leukemia, lung cancer, ovarian cancer, breast cancer, lymphomas, sarcomas, myelomas, Hodgkin's disease, topical treatment for skin lesions of mycosis fungoides (cutaneous T-cell lymphoma), both Hodgkin's and non-Hodgkin's lymphoma, testicular cancer, germ cell tumors, bladder cancer, head and neck cancer, cervical cancer, multiple myeloma, neuroblastoma, rhabdomyosarcoma, lymphocytic leukemia, malignant lymphomas including lymphosarcoma, giant follicular lymphoma, Burkitt's lymphoma, chronic lymphocytic leukemia, chronic myelocytic leukemia, acute myelocytic leukemia, acute lymphocytic leukemia, t-cell lymphoma, multiple myeloma, retinoblastoma, Ewing's sarcoma, endometrial cancer, islet cell pancreatic cancer, brain tumors, glioblastoma, brainstem glioma, medulloblastoma, astrocytoma, ependymoma, and metastatic brain tumors, colon cancer, fibrosarcomas, anaplastic astrocytoma, and glioblastoma multiforme in a subject in need thereof, comprising administering an effective amount of a combination of antineoplastic agents comprising an effective amount of one or more nucleic acid molecules capable of down-regulating expression of at least one splice variant of the IG20 gene, wherein not all splice variants of the IG20 gene are down-regulated, and one or more alkylating agent chemotherapeutic.

Such a method, wherein the one or more alkylating agent chemotherapeutic is selected from cyclophosphamide, mechlorethane, cisplatin, carboplatin, procarbazine, ifosfamide, melphalan, chlorambucil, cyclophosphamide, streptozocin, carmustine, lomustine, busulfan, and dacarbazine.

Such methods of treating cancers, wherein the cancers exhibit expression of at least one splice variant of the IG20 gene.

Such methods of treating cancers, wherein the cancers exhibit expression of the MADD splice variant of the IG20 gene, SNPs, allelic variations thereof, polymorphisms thereof, and genetic mutations thereof.

Such methods of treating cancers, wherein MADD splice variant exhibits exon 13L of the IG20 gene.

Such methods of treating cancers, wherein the one or more nucleic acid molecules capable of down-regulating expression of at least one splice variant of the IG20 gene is selected from siRNA, shRNA and antisense oligonucleotides.

Such methods of treating cancers, wherein the siRNA, shRNA and antisense oligonucleotides comprise nucleic acids which are complementary to a nucleic acid sequence of exon 13L of a MADD splice variant, SNPs, allelic variations thereof, polymorphisms thereof, and genetic mutations thereof, of the IG20 gene and/or an mRNA transcript thereof.

Such methods of treating cancers, wherein the nucleic acid molecule capable of down-regulating expression of at least one splice variant of the IG20 gene is comprised in siRNA or shRNA.

Such methods of treating cancers, wherein the siRNA and shRNA is encoded by a nucleic acid molecule which includes the structure:

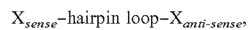
$X_{sense}$–hairpin loop–$X_{anti\text{-}sense}$, wherein X includes or consists essentially of a nucleic acid sequence CGGCGAATCTATGACAATC (SEQ ID NO:1).

Such methods of treating cancers, wherein the siRNA and shRNA comprises a nucleic acid having the sequence CGGCGAAUCUAUGACAAUC (SEQ ID NO:2).

Such methods of treating cancers, wherein the siRNA and shRNA comprises a nucleic acid having the sequence CGGCGAAUCUAUGACAAUC (SEQ ID NO:2) and is in the form of a duplex with a cognate nucleic acid having the sequence GAUUGUCAUAGAUUCGCCG (SEQ ID NO:10).

Such methods of treating cancers, wherein the shRNA is encoded by a nucleic acid having the sequence CGAATCTATGACAATCTTCAAGAGAGATTGTCATAGATTCGCCG (SEQ ID NO:3), wherein a hairpin loop region is from positions 20-28 of the sequence.

Such methods of treating cancers, wherein the siRNA, shRNA and antisense oligonucleotides comprising nucleic acids which are complementary to a nucleic acid sequence of exon 13L of a MADD splice variant of the IG20 gene and/or an mRNA transcript thereof comprise a nucleic acid having the sequence selected from GAUUGUCAUAGAUUCGCCGTT (SEQ ID NO:4) and GAUUGUCAUAGAUUCGCCG (SEQ ID NO:10).

Such methods of treating cancers, wherein the one or more siRNA, shRNA and antisense oligonucleotides is administered in the form of a liposomal formulation or by lentivirus transfection.

Such methods of treating cancers, wherein the one or more siRNA, shRNA and antisense oligonucleotides is administered as an adjuvant.

Such methods of treating cancers, wherein the one or more protein kinase inhibitor chemotherapeutic, one or more anthracycline chemotherapeutic, one or more nucleoside analog chemotherapeutic, one or more apoptosis-inducing molecular therapeutic or the one or more alkylating agent chemotherapeutic is administered in the form of a pharmaceutical composition further comprising one or more pharmaceutically acceptable diluents, excipients, or carriers.

Such methods of treating cancers, wherein the one or more siRNA, shRNA and antisense oligonucleotides is administered prior to the one or more protein kinase inhibitor chemotherapeutic, one or more anthracycline chemotherapeutic, one or more nucleoside analog chemotherapeutic, one or more apoptosis-inducing molecular therapeutic or the one or more alkylating agent chemotherapeutic; or is administered simultaneously with the one or more protein kinase inhibitor chemotherapeutic, one or more anthracycline chemotherapeutic, one or more nucleoside analog chemotherapeutic, one or more apoptosis-inducing molecular therapeutic or the one or more alkylating agent chemotherapeutic.

Such methods of treating cancers, wherein the one or more siRNA, shRNA and antisense oligonucleotides is administered in the form of a pharmaceutical composition further comprising one or more pharmaceutically acceptable diluents, excipients, or carriers.

Such methods of treating cancers, wherein the one or more siRNA, shRNA, and antisense oligonucleotides and the one or more protein kinase inhibitor chemotherapeutic, one or more anthracycline chemotherapeutic, one or more nucleoside analog chemotherapeutic, one or more apoptosis-inducing molecular therapeutic or the one or more alkylating agent chemotherapeutic are formulated in a dosage pack and are administered according to a selected treatment regime.

BRIEF DESCRIPTION OF THE DRAWINGS

FIG. 1 shows human IG20 splice variants generated by alternative mRNA splicing. The cDNA sequence homology among the seven IG20 splice variants is shown. Filled bars represent regions of complete homology between all variants. Empty areas indicate exons 13L, 16, 21, 26 and 34, which, when spliced in different combinations, produce the seven splice variants shown on the left. Splicing of exon 34 in KIAA0358 and IG20-SV4 induces an early stop codon in exon 35. Shown also are different 5' untranslated regions (UTRs) for different splice variant.

DETAILED DESCRIPTION OF THE INVENTION

The present inventors have now identified novel methods of administering representative chemotherapeutics in combination with nucleic acid molecules capable of down-regulating the expression of the MADD splice variant, which result in dramatic synergistic effects including increased efficacy as well as reduced side-effects.

The present inventors have conceived and demonstrate for the first time that the clinical combination of one or more nucleic acid molecules capable of down-regulating expression of at least one splice variant of the IG20 gene, wherein not all splice variants of the IG20 gene are down-regulated, with conventional chemotherapeutics such as protein kinase inhibitors, anthracyclines, nucleoside analogs, apoptosis-inducing molecular therapeutics or alkylating agents is an unexpectedly valuable pharmacotherapeutic approach to treating various forms of cancer. The present inventors demonstrate that, when administered in combination to subjects suffering from cancers, the effects of siRNA, shRNA and antisense oligonucleotides, wherein the siRNA, shRNA and antisense oligonucleotides comprise a nucleic acid sequence which is complementary to a nucleic acid sequence of exon 13L of the MADD splice variant or to an mRNA transcript of exon 13L of the MADD splice variant, and chemotherapeutics such as protein kinase inhibitors, anthracyclines, nucleoside analogs, apoptosis-inducing molecular therapeutics or alkylating agents is of unexpected benefit and, at least over a period of time results in an unexpectedly super-additive relief of symptoms, evidenced by dramatic reduction in, or absence of, symptoms, tumor growth and tumor survival, and in this way will be particularly beneficial in the treatment of multiple cancers. Moreover, the combination of at least one siRNA, shRNA and antisense oligonucleotides, wherein the siRNA, shRNA and antisense oligonucleotides comprise a nucleic acid sequence which is complementary to a nucleic acid sequence of exon 13L of the MADD splice variant or to an mRNA transcript of exon 13L of the MADD splice variant, and chemotherapeutics such as protein kinase inhibitors, anthracyclines, nucleoside analogs, apoptosis-inducing molecular therapeutics or alkylating agents may, for the first time, show promise in providing complete remission from multiple cancers, as well as enhanced margin of safety and tolerance.

Therefore, it is an object of the present invention to provide novel combination antineoplastic treatments comprising administering representative chemotherapeutics in combination with nucleic acid molecules capable of down-regulating the expression of the MADD splice variant, which combination antineoplastic treatments are effective in treating various cancers, and pharmaceutical compositions comprising such combination antineoplastic. It is a further object of the invention to provide a novel method of treating various cancers which include administering combination antineoplastic treatments comprising nucleic acid molecules capable of down-regulating the expression of the MADD splice variant and chemotherapeutics such as protein kinase inhibitors. An additional object of the invention is the provision of a process for producing targeted formulations and therapeutic delivery procedures for the combination antineoplastic treatments. Yet additional objects will become apparent hereinafter, and still further objects will be apparent to one skilled in the art.

Combination of the Invention

As specified above, in one aspect, the instant invention provides a novel drug combination useful for treating, preventing, arresting, delaying the onset of and/or reducing the risk of developing, or reversing at least one symptom of a cancer in a mammal comprising administering to said mammal an amount of siRNA, shRNA and/or antisense oligonucleotides capable of down-regulating the expression of the MADD splice variant of an IG20 gene, wherein the splice variant is MADD, SNPs, allelic variations thereof, polymorphisms thereof, and genetic mutations thereof, and wherein not all splice variants of IG20 are down-regulated, and protein kinase inhibitors, anthracyclines, nucleoside analogs, apoptosis-inducing molecular therapeutics or alkylating agents at therapeutically effective dosages which, when combined, provide a beneficial effect.

Definitions

The term "combination" applied to active ingredients is used herein to define a single pharmaceutical composition (formulation) comprising both drugs of the invention (i.e., one or more siRNA, shRNA and antisense oligonucleotide capable of down-regulating the expression of the MADD splice variant of an IG20 gene, wherein not all splice variants of IG20 are down-regulated, and one or more protein kinase inhibitors, anthracyclines, nucleoside analogs, apoptosis-inducing molecular therapeutics or alkylating agents) or two separate pharmaceutical compositions (formulations), each comprising a single drug of the invention (i.e., one or more siRNA, shRNA and antisense oligonucleotide capable of down-regulating the expression of the MADD splice variant of an IG20 gene, wherein not all splice variants of IG20 are down-regulated and one or more protein kinase inhibitors, anthracyclines, nucleoside analogs, apoptosis-inducing molecular therapeutics or alkylating agents), to be administered conjointly or in a pretreatment/treatment protocol.

Within the meaning of the present invention, the term "conjoint administration" is used to refer to administration of the one or more siRNA, shRNA and antisense oligonucleotide capable of down-regulating the expression of the MADD splice variant of an IG20 gene, wherein not all splice variants of IG20 are down-regulated and one or more protein kinase inhibitors, anthracyclines, nucleoside analogs, apoptosis-inducing molecular therapeutics or alkylating agents simultaneously in one composition, or simultaneously in different compositions, or sequentially in different compositions. For the sequential administration to be considered "conjoint," however, the administration of the one or more siRNA, shRNA and antisense oligonucleotide capable of down-regulating the expression of the MADD splice variant of an IG20 gene, wherein not all splice variants of IG20 are down-regulated and one or more protein kinase inhibitors, anthracyclines, nucleoside analogs, apoptosis-inducing molecular therapeutics or alkylating agents must be administered separated by a time interval which still permits the resultant beneficial effect of conjoint treatment for treating, preventing, arresting, delaying the onset of and/or reducing the risk of developing a cancer in a mammal. For example, the one or more siRNA, shRNA and antisense oligonucleotide capable of down-regulating the expression of the MADD splice variant of an IG20 gene, wherein not all splice variants of IG20 are down-regulated and one or more protein kinase inhibitors, anthracyclines, nucleoside analogs, apoptosis-inducing molecular therapeutics or alkylating agents may be administered sequentially. For example, siRNA may be administered 8-72 hours (hrs) before the administration of the protein kinase inhibitor, anthracycline, nucleoside analog, apoptosis-inducing molecular therapeutic or alkylating agent so as to have the MADD expression down-modulated prior to treatment with the chemotherapeutic.

According to still another embodiment of the invention, the one or more siRNA, shRNA and antisense oligonucleotide capable of down-regulating the expression of the MADD splice variant of an IG20 gene is used as an adjuvant. An "adjuvant" in the context of the present description refers to an enhancer of the specific protein kinase inhibitor response. "Using the one or more siRNA, shRNA and antisense oligonucleotide capable of down-regulating the expression of the MADD splice variant of an IG20 gene" means including the one or more siRNA, shRNA and antisense oligonucleotide capable of down-regulating the expression of the MADD splice variant of an IG20 gene in a pre-treatment prior to the chemotherapy agent, or in combination with the chemotherapeutic agent for simultaneous delivery. An adjuvant such as the one or more siRNA, shRNA and antisense oligonucleotide capable of down-regulating the expression of the MADD splice variant of an IG20 gene in combination with a chemotherapeutic agent provides synergistic cell death.

Hence, in a further embodiment of the invention, the one or more siRNA, shRNA and antisense oligonucleotide capable of down-regulating the expression of the MADD splice variant of an IG20 gene are administered to mammals exhibiting cancers, including humans, activate the death of cancerous cells. The one or more siRNA, shRNA and antisense oligonucleotide capable of down-regulating the expression of the MADD splice variant of an IG20 gene and one or more chemotherapeutic agent may also be used to support apoptotic pathways in a situation of increased susceptibility to developing tumors, such as in the case of patients in remission.

The term "treat" is used herein to mean to relieve or alleviate at least one symptom of a disease in a subject. For example, in relation to cancer, the term "treat" may mean to relieve or alleviate tumor growth or symptoms associated with the cancer and/or cause tumor regression. Within the meaning of the present invention, the term "treat" may also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the cancer is associated with clinical manifestations, including without limitation drug induced undesirable side-effects. For example, as disclosed herein, a prophylactic administration of one or more siRNA, shRNA and antisense oligonucleotide capable of down-regulating the expression of the MADD splice variant of an IG20 gene and protein kinase inhibitors, anthracyclines, nucleoside analogs, apoptosis-inducing molecular therapeutics or alkylating agents may protect a recipient subject to risk of developing cancer (e.g., individuals having elevated levels of CA125, individuals, who exhibit histopathologic cancer markers; see also genetic screening and clinical analysis described in oncology literature for standard screening for various cancers). Similarly, according to the present invention, a therapeutic administration of one or more siRNA, shRNA and antisense oligonucleotide capable of down-regulating the expression of the MADD splice variant of an IG20 gene and protein kinase inhibitors can lead to slow-down in the development of clinical symptoms or even regression of symptoms.

The term short interfering RNA (siRNA) refers to RNA molecules which are capable of interfering with a particular gene transcription, thereby silencing the gene expression of a target protein. Representative mechanisms of this process may comprise administration of nucleic acid molecules comprising siRNAs, dsRNAs, short hairpin RNAs (shRNA) and/or antisense oligonucleotides complementary to a nucleic acid sequence of exon 13L of the MADD splice variant mRNA transcript. dsRNA and short hairpin RNAs are cleaved by an endo-ribonuclease Dicer, which cuts the dsRNA or shRNA into constituent siRNA. The siRNA operates through the formation of RNA-induced Silencing Complexes or RISCs. The RISC complex unwinds the siRNA to form single stranded siRNA. The RISC, comprising single stranded siRNAs binds to the target mRNA, cleaving the mRNA, rendering it unrecognizable and thereby silencing the production of the intended protein.

Within the meaning of the present invention, the terms "siRNA, shRNA and antisense oligonucleotide capable of down-regulating the expression of the MADD splice variant of an IG20 gene" are used to refer to drugs, which target messenger RNAs. Embodiment siRNA, shRNA and antisense oligonucleotide capable of down-regulating the expression of the MADD splice variant of an IG20 gene of the invention may be siRNA derivatives such as modified siRNAs, shRNAs and/or antisense oligonucleotides comprise nucleic acids which are complementary to the nucleic acid sequence of exon 13L of the MADD splice variant mRNA transcript. Particular embodiments include those substances described in U.S. Pat. No. 7,910,723.

Design of siRNA, shRNA and antisense oligonucleotide capable of down-regulating the expression of the MADD splice variant of an IG20 gene may be accomplished through techniques which have been established. The siRNA, shRNA and antisense oligonucleotides used to target MADD mRNA transcripts were obtained from Dharmacon (Lafayette, Colo.) The most suitable sequences were sorted out based on less than 50% GC nucleotide content, high AU nucleotide content towards the 3' end and no inverted repeats within the siRNA region (Reynolds, et al. (2004) *Nat. Biotechnol.* 22(3):326-30).

An antisense oligonucleotide refers to a nucleic acid molecule which binds to target mRNA by means of RNA-RNA or RNA-DNA or RNA-PNA (peptide nucleic acid) interactions and alters the activity of the target mRNA. Typically, antisense molecules are complementary to a target sequence along a single contiguous sequence of the antisense molecule.

In another embodiment, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

In another aspect nucleic acid molecules or antisense molecules which interact with target RNA molecules and down-regulate MADD activity are expressed from transcription units inserted into DNA or RNA vectors. The recombinant vectors may be DNA plasmids or viral vectors. Enzymatic nucleic acid molecule or antisense expressing viral vectors can be constructed based on adeno-associated virus, retrovirus, adenovirus, or alphavirus. In an embodiment, the recombinant vectors capable of expressing the nucleic acid molecules are delivered as described herein, and persist in target cells. Alternatively, viral vectors can be used that provide for transient expression of shRNA/siRNA/antisense nucleic acid molecules. Such vectors can be repeatedly administered as necessary. After being expressed, the interfering nucleic acid molecules bind to the target RNA and down-regulate its function or expression. Delivery of nucleic acid molecule or antisense expressing vectors can be systemic, such as by intravenous or intramuscular administration, by administration to target cells explanted from the patient or subject followed by reintroduction into the patient or subject, or by any other means that would allow for introduction into the desired target cell. Antisense DNA can also be expressed via the use of a single stranded DNA intracellular expression vector.

siRNA and shRNA nucleic acid molecules and antisense oligonucleotides are designed accordingly based on the nucleotide sequence of the exon 13L of the MADD splice variant. Exon 13L of the MADD splice variant exhibits the nucleotide sequence such as that defined as nucleotides 2699 to 2827 of SEQ ID NO:11. The siRNA, shRNA and antisense oligonucleotides comprise oligonucleotides having a 19-base core nucleotide sequence which specifically targets exon 13L of the MADD splice variant. One skilled in the art may construct siRNA, shRNA and antisense oligonucleotides which comprise less than 50% GC nucleotide content, high AU nucleotide content towards the 3'-end and no inverted repeats, which oligonucleotides constitute an array of oligonucleotides which may span exon 13L nucleotide sequence. The siRNA, shRNA and antisense oligonucleotides may further comprise 2 or 3 nucleotide overhanging 3'-ends, such as a terminal TT to enhance cleavage destruction of the target mRNA. Often dTdT is selected because it can confer nuclease resistance to oligonucleotides. Moreover, UU overhangs or overhangs that are complementary to the authentic mRNA target may be added to the 19-base core of the oligonucleotides.

In an embodiment, the siRNA, shRNA and antisense oligonucleotide comprises a nucleic acid having the sequence GAUUGUCAUAGAUUCGCCGTT (SEQ ID NO:4). The siRNA and shRNA may be in the form of a duplex.

In an embodiment, the siRNA, shRNA and antisense oligonucleotide capable of down-regulating the expression of the MADD splice variant of an IG20 gene, wherein not all splice variants of the IG20 gene are down-regulated, comprises a nucleic acid having the sequence GAUUGUCAUAGAUUCGCCG (SEQ ID NO:10). The siRNA or shRNA may be in the form of a duplex.

In an embodiment, the siRNA, shRNA and antisense oligonucleotide capable of down-regulating the expression of the MADD splice variant of an IG20 gene, wherein not all splice variants of the IG20 gene are down-regulated, consists essentially of a nucleic acid having the sequence GAUUGUCAUAGAUUCGCCG (SEQ ID NO:10). The siRNA or shRNA may be in the form of a duplex.

The antisense oligonucleotide capable of down-regulating expression of at least one splice variant of the IG20 gene, wherein not all splice variants are down-regulated, may be a single-stranded nucleic acid molecule which exhibits a nucleic acid sequence which is complementary to the nucleic acid sequence, or a portion thereof, of exon 13L of the MADD splice variant and/or an mRNA transcript thereof. The single-stranded nucleic acid molecule may be in the form of RNA or DNA. In an embodiment, the antisense oligonucleotide comprises the sequence GAUUGUCAUAGAUUCGCCG (SEQ ID NO:10).

The term "analog" or "derivative" is used herein in the conventional pharmaceutical sense, to refer to a molecule which structurally resembles a reference molecule (such as protein kinase inhibitors, anthracyclines, nucleoside analogs, apoptosis-inducing molecular therapeutics or alkylating agents), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach which is well known in pharmaceutical chemistry.

Various salts and isomers (including stereoisomers and enantiomers) of the drugs listed herein may be used. The term "salts" can include addition salts of pharmaceutically acceptable free acids or free bases. Examples of acids which may be employed to form pharmaceutically acceptable acid addition salts include inorganic acids such as hydrochloric, sulfuric, or phosphoric acid, and organic acids such as acetic, maleic, succinic, or citric acid, etc. All of these salts (or other similar salts) may be prepared by conventional means. The nature of the salt or isomer is not critical, provided that it is non-toxic and does not substantially interfere with the desired pharmacological activity.

The term "therapeutically effective" applied to a dose or amount refers to that quantity of a compound or pharmaceutical composition which is sufficient to result in a desired activity upon administration to a mammal in need thereof. As used herein with respect to the pharmaceutical compositions comprising an siRNA, shRNA and antisense oligonucleotide capable of down-regulating the expression of the MADD splice variant of an IG20 gene and protein kinase inhibitors, the term "therapeutically effective amount/dose" is used interchangeably with the term "chemotherapeutically effective amount/dose" and refers to the amount/dose of a compound or pharmaceutical composition which is sufficient to produce an effective chemotherapeutic response upon administration to a mammal. Note that when a combination of active ingredients is administered the effective amount of the combination may or may not include amounts of each ingredient which are individually therapeutically effective.

The term "subthreshold" referring to the amount of an active ingredient means an amount inadequate to produce a response, i.e., an amount below the minimum effective amount. The term "suboptimal" in the same context means an amount of an active ingredient which produces a response but not to its full extent, which would be achieved with a higher amount. This methodology is particularly interesting in the instant context wherein the combination therapy described provides for the administration of "subthreshold" quantities of, for example, a protein kinase inhibitor, anthracycline, nucleoside analog, apoptosis-inducing molecular therapeutic or alkylating agent, wherein the administration is otherwise "subthreshold," but through the combination with siRNA, shRNA and antisense oligonucleotide capable of down-regulating the expression of the MADD splice variant of an IG20 gene, provides for otherwise fully effective treatment with the alleviation of unwanted side effects associated with the protein kinase inhibitor, anthracycline, nucleoside analog, apoptosis-inducing molecular therapeutic or alkylating agent.

The phrase "synergistic effect," "synergistic," "synergy," and "synergism," as used in connection with the combination therapy of the invention, refers to the cooperative action of two or more stimuli that when combined produce an effect which is greater than the sum of the effect of the contributions of each individual stimulus, i.e., more than an additive effect. The stimuli, for example, may be an agent which down-regulates expression of MADD and at least one therapeutic agent.

The phrase "pharmaceutically acceptable," as used in connection with compositions of the invention, refers to molecular entities and other ingredients of such compositions which are physiologically tolerable and do not typically produce untoward reactions when administered to a mammal (e.g., human). In an embodiment, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound (e.g., an siRNA, shRNA and antisense oligonucleotide capable of down-regulating the expression of the MADD splice variant of an IG20 gene and protein kinase inhibitors, anthracyclines, nucleoside analogs, apoptosis-inducing molecular therapeutics or alkylating agents) is administered. Such pharmaceutical carriers may be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Furthermore, suitable carriers may comprise liposomal formulations. Suitable pharmaceutical carriers may also be described in *Remington's Pharmaceutical Sciences* by E. W. Martin, 18$^{th}$ Edition.

The term "subject" as used herein refers to a mammal (e.g., rodent such as mouse or rat). In particular, the term refers to humans.

The term "about" or "approximately" usually means within 20%, within 10%, and optionally within 5% of a given value or range. Alternatively, especially in biological systems, the term "about" means within about a log (i.e., an order of magnitude) optionally within a factor of two of a given value.

The term "consisting of" excludes any element, step, or ingredient not specified in the claim. *In re Gray,* 53 F.2d 520, 11 USPQ 255 (CCPA 1931). The term "consisting essentially of" limits the scope of a claim to the specified materials or steps "and those that do not materially affect the basic and novel characteristic(s)" of the claimed invention. *In re Herz,* 537 F.2d 549, 551-52, 190 USPQ 461, 463 (CCPA 1976) (emphasis in original).

Protein Kinase Inhibitors

The term protein kinase inhibitor (PKI) is used herein to refer to a drug which exhibits an anti-cancer chemotherapeutic effect. The term encompasses eight protein kinase medications, including imatinib and gefinitib, have been approved by the Food and Drug Administration for use in humans. One tyrosine kinase inhibitor (TKI), toceranib, was recently approved for the treatment of cancer in dogs. The human medications may inhibit one or more kinases. Erlotinib, like gefitinib, inhibits EGFR. Lapatinib is a dual inhibitor of EGFR and a subclass called Human EGFR type 2. EGFR is not the only growth factor targeted. Sunitinib is multi-targeted, inhibiting PDGFR and VEGF.

Other kinase inhibitors are more specialized. Sorafenib targets a complex pathway that would lead to a kinase signaling cascade. Nilotinib inhibits the fusion protein bcr-abl and is typically prescribed when a patient has shown resistance to imatinib.

More protein kinase inhibitors are currently in development. Three protein kinase inhibitors are currently showing promise in clinical trials. Bosutinib targets abl and src kinases. Neratinib, like lapatinib, inhibits EGFR and Human EGFR type 2. Vatalanib inhibits both VEGFR and PDGFR, as well as other modifications and related derivatives known in the art.

Anthracyclines

The term anthracycline is used herein to refer to a drug which is used in the treatment of various solid tumors and hematological malignancies and exhibits an anti-cancer chemotherapeutic effect. Anthracyclines work by inhibiting DNA and RNA synthesis by intercalating between base pairs of the DNA/RNA strand and thereby, preventing the replication of rapidly dividing cancer cells. They also work by inhibiting topoisomerase II enzyme, thereby preventing the relaxing of supercoiled DNA and hence, blocking DNA transcription and replication. Anthracyclines are among the most commonly used chemotherapeutic agents. The effect of anthracyclines in treating cancer could be attributed to their cytostatic and cytotoxic actions such as free radical formation, lipid peroxidation and direct membrane effects. The best characterized mechanisms are the interactions with the DNA topoisomerase II or DNA itself via intercalation or covalent binding formation and modification of the bases, which are responsible for disturbances in DNA replication and transcription, eventually leading to induction of apoptotic cell death. The term encompasses daunorubicin, doxorubicin, epirubicin, idarubicin and valrubicin, as well as other modifications and related derivatives known in the art.

Nucleoside Analogs

The term nucleoside analog is used herein to refer to a drug which exhibits an anti-cancer chemotherapeutic effect. The term encompasses synthetic, chemically modified compounds that mimic their physiological counterparts and thereby, interfere with the synthesis of nucleic acids by incorporating into DNA and RNA. They can also interact and inhibit essential enzymes such as DNA-dependent DNA polymerase, RNA-dependent DNA polymerase, RNA-dependent RNA polymerase, kinases, DNA methyltransferases, pyrimidine and purine nucleoside phosphorylase etc.

Nucleoside analogues exert cytotoxic effect by being incorporated into and altering the DNA and RNA macromolecules themselves, by interfering with various enzymes involved in synthesis of nucleic acids, or by modifying the metabolism of physiological nucleosides.

Representative nucleoside analogues, such as gemcitabine, 5-fluorouracil and cytarabine, are used in the treatment of breast cancer, non-small cell lung cancer, pancreatic cancer, bladder cancer, biliary tract cancer and colon cancer, esophageal cancer, stomach cancer, cervical cancer, and other types of solid tumor cancers.

Apoptosis-Inducing Molecular Therapeutics

The term "apoptosis-inducing molecular therapeutic" is used herein to refer to a drug which induces apoptosis and exhibits an anti-cancer chemotherapeutic effect. The term encompasses protein molecules which play a role in regulating and directing the immune system. For cancer therapy, cytokines are synthesized and injected in larger does than the body normally produces. There are two common cytokines that are used in cancer immunotherapy, namely Interleukin 2 (IL2) and Interferon-α (IFN-α). In cancer treatment, IL2 is designed to target adaptive immune cells, T-cells and B-cells, to respond to tumors and IFN-α helps the body to generate innate immune cells, such as dendritic cells and macrophages that are designed to target the unhealthy cells. Tumor necrosis factor α-related apoptosis-inducing ligand (TRAIL) is a well-known cytotoxic protein which induces apoptosis in tumor cells, but not in normal cells.

Alkylating Agents

The term alkylating agent is used herein to refer to a drug which exhibits an anti-cancer chemotherapeutic effect. As used herein, alkylating agents act by attaching an alkyl group to the guanine base of DNA, thereby disrupting the normal functioning. Alkylating agents act by irreversibly binding to DNA. Once bound, the altered molecule leads to disruption of normal action and replication of DNA, ultimately leading to apoptosis or arrest of cellular replication. Therefore, upon treatment with alkylating agents, they can limit tumor growth and lead to tumor destruction. The term encompasses alkylating agents which can be classified as classical alkylating agents such as cyclophosphamide, mechlorethane; alkylating-like agents such as cisplatin, carboplatin; and agents such as procarbazine, ifosfamide, melphalan, chlorambucil, cyclophosphamide, streptozocin, carmustine, lomustine, busulfan, and dacarbazine.

Pharmaceutical Compositions

In conjunction with the methods of the present invention, also provided are pharmaceutical compositions comprising a therapeutically effective amount of an siRNA, shRNA and antisense oligonucleotide capable of down-regulating the expression of the MADD splice variant of an IG20 gene and/or a therapeutically effective amount of a chemotherapeutic disclosed herein as well as, optionally, an additional carrier or excipient (all pharmaceutically acceptable). Said siRNA, shRNA and antisense oligonucleotide capable of down-regulating the expression of the MADD splice variant of an IG20 gene and chemotherapeutic may be either formulated as a single composition or as two separate compositions, which may be administered conjointly. In an embodiment, they are formulated as a single composition or as two separate compositions, which are optionally administered sequentially or simultaneously. The compositions may be formulated for once-a-day administration or twice-a-day administration, as well as dosage regimens typical in the respective therapies.

In a further embodiment, the instant combinations may be formulated such that they may be administrated in a titration regimen such that the patient may acclimate to the effects of the chemotherapeutic (i.e., protein kinase inhibitor, anthracycline, nucleoside analog, apoptosis-inducing molecular therapeutic or alkylating agent) and/or the clinician may titrate up the siRNA, shRNA and antisense oligonucleotide capable of down-regulating the expression of the MADD splice variant of an IG20 gene so that the chemotherapeutic may be down titrated to significantly lower dosages so as to minimize toxic side effects of the chemotherapeutic and/or accommodate for dosing difficulties associated with the chemotherapeutic.

In the disclosed compositions, optionally, both the siRNA, shRNA and antisense oligonucleotide capable of down-regulating the expression of the MADD splice variant of an IG20 gene and chemotherapeutic(s) are present in therapeutically effective amounts. The optimal therapeutically effective amount should be determined experimentally, taking into consideration the exact mode of administration, form in which the drug is administered, the indication toward which the administration is directed, the subject involved (e.g., body weight, health, age, sex, etc.), and the preference and experience of the physician or veterinarian in charge. As disclosed herein, for human administration, both the siRNA, shRNA and antisense oligonucleotide capable of down-regulating the expression of the MADD splice variant of an IG20 gene and chemotherapeutics are administered in suitable form in doses ranging from those understood in the art. In an embodiment, the siRNA, shRNA and antisense oligonucleotide capable of down-regulating the expression of the MADD splice variant of an IG20 gene are administered at therapeutic doses; the chemotherapeutics are administered at suboptimal or lowered doses. It may also be desirable in certain cases to administer one or the other of the active ingredients in a suboptimal or subthreshold amount, and such administration would also be within the scope of the invention.

The invention also provides a method for preparing pharmaceutical compositions comprising admixing an siRNA, shRNA and antisense oligonucleotide capable of down-regulating the expression of the MADD splice variant of an IG20 gene and chemotherapeutics (i.e., protein kinase inhibitors, anthracyclines, nucleoside analogs, apoptosis-inducing molecular therapeutics or alkylating agents) in therapeutically effective amounts, and optionally one or more physiologically acceptable carriers and/or excipients and/or auxiliary substances.

Administration

The active agents of the present invention may be administered intradermally, parenterally, intranasally or intratumorally in dosage unit formulations containing conventional non-toxic pharmaceutically acceptable carriers with or without a targeting molecule which would selectively deliver the active agent to a particular cell type or tissue. The intradermal administration could involve using transdermal patches, microabrasion or nanoemulsions. The parenterally administered medicaments may be administered in the form of an injection, a time-controlled release vehicle, including diffusion-controlled systems, osmotic devices, dissolution-controlled matrices, and erodible/degradable matrices.

For oral administration in the form of a tablet or capsule, the active drug component may be combined with non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethylene glycol, waxes, and the like. For oral administration in liquid form, the drug components may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms.

The tablets may be coated by methods well known in the art. The compositions of the invention may be also introduced in microspheres or microcapsules, e.g., fabricated from polyglycolic acid/lactic acid (PGLA) (see, e.g., U.S. Pat. Nos. 5,814,344; 5,100,669; 4,849,222; WO 1995/11010 and WO 1993/07861). Liquid preparations for oral administration can take the form of, for example, solutions, syrups, emulsions or suspensions, or they may be presented as a dry product for reconstitution with water or other suitable vehicle before use. Preparations for oral administration may be suitably formulated to give controlled or postponed release of the active compound.

Drug delivery systems known in the art are specialized technologies for the targeted delivery and/or controlled release of therapeutic agents.

The drug delivery systems deploy medications intact to specifically targeted parts of the body through a medium that can control the therapy's administration. Such drug delivery systems may include micro- and nanotechnology.

The nucleic acid molecules capable of down-regulating expression of the at least one splice variant of the IG20 gene selected from siRNA, shRNA and antisense oligonucleotides complementary to the nucleotide sequence the MADD splice variant of the IG20 gene mRNA transcript, may be incorporated into drug delivery systems known in the art and which may include polymeric microspheres, polymer micelles, and hydrogel-type materials, which drug delivery systems are understood in the art to be effective in enhancing drug targeting specificity, lowering systemic toxicity, improving treatment absorption rates, and providing protection for pharmaceuticals against biochemical degradation. In addition, several other drug delivery systems are contemplated, including biodegradable polymers, dendrimers (so-called star polymers), electroactive polymers, and modified C-60 fullerenes (also known as "buckyballs").

Moreover, drug delivery systems may include lentivirus-mediated transduction of nucleic acids encoding nucleic acid molecules capable of down-regulating expression of the at least one splice variant of the IG20 gene are selected from siRNA, shRNA and antisense oligonucleotides complementary to the nucleotide sequence the MADD splice variant of the IG20 gene mRNA transcript.

The active drugs can also be administered in the form of liposome delivery systems, such as small unilamellar vesicles, large unilamellar vesicles and multilamellar vesicles. Liposomes may be formed from a variety of phospholipids, such as cholesterol, stearylamine or phosphatidylcholines, as is well known.

The siRNA, shRNA and antisense oligonucleotide capable of down-regulating the expression of the MADD splice variant of an IG20 gene may be bound in the form of a targeted liposome formulation. Representative assemblies may include encapsulation within self-assembled engineered proteins which provide for efficient packaging, binding, assembly and delivery of such oligonucleotides. The constituents of such engineered proteins may be selected from peptides which actively target tumor cells through attachment to selected cell surface receptors, peptides which facilitate receptor-mediated endocytosis and peptides which provide for active release of the transported oligonucleotides. Such self-assembled protein transport molecules, comprising the oligonucleotides of the instant invention, may be assembled in the form of nanoparticles (<50 nm) comprising two components: the engineered polypeptide (targeting peptide, membrane penetration peptide, oligonucleotide capturing peptide) and the oligonucleotide therapeutic payload.

Drugs of the invention may also be delivered by the use of monoclonal antibodies as individual carriers to which the compound molecules are coupled. Active drugs may also be coupled with soluble polymers as targetable drug carriers. Such polymers can include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the therapeutics according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The formulations of the invention may be delivered parenterally, i.e., by intravenous (i.v.), intracerebroventricular (i.c.v.), subcutaneous (s.c.), intraperitoneal (i.p.), intramuscular (i.m.), subdermal (s.d.), intratumoral (i.t.) or intradermal (i.d.) administration, by direct injection, via, for example, bolus injection or continuous infusion. Formulations for injection may be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient may be in powder form for reconstitution with a suitable vehicle, e.g., sterile pyrogen-free water, before use.

Compositions of the present invention can also be formulated for rectal administration, e.g., as suppositories or retention enemas (e.g., containing conventional suppository bases such as cocoa butter or other glycerides).

As disclosed herein, siRNA, shRNA and antisense oligonucleotide capable of down-regulating the expression of the MADD splice variant of an IG20 gene and chemotherapeutics may be mixed with excipients which are pharmaceutically acceptable and compatible with the active ingredients. In addition, if desired, the preparations may also include minor amounts of auxiliary substances such as wetting or emulsifying agents, pH buffering agents, and/or agents which enhance the effectiveness of the pharmaceutical composition. These auxiliary molecules may be delivered systemically or locally as proteins or by expression of a vector which codes for expression of the molecule. The techniques described above for the delivery of siRNA, shRNA and antisense oligonucleotide capable of down-regulating the expression of the MADD splice variant of an IG20 gene and chemotherapeutics can also be employed for the delivery of auxiliary molecules.

Although the active agents of the present invention may be administered in divided doses, for example, two or three times daily, a single daily dose of each of the siRNA, shRNA and antisense oligonucleotide capable of down-regulating the expression of the MADD splice variant of an IG20 gene and chemotherapeutics, with a single daily dose of both agents in one composition or in two separate compositions administered simultaneously is an embodiment.

The instant invention also encompasses a process for preparing pharmaceutical compositions comprising combining siRNA, shRNA and antisense oligonucleotides capable of down-regulating the expression of the MADD splice variant of an IG20 gene and chemotherapeutics with a pharmaceutically acceptable carrier and/or excipient.

Specific amounts of the siRNA, shRNA and antisense oligonucleotide capable of down-regulating the expression of the MADD splice variant of an IG20 gene which may be used in unit dosage amounts of the invention may be readily ascertainable to those skilled in the art. Specific amounts of the chemotherapeutic which may be used in reduced unit dosage amounts of the invention include, for example, the chemotherapeutic used at ¾, ½, $⅓^{rd}$, $¼^{th}$, $⅕^{th}$ $1/10^{th}$ $1/20^{th}$ of the recommended dose.

The invention also provides a pharmaceutical pack or kit comprising one or more containers containing one or more of the ingredients of the formulations of the invention. In a related embodiment, the present invention provides a kit for the preparation of the pharmaceutical compositions of the invention, said kit comprising a formulation of one or more siRNA, shRNA and antisense oligonucleotide capable of down-regulating the expression of the MADD splice variant of an IG20 gene in a first container or multiple containers, and one or more protein kinase inhibitor, anthracycline, nucleoside analog, apoptosis-inducing molecular therapeutic or alkylating agent in a second container or multiple containers, and, optionally, instructions for admixing the two drugs and/or for administration of the drugs in therapeutically meaningful regimens. Each container of the kit may also optionally include one or more physiologically acceptable carriers and/or excipients and/or auxiliary substances. Associated with such container(s) may be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

Effective Dose and Safety Evaluations

According to the methods of the present invention, the pharmaceutical compositions described herein are administered to a patient at therapeutically effective doses, in an embodiment, with minimal toxicity other than required for the therapeutic purpose of the combination. The Section entitled "Definitions" provides definitions for the terms "chemotherapeutically effective dose" and "therapeutically effective dose". In an embodiment, the siRNA, shRNA and antisense oligonucleotide capable of down-regulating the expression of the MADD splice variant of an IG20 gene and protein kinase inhibitors, anthracyclines, nucleoside analogs, apoptosis-inducing molecular therapeutics or alkylating agents are each used at a dosage which, when combined, provide an enhanced effect, for example, an effect not observed upon administration of each agent alone. It is an embodiment of the instant invention that both the siRNA, shRNA and antisense oligonucleotide capable of down-regulating the expression of the MADD splice variant of an IG20 gene and protein kinase inhibitors, anthracyclines, nucleoside analogs, apoptosis-inducing molecular therapeutics or alkylating agents are administered at "suboptimal" or "subthreshold" doses, which doses, in combination, provide for a super-additive effect with surprising reduction in unwanted side effects.

The efficacy of the siRNA, shRNA and antisense oligonucleotide capable of down-regulating the expression of the MADD splice variant of an IG20 gene of the invention may be determined using such in vitro pharmacological tests such as measurements of the levels of mRNA using quantitative Reverse Transcriptase-Polymerase Chain Reaction (Q-RT-PCR) or RT-PCR, etc. The efficacy of the chemotherapeutics of the invention may be determined in vitro using methods known to those skilled in the art, for example, cell cytotoxicity assays, MTT assay, apoptosis assays, cell migration assays, etc.

Following methodologies which are well-established in the art, effective doses and toxicity of the compounds and compositions of the instant invention, which perform well in in vitro tests, may then be determined in preclinical studies using small animal models (e.g., mice or rats) in which both the siRNA, shRNA and antisense oligonucleotide capable of down-regulating the expression of the MADD splice variant of an IG20 gene and protein kinase inhibitors, anthracyclines, nucleoside analogs, apoptosis-inducing molecular therapeutics or alkylating agents have been found to be therapeutically effective.

For any pharmaceutical composition used in the methods of the invention, the therapeutically effective dose may be estimated initially from animal models to achieve a circulating plasma concentration range which includes the $IC_{50}$ (i.e., the concentration of the test compound which achieves a half-maximal). Dose-response curves derived from animal systems may then be used to determine testing doses for the initial clinical studies in humans. In safety determinations for each composition, the dose and frequency of administration should meet or exceed those anticipated for use in the clinical trial.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions may be determined by the test based on the above-described indices but may be refined and ultimately decided according to the judgment of the practitioner and each patient's circumstances (age, general condition, severity of symptoms, sex, etc.) according to standard clinical techniques. As disclosed herein, an appropriate dose of an siRNA, shRNA and antisense oligonucleotide capable of down-regulating the expression of the MADD splice variant of an IG20 gene is generally ascertainable to those skilled in the art, and an appropriate dose of protein kinase inhibitor, anthracycline, nucleoside analog, apoptosis-inducing molecular therapeutic or alkylating agent is generally ascertainable to those skilled in the art. In an embodiment, the dosage of siRNA to be administered may range from 1 to 10 mg per kilogram of body weight. The dosage may vary within this range depending upon the dosage form employed and the route of administration utilized. In an embodiment, a single dose of each drug may be administered daily.

Toxicity and therapeutic efficacy of the compositions of the invention may be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $ED_{50}/LD_{50}$. Formulations/combinations which exhibit large therapeutic indices are preferred.

The data obtained from animal studies may be used in formulating a range of doses for use in humans. The therapeutically effective doses of siRNA, shRNA and antisense oligonucleotide capable of down-regulating the expression of the MADD splice variant of an IG20 gene and protein kinase inhibitors, anthracyclines, nucleoside analogs, apoptosis-inducing molecular therapeutics or alkylating agents in humans lay within a range of circulating concentrations which include the $ED_{50}$ with little or no toxicity other than therapeutically necessary. For example, such therapeutically effective circulating concentration for siRNA, shRNA and antisense oligonucleotide capable of down-regulating the expression of the MADD splice variant of an IG20 gene generally ascertainable to those skilled in the art. The dosage of siRNA, shRNA and antisense oligonucleotide capable of down-regulating the expression of the MADD splice variant of an IG20 gene to be administered may range from 1 to 10 mg per kilogram of body weight. The dosage can vary within this range depending upon the dosage form employed and the route of administration utilized. Ideally, a single dose of each drug should be used daily.

The drug combination of the invention is not only highly effective at relatively low doses but also possesses low toxicity other than therapeutically necessary and produces few side effects. Indeed, the only common side effects for the chemotherapeutics of the invention are those for which the instant combination therapy has been designed to alleviate, while the most common side effect resulting from the use of siRNA, shRNA and antisense oligonucleotide capable of down-regulating the expression of the MADD splice variant of an IG20 gene of the invention is that associated with injection of RNA such as transient heightened inflammatory response including increased interferon production.

Pharmacology—Summary

The active principles of the present invention, and pharmaceutical compositions thereof and method of treating therewith, are characterized by unique advantageous and unpredictable properties, rendering the "subject matter as a whole," as claimed herein, unobvious. The combinations and pharmaceutical compositions thereof exhibit, in standard accepted reliable test procedures, the following valuable properties and characteristics.

The results demonstrate a synergistic effect of the combination of siRNA knockdown of MADD and Sorafinib treatment on the cell death of pancreatic cancer cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of lung cancer cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of thyroid cancer cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of hepatic cancer cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of lung cancer cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of chronic myelogenous leukemia cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of gastric adenocarcinoma cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Sorafinib treatment on the cell death of ovarian cancer cells, wherein the amount of cell death from the combination of siRNA knockdown of MADD and Sorafinib treatment exceeds the additive effect of monotherapy with either MADD siRNA knockdown or Sorafinib monotherapy.

The results demonstrate a synergistic effect of the combination of siRNA knockdown of MADD and Doxorubicin treatment on the cell death of pancreatic cancer cells, wherein the amount of cell death from the combination of siRNA knockdown of MADD and Doxorubicin treatment exceeds the additive effect of monotherapy with either MADD siRNA knockdown or Doxorubicin monotherapy.

The results demonstrate a synergistic effect of the combination of siRNA knockdown of MADD and Doxorubicin treatment on the cell death of lung cancer cells, wherein the amount of cell death from the combination of siRNA knockdown of MADD and Doxorubicin treatment exceeds the additive effect of monotherapy with either MADD siRNA knockdown or Doxorubicin monotherapy.

The results demonstrate a synergistic effect of the combination of siRNA knockdown of MADD and Doxorubicin treatment on the cell death of breast cancer cells, wherein the amount of cell death from the combination of siRNA knockdown of MADD and Doxorubicin treatment exceeds the additive effect of monotherapy with either MADD siRNA knockdown or Doxorubicin monotherapy.

The results demonstrate a synergistic effect of the combination of siRNA knockdown of MADD and Doxorubicin treatment on the cell death of gastric carcinoma cells, wherein the amount of cell death from the combination of siRNA knockdown of MADD and Doxorubicin treatment exceeds the additive effect of monotherapy with either MADD siRNA knockdown or Doxorubicin monotherapy.

The results demonstrate a synergistic effect of the combination of siRNA knockdown of MADD and Doxorubicin treatment on the cell death of chronic myelogenous leukemia cells, wherein the amount of cell death from the combination of siRNA knockdown of MADD and Doxorubicin treatment exceeds the additive effect of monotherapy with either MADD siRNA knockdown or Doxorubicin monotherapy.

The results demonstrate a synergistic effect of the combination of siRNA knockdown of MADD and Gemcitabine treatment on the cell death of lung cancer cells, wherein the amount of cell death from the combination of siRNA knockdown of MADD and Gemcitabine treatment exceeds the additive effect of monotherapy with either MADD siRNA knockdown or Gemcitabine monotherapy.

The results demonstrate a synergistic effect of the combination of siRNA knockdown of MADD and Gemcitabine treatment on the cell death of hepatic cancer cells, wherein the amount of cell death from the combination of siRNA knockdown of MADD and Gemcitabine treatment exceeds the additive effect of monotherapy with either MADD siRNA knockdown or Gemcitabine monotherapy.

The results demonstrate a synergistic effect of the combination of siRNA knockdown of MADD and Gemcitabine treatment on the cell death of ovarian cancer cells, wherein the amount of cell death from the combination of siRNA knockdown of MADD and Gemcitabine treatment exceeds the additive effect of monotherapy with either MADD siRNA knockdown or Gemcitabine monotherapy.

The results demonstrate a synergistic effect of the combination of siRNA knockdown of MADD and Gemcitabine treatment on the cell death of gastric adenocarcinoma cells, wherein the amount of cell death from the combination of siRNA knockdown of MADD and Gemcitabine treatment exceeds the additive effect of monotherapy with either MADD siRNA knockdown or Gemcitabine monotherapy.

The results demonstrate a synergistic effect of the combination of siRNA knockdown of MADD and 5-flurouracil treatment on the cell death of gastric adenocarcinoma cells, wherein the amount of cell death from the combination of siRNA knockdown of MADD and 5-flurouracil treatment exceeds the additive effect of monotherapy with either MADD siRNA knockdown or 5-flurouracil monotherapy.

The results demonstrate a synergistic effect of the combination of siRNA knockdown of MADD and TRAIL treatment on the cell death of ovarian cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of lung cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of thyroid cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of hepatic cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of colon cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of chronic myelogenous leukemia cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of gastric adenocarcinoma cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and TRAIL treatment on the cell death of pancreatic cancer cells, wherein the amount of cell death from the combination of siRNA knockdown of MADD and TRAIL treatment exceeds the additive effect of monotherapy with either MADD siRNA knockdown or TRAIL monotherapy.

The results demonstrate a synergistic effect of the combination of siRNA knockdown of MADD and Cisplatin treatment on the cell death of thyroid cancer cells, wherein the amount of cell death from the combination of siRNA knockdown of MADD and Cisplatin treatment exceeds the additive effect of monotherapy with either MADD siRNA knockdown or Cisplatin monotherapy.

The results demonstrate a synergistic effect of the combination of siRNA knockdown of MADD and Cisplatin treatment on the cell death of hepatic cancer cells, wherein the amount of cell death from the combination of siRNA knockdown of MADD and Cisplatin treatment exceeds the additive effect of monotherapy with either MADD siRNA knockdown or Cisplatin monotherapy.

The following non-limiting examples are provided to further illustrate the present invention.

Example 1: Determination of Chemotherapeutic Cytotoxicity Dosage Curves

Cancer cell lines representative of various cancers which may be susceptible to protein kinase inhibitor treatment include 8505C (thyroid carcinoma), HTH7 (thyroid carcinoma), C643 (human thyroid carcinoma), AsPC-1 (pancreatic cancer), SU.86.86 (pancreatic cancer), CFPAC-1 (pancreatic cancer), MCF7 (adenocarcinoma breast cancer), SK-BR-3 (breast cancer), OVCAR3 (ovarian cancer), SKOV3 (ovarian cancer), NCI-H522 (non-small cell lung cancer), NCI-H2122 (non-small cell lung cancer), NCI-H2227 (small cell lung cancer), HepG2 (liver hepatocellular carcinoma), PLC/PRF/5 (liver hepatoma), AGS (gastric adenocarcinoma), JIMT1 (breast cancer), HCT-116 (colon cancer) and K562 (chronic myelogenous leukemia). Cell lines may be obtained from the National Cancer Institute, Bethesda, Md. or American Type Culture Collection, or similar organizations in other countries. These cell lines may be selected because they all express higher levels of the MADD splice variant, are derived from different types of cancers, all which are in need of new modalities of treatment, exhibit unique growth properties and have differential susceptibility to different modalities of treatment with chemotherapeutic agents due to underlying different mutations. In spite of their heterogeneity, these cell lines may be rendered susceptible to therapeutic treatment upon MADD knockdown, and thus show the potential beneficial effects of MADD knockdown in a range of different cancers. Because of their unique growth properties these cell lines are cultured in culture media which have been formulated to support their optimum growth in culture.

8505C cells are cultured in RPMI-1640 culture medium and supplemented with 10% fetal bovine serum and 1% penicillin/streptomycin.

HTH7 cells are cultured in RPMI-1640 culture medium and supplemented with 10% fetal bovine serum and 1% penicillin/streptomycin.

C643 cells are cultured in RPMI-1640 culture medium and supplemented with 10% fetal bovine serum and 1% penicillin/streptomycin.

AsPC-1 cells are cultured in RPMI-1640 medium modified to contain 2 mM L-glutamine, 10 mM HEPES, 1 mM sodium pyruvate, 4500 mg/L glucose, and 1500 mg/L sodium bicarbonate, for use in incubators using 5% $CO_2$ in air. Additional sodium bicarbonate may be required for use in incubators containing higher percentages of $CO_2$. Base medium is supplemented with 10% fetal bovine serum and antibiotics and anti-mycotic agents.

SU.86.86 cells are cultured in RPMI-1640 medium modified to contain 2 mM L-glutamine, 10 mM HEPES, 1 mM sodium pyruvate, 4500 mg/L glucose, and 1500 mg/L sodium bicarbonate, for use in incubators using 5% $CO_2$ in air. Additional sodium bicarbonate may be required for use in incubators containing higher percentages of $CO_2$. Base medium is supplemented with 10% fetal bovine serum and antibiotics and anti-mycotic agents.

CFPAC-1 cells are cultured in Iscove's Modified Dulbecco's Medium (IMDM) containing 4 mM L-glutamine, 4500 mg/L glucose, and 1500 mg/L sodium bicarbonate. This base medium is supplemented with 10% fetal bovine serum and antibiotics and anti-mycotic agents.

MCF7 cells are cultured in Eagle's minimum essential medium modified to contain Earle's Balanced Salt Solution, non-essential amino acids, 2 mM L-glutamine, 1 mM sodium pyruvate, and 1500 mg/L sodium bicarbonate. This base medium is supplemented with 0.01 mg/ml human recombinant insulin; fetal bovine serum to a final concentration of 10%.

SK-BR-3 cells are cultured in McCoy's 5A Medium modified to contain 1.5 mM L-glutamine and 2200 mg/L sodium bicarbonate. This base medium is supplemented with 10% fetal bovine serum and antibiotics and anti-mycotic agents.

OVCAR3 cells are cultured in RPMI-1640 medium modified to contain 2 mM L-glutamine, 10 mM HEPES, 1 mM sodium pyruvate, 4500 mg/L glucose, and 1500 mg/L sodium bicarbonate, for use in incubators using 5% $CO_2$ in air. This base medium is supplemented with 0.01 mg/ml bovine insulin, antibiotic and anti-mycotic agents and fetal bovine serum to a final concentration of 20%.

SKOV3 cells are cultured in McCoy's 5A Medium is modified to contain 1.5 mM L-glutamine and 2200 mg/L sodium bicarbonate. This base medium is supplemented with 10% fetal bovine serum and antibiotics and anti-mycotic agents.

NCI-H522 cells are cultured in RPMI-1640 medium modified to contain 2 mM L-glutamine, 10 mM HEPES, 1 mM sodium pyruvate, 4500 mg/L glucose, and 1500 mg/L sodium bicarbonate, for use in incubators using 5% $CO_2$ in air. This base medium is supplemented with 10% fetal bovine serum and antibiotics and anti-mycotic agents.

NCI-H2122 cells are cultured in RPMI-1640 medium modified to contain 2 mM L-glutamine, 10 mM HEPES, 1 mM sodium pyruvate, 4500 mg/L glucose, and 1500 mg/L sodium bicarbonate, for use in incubators using 5% $CO_2$ in air. This base medium is supplemented with 10% fetal bovine serum and antibiotics and anti-mycotic agents.

NCI-H2227 cells are cultured in DMEM:F12 Medium containing 0.005 mg/ml Insulin, 0.01 mg/ml Transferrin, 30 nM Sodium selenite, 10 nM Hydrocortisone, 10 nM beta-estradiol, extra 2 mM L-glutamine (for final conc. of 4.5 mM), 5% fetal bovine serum.

HepG2 cells are cultured in Eagle's Minimum Essential Medium (EMEM) and supplemented with 10% fetal bovine serum and 1% penicillin/streptomycin.

PLC/PRF/5 cells are cultured in Eagle's Minimum Essential Medium (EMEM) and supplemented with 10% fetal bovine serum and 1% penicillin/streptomycin.

K562 cells are cultured in Iscove's Modified Dulbecco's Medium (IMDM) and supplemented with 10% fetal bovine serum and 1% penicillin/streptomycin.

HCT116 cells are cultured in RPMI-1640 medium, supplemented with 10% fetal bovine serum and 1% penicillin/streptomycin.

AGS cells are cultured in RPMI-1640 medium, supplemented with 10% fetal bovine serum and 1% penicillin/streptomycin.

JIMT1 cells were cultured in complete RPMI media (GIBCO) with 10% fetal bovine serum and 1× Antibiotic-Antimycotic solution (Gibco). The Antibiotic-Antimycotic solution contains 10,000 units/mL of penicillin, 10,000 μg/mL of streptomycin, and 25 μg/mL of Gibco Amphotericin B.

N87 cells are cultured in RPMI-1640 medium, supplemented with 10% fetal bovine serum and 1% penicillin/streptomycin.

All cell lines are maintained at 37° C. in a humidified atmosphere with 5% $CO_2$.

Chemotherapeutics may be obtained commercially as FDA-approved drugs from pharmacies with a doctor's prescription.

All cells are cultured in their respective culture medium with appropriate supplements as described above.

TABLE 1

| Overview of Protocol - Adherent cell lines | |
|---|---|
| Day 0 | Cell seeding in 96 well plates |
| Day 1 | Chemotherapeutic drug addition |
| Day 2 | Cell viability analysis/MTT assay for 24 h |
| Day 3 | Cell viability analysis/MTT assay for 48 h |

TABLE 2

| Overview of Protocol - Suspension cell line | |
|---|---|
| Day 0 | Cell seeding and chemotherapeutic drugs addition in 96 well plates |
| Day 1 | MTT assay, followed by addition of equal volume of solubilization agent (20% SDS in 50% Dimethylformamide) and overnight incubation |
| Day 2 | Cell viability analysis for 24 h |
| Day 3 | Cell viability analysis for 48 h |

On Day 0, adherent cells are seeded in 96-well plates (Corning; Cat number: 353072) and incubated overnight.

On Day 0, suspension cells are seeded in 96-well plates (Corning; Cat number: 353072) along with the chemotherapeutics.

After overnight incubation (Day 1), six different concentrations of each chemotherapeutic drug are added in triplicates.

The working concentrations of the chemotherapeutics analyzed are provided in Table 3.

TABLE 3

| Drugs | Working Concentrations |
|---|---|
| Sorafinib | 0.3125 μM, 0.375 μM, 0.625 μM, 0.975 μM, 1.25 μM, 1.56 μM, 3 μM, 5 μM |
| Gemcitabine | 8.2 nM, 12.5 nM, 25 nM, 31.25 nM, 0.1 μM, 25 μM |
| 5-flurouracil | 25 μM |
| TRAIL | 6.25 ng/ml, 12.5 ng/ml, 50 ng/ml, 100 ng/ml |
| Cisplatin | 1.25 μM, 1.875 μM, 2.5 μM, 5 μM |

Stock solutions of Sorafinib are prepared in DMSO. Stock solutions of Gemcitabine are prepared in DMSO. Stock solutions of TRAIL are prepared in cell culture grade water. Stock solutions of Cisplatin are prepared in DMSO. Working concentrations of these drugs are prepared in the culture medium. Working concentrations of these drugs are prepared in the culture medium.

Cytotoxicity of the respective cell line models may be evaluated based on the compared cytotoxicity as measured utilizing the MTT assay.

MTT Straining for Metabolic Activity.

MTT (3-[4,5-Dimethylthiazol-2-yl]-2,5-diphenyltetrazolium bromide; Thiazolyl blue) may be purchased from Sigma Aldrich (Cat number: M5655) and dissolved in sterile DPBS at a concentration of 5 mg/ml.

In adherent cells, after 24 and 48 hours of drug exposure (Days 2 and 3 respectively), 10 μl of prepared MTT solution is added per well of a 96-well plate. Plates are incubated for 2 hours at 37° C. in the humidified $CO_2$ incubator. After 2 hours, media is aspirated using vacuum inside the biosafety hood. Purple colored formazan crystals which form in viable cells are dissolved by adding 100 μl of Dimethyl sulfoxide (Thermo Fisher Scientific; Cat number D128-500). Plates are kept on shaker for 10 minutes for compete dissolution of crystals and absorbance is recorded at 595 nm using Bio-Rad iMark microplate reader.

In suspension cells, after 24 and 48 hours of drug exposure (Days 1 and 2 respectively), 10 μl of prepared MTT solution is added per well of a 96-well plate. Plates are incubated for 2 hours at 37° C. in the humidified $CO_2$ incubator. After 2 hours incubation, equal volume of solubilization agent (20% SDS in 50% Dimethylformamide) is added and the plates are incubated overnight at 37° C. in the humidified $CO_2$ incubator. After overnight incubation, plates are kept on shaker for 10 minutes for compete dissolution of crystals and absorbance is recorded at 595 nm using Bio-Rad iMark microplate reader.

Percent cell survival is calculated using MICROSOFT EXCEL®. GraphPad prism software is used to calculate $EC_{50}$. The MTT assay indicates the overall cell death.

The studies demonstrate that treatment of cancer cells with a protein kinase inhibitor chemotherapeutic, anthracycline chemotherapeutic, nucleoside analog chemotherapeutic, apoptosis-inducing molecular therapeutic, or alkylating agent exhibits a dose response profile measurable based on the death of the cancer cells.

Example 2: Map Kinase Activating Death Domain Containing Protein (MADD) siRNA Transfection siRNA, shRNA and/or antisense oligonucleotides comprising nucleic acid molecules which target exon 13L of the MADD splice variant may be designed. siRNAs comprising a central 19 bp duplex with 2-base 3'-overhangs are synthesized. Moreover, a non-specific Scramble siRNA having a 19 bp duplex with 2-base 3'-overhangs is synthesized to provide a negative control siRNA. The sequences of siRNAs (double stranded duplex) used are:

```
MADD siRNA:
                                        (SEQ ID NO: 4)
5'-GAUUGUCAUAGAUUCGCCGTT-3'

Scramble siRNA:
                                        (SEQ ID NO: 5)
5'-UUGCUAAGCGUCGGUCAAUTT-3'
```

Transfection mediating reagent sold under the trademark LIPOFECTAMINE® RNAimax is a cationic unilamellar liposomal structure with a positive surface charge in water. The lipid cationic charges interact with negative phosphate groups of nucleic acids in siRNA and forms a liposome/siRNA transfection complex with the cell membrane. This complex can easily fuse with a cell membrane and siRNA is delivered inside the cell via endocytosis.

Dosing of siRNA and transfection reagents needs to be determined for each cell line. The manufacturer's recommended volume of transfection reagent per $mm^3$ area of tissue culture plate is used, generally, and the siRNA concentration may vary. For most cells, 10 nM of siRNA is sufficient to cause MADD knock-down within 48 hours of transfection.

Transfection. Cells are cultured and maintained in a humidified atmosphere containing 5% $CO_2$ in ATCC recommended media with 10% fetal bovine serum (Gibco; Cat number 26140-079) and 1× anti-biotic/anti-mycotic (Gibco; Cat number:15240096) at 37° C., 5% $CO_2$ incubator. For transfection, cells are seeded in to 96-well plates (24 hours before transfection to reach 60-80% confluence). The details of the transfection reaction for each cell line tested is given below.

Transfection reaction mix is prepared as recommended by manufacturer's instructions in triplicate. Briefly, an aliquot of a 100 μM siRNA stock solution is diluted in 5 μl culture medium sold under the trademark OPTI-MEM® in tube A to give a final concentration of 10 nM siRNA per well. RNAiMax reagent (0.3 μl; Thermo Fisher Scientific) is mixed in 4.7 μl culture medium sold under the trademark OPTI-MEM® in tube B. Contents from tube A and B are mixed and incubated for 15 minutes at room temperature. Reaction mix is added to the plates and incubated for 24 hours, 48 hours and 72 hours at 37° C. Media is changed after 48 hours.

RNA Isolation.

Total RNA is extracted using extraction reagent sold under the trademark TRIZOL® (Ambion; Cat number: 15596018). For each well of 96-well plate, 150 μl of extraction reagent sold under the trademark TRIZOL® is added to suspend and homogenize the cell suspension. Triplicate samples are pooled together for further processing. Cells are incubated for 10 minutes at room temperature. Chloroform (250 μl, Fisher; Cat number: C606-1) is added to the cell suspension. Samples are incubated at room temperature for 3 minutes. Tubes are centrifuged at 10,000 rpm for 15 minutes at 4° C. The top layer is transferred to a fresh tube and 600 μl of isopropanol (Fisher; Cat number: A451-1) is added. The tube is incubated at room temperature for 10 minutes. The tube is subsequently centrifuged at 10,000 rpm for 10 minutes at 4° C. Supernatant is discarded and the pellet is washed with 1 ml of 75% ethanol (Decon; Cat number: DSP-AZ-1). The tube is again centrifuged at 7500 rpm for 5 minutes at 4° C. The pellet is air dried and dissolved in 20 μl of DEPC water (Fisher; Cat number: BP561-1). RNA is quantified by using Thermo Fisher Scientific NanoDrop One. A260/280 and A260/230 are used to validate the purity of sample.

Reverse-Transcriptase PCR.

For RT-PCR, MADD and β-actin (internal loading control) primers are used. The sequences of primers used are:

```
MADD 13L Forward:
                                    (SEQ ID NO: 6)
5'-AGCCCCAATATGGCTTTCCC-3'

MADD 13L Reverse:
                                    (SEQ ID NO: 7)
5'-CTGATCCACTAACGCCCTCC-3'

β-Actin Forward:
                                    (SEQ ID NO: 8)
5'-ATCTGGCACCACACCTTCTACAATGAGCTGCG-3'

β-Actin Reverse:
                                    (SEQ ID NO: 9)
5'-CGTCATACTCCTGCTTGCTGATCCACATCTGC-3'
```

For amplification, Qiagen One step RT_PCR kit (Cat number: 210212) and BioRad T100 thermocycler are used. The description of RT-PCR is given in Table 4.

TABLE 4

| Components/Tube | Volume (μL) |
|---|---|
| 5x buffer | 5 |
| dNTP | 1 |
| Enzyme | 1 |
| Primers (Forward and Reverse; 10 μm each) | 1.5 |
| $H_2O$ | 15.25 (variable) |
| Template | 1 μg (MADD) 100 ng (β-actin) |
| Total Volume | 25 |

Amplification protocol for RT-PCR included (1) 50° C. for 30 minutes, (2) 95° C. for 15 minutes, (3) 94° C. for 50 seconds, (4) 55° C. for 50 seconds, (5) 72° C. for 60 seconds, (6) Repeat Steps 3-5, 39 times, (7) 72° C. for 7 minutes, and (8) Hold at 4° C.

5% Polyacrylamide Gel Electrophoresis.

Polyacrylamide gels are casted manually and prepared based upon recipe provided in Table 5, with all components added sequentially. All components are mixed together, poured and allowed to polymerize for an hour at room temperature.

TABLE 5

| Components/gel of 1 mm thickness | Volume |
|---|---|
| $H_2O$ | 19.4 ml |
| 10x TBE (BioRad; Cat number: 161-0741) | 1.25 ml |
| 30% Acrylamide (BioRad; Cat number: 161-0156) | 4.2 ml |
| 10% APS (Fisher; Cat number: BP179-25) | 150 μl |
| TEMED (BioRad; Cat number: 161-0801) | 15 μl |

The entire sample volume (25 μl) is mixed with 5 μl of 6× nucleic acid buffer (Thermo Fisher Scientific; Cat number: R0611) before loading on to the gel. Gel electrophoresis is carried out at 200 volts for two hours using BioRad Protean II Xi Cell. Gel is stained for 30 minutes using 100 ml of working staining solution (1 μg/ml Ethidium Bromide in 0.5×TBE). Ethidium bromide is procured from BioRad (Cat number 161-0433). Images are captured using BioRad ChemiDoc MP Imaging System.

These studies demonstrate effective transfection of the instant experimental nucleic acids as well as distinguish the effect of the transfection reagent on MADD expression (MADD knockdown) and cell survival.

Example 3: Effect of Protein Kinase Inhibitor Chemotherapeutics on Cell Death in Cancer Cells with and without MADD Knockdown The cytotoxic effects of protein kinase inhibitor chemotherapeutics on cancer cells in the presence or absence of MADD down-regulation may be determined.

SU.86.86, H2227, C643, PLC/PRF/5, C643, K562, AGS, OVCAR3 and H522 cells are cultured in their respective culture medium with appropriate supplements as described above. See overview of protocol presented in Table 6.

TABLE 6

| | |
|---|---|
| Day 0 | Cell seeding in 100 $mm^3$ plates and 96 well plates |
| Day 1 | Transfection with Scrambled (Scr) or MADD siRNA |
| Day 2 | Media change |

TABLE 6-continued

| | |
|---|---|
| Day 3 | Cells Reseeding in 96-well plates<br>Cell viability analysis in 96-well plate before reseeding |
| Day 4 | Chemotherapeutic drugs addition |

Cells are cultured and maintained at 37° C. in a humidified atmosphere containing 5% $CO_2$ as described above. On Day 0, Cells are seeded in 100 $mm^3$ tissue culture dishes (Corning; Cat Number: 353003) to attain 60-70% confluence. In parallel, cells are also seeded in one 96-well plate (Corning; Cat number: 353072) for analysis of survival before reseeding. After 12-18 hours (Day 1), cells are transfected with Scramble or MADD siRNA at 10 nM concentration. The sequences of siRNAs (double-stranded) used are:

```
MADD siRNA:
                                        (SEQ ID NO: 4)
5'-GAUUGUCAUAGAUUCGCCGTT-3'

Scramble siRNA:
                                        (SEQ ID NO: 5)
5'-UUGCUAAGCGUCGGUCAAUTT-3'
```

Stock siRNAs are reconstituted to 100 μM concentration in 1× siRNA dissolution buffer (GE Healthcare; Cat number: B-002000-UB-700) and stored at −20° C. For transfection, reaction mix per plate is prepared by adding 30 μl transfection mediating reagent sold under the trademark LIPOFECTAMINE® RNAimax (Invitrogen; Cat number 13778-150), 1 ml culture medium sold under the trademark OPTI-MEM® (Gibco; Cat number: 31985062), and an aliquot of the stock siRNA to obtain a final concentration of 10 nM siRNA per plate or wells of a plate containing 70% confluent cells. Reaction mix is incubated at room temperature for 10 minutes. Transfection mixture is added dropwise on to the plate containing 70% confluent cells in RPMI media with 10% FBS but no antibiotics. The transfection mix is added in parallel to cells plated in a 96-well plate.

Cells are incubated at 37° C. in humidified $CO_2$ incubator for 24 hours and the next day (Day 2) the media is replaced with complete RPMI (10% FBS and 1× antibiotic/antimycotic). Media is changed for all the cells.

After 48 hours of transfection (Day 3), cells are harvested by 0.05% trypsin (Gibco; Cat number: 25-300-054) treatment. Briefly, cells are washed with DPBS (Gibco; Cat number: 14190250) and treated with trypsin for 5 minutes. Subsequently, cells are detached and collected in 10 ml complete media. Cells suspension is centrifuged at 1500 rpm for 10 minutes. Supernatant is discarded and cell pellet is suspended in 5 ml complete RPMI. All cells (Control (untreated), Scramble and MADD siRNA transfected) are counted using hemocytometer before reseeding. For cell counting, equal volumes of cell suspension and Trypan Blue 0.4% (Lonza; Cat number: 17-942E) are mixed. Ten μl of cell suspension (with trypan blue) are placed on hemocytometer and cells are counted. Counting is performed twice and average is used to determine the cell number.

Equal number of cells (Control (untreated), Scramble and MADD siRNA transfected) are seeded in 96-well plates. On the same day (after 48 hours of transfection), an MTT assay is carried out to determine the relative cell survival before reseeding.

On Day 4, when cells are properly adhered and retained their shape in 96-well plates, drugs are added. All drugs are diluted in complete media on the same day prior to the addition to the cells. In untreated cells, media is replaced with complete media. Two hundred μl volume of media (with or without drugs) is used for the drug treatment assay. Plates are incubated 24 hours, 48 hours and 72 hours at 37° C. in humidified $CO_2$ incubator.

An MTT assay is performed to determine relative survival after drug treatment as described above. MTT (3-[4,5-Dimethylthiazol-2-yl]-2,5-diphenyltetrazolium bromide; Thiazolyl blue) is purchased from Sigma Aldrich (Cat number: M5655). MTT is dissolved in sterile DPBS at the concentration of 5 mg/ml and filtered through 0.45 μM syringe filter (Corning; Cat number: 431220). Ten μl of MTT solution is added per well of 96-well plate. Plates are incubated for 2 hours at 37° C. in the humidified $CO_2$ incubator. After 2 hours, media is aspirated using vacuum inside the biosafety hood. Purple colored crystals formed in viable cells are dissolved by adding 100 μl of Dimethyl sulfoxide (Thermo Fisher Scientific; Cat number D128-500) Plates are kept on shaker for 10 minutes for compete dissolution of crystals and absorbance is recorded at 595 nm using Bio-Rad iMark microplate reader. Data is analyzed in MICROSOFT EXCEL® software. Relative survival is calculated with respect to absorbance of control (untreated cells) to determine the effect of transfection as well as combination treatment.

Transfection with Scramble siRNA results in little or no spontaneous cell death. Spontaneous cell death may be attributed to the sensitivity of the individual cell lines to the transfection reagent. A Scramble siRNA transfection is necessarily included as a transfection control in each experiment and establishes a baseline which reflects the amount of cell death which may occur due to the transfection reaction.

Each data set takes into account any spontaneous cell death which is observed upon transfection with Scramble siRNA; the amount of spontaneous cell death from Scramble siRNA transfection (baseline) is subtracted from the amount of cell death observed in each siRNA transfection reaction to yield a Net Percent (Net %) cell death after accounting for Scrambled siRNA-induced cell death.

In an embodiment, 5 μM Sorafinib was added as monotherapy to SU.86.86 pancreatic cancer cells. Moreover, cells were transfected with MADD siRNA as monotherapy. In combination, 5 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 5 μM Sorafinib, and cells transfected with MADD siRNA and treated with 5 μM Sorafinib, was evaluated at 24 hours post Sorafinib treatment (Table 7).

TABLE 7

| Treatment | Observed % Cell death | Net % cell death* |
|---|---|---|
| Control (untreated) | 0 | 0 |
| Scrambled siRNA (alone) | 11 | 11 − 11 = 0 |
| MADD siRNA (alone) | 9 | 9 − 11 = 0 |
| Sorafinib (alone) | 17 | 17 |
| Sorafinib + MADD siRNA | 45 | 45 − 11 = 34 |

*Net % cell death after accounting for Scrambled (non-specific siRNA).

The results, as reported in Table 7, demonstrate that siRNA knockdown of MADD resulted in 0% cell death, Sorafinib monotherapy at 5 μM concentration resulted in 17% cell death, and addition of 5 μM Sorafinib to cells transfected with MADD siRNA resulted in 34% cell death. All results accommodated for transfection effect utilizing Scramble siRNA cell death data. Taken together, the results demonstrate synergy of the combination of siRNA knockdown of MADD and Sorafinib treatment, resulting in 34% cell death which far exceeds the additive effect of monotherapy with either MADD siRNA knockdown or Sorafinib monotherapy, the additive effect of each monotherapy being 17% cell death (Additive: Sorafinib+MADD siRNA=17+0=17% cell death).

In another embodiment, 1.25 μM Sorafinib was added as monotherapy to SU.86.86 pancreatic cancer cells. Moreover, cells were transfected with MADD siRNA as monotherapy. In combination, 1.25 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 1.25 μM Sorafinib, and cells transfected with MADD siRNA and treated with 1.25 μM Sorafinib, was evaluated at 72 hours post-Sorafinib treatment (Table 8).

TABLE 8

| Treatment | Observed % Cell death | Net % cell death* |
|---|---|---|
| Control (untreated) | 0 | 0 |
| Scrambled siRNA (alone) | 28 | 28 − 28 = 0 |
| MADD siRNA (alone) | 41 | 41 − 28 = 13 |
| Sorafinib (alone) | 0 | 0 |
| Sorafinib + MADD siRNA | 65 | 65 − 28 = 37 |

*Net % cell death after accounting for Scrambled (non-specific siRNA).

The results, as reported in Table 8, demonstrate that siRNA knockdown of MADD resulted in 13% cell death, Sorafinib monotherapy at 1.25 μM concentration resulted in 0% cell death, and addition of 1.25 μM Sorafinib to cells transfected with MADD siRNA resulted in 37% cell death. All results accommodated for transfection effect utilizing Scramble siRNA cell death data. Taken together, the results demonstrate synergy of the combination of siRNA knockdown of MADD and Sorafinib treatment, resulting in 37% cell death which far exceeds the additive effect of monotherapy with either MADD siRNA knockdown or Sorafinib monotherapy, the additive effect of each monotherapy being 13% cell death (Additive: Sorafinib+MADD siRNA=0+13=13% cell death).

In another embodiment, 3 μM Sorafinib was added as monotherapy to H2227 lung cancer cells. Moreover, cells were transfected with MADD siRNA as monotherapy. In combination, 3 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 3 μM Sorafinib, and cells transfected with MADD siRNA and treated with 3 μM Sorafinib, was evaluated at 48 hours post Sorafinib treatment (Table 9).

TABLE 9

| Treatment | Observed % Cell death | Net % cell death* |
|---|---|---|
| Control (untreated) | 0 | 0 |
| Scrambled siRNA (alone) | 28 | 28 − 28 = 0 |
| MADD siRNA (alone) | 35 | 35 − 28 = 7 |
| Sorafinib (alone) | 18 | 18 |
| Sorafinib + MADD siRNA | 67 | 67 − 28 = 39 |

*Net % cell death after accounting for Scrambled (non-specific siRNA).

The results, as reported in Table 9, demonstrate that siRNA knockdown of MADD resulted in 7% cell death, Sorafinib monotherapy at 3 μM concentration resulted in 18% cell death, and addition of 3 μM Sorafinib to cells transfected with MADD siRNA resulted in 39% cell death. All results accommodated for transfection effect utilizing Scramble siRNA cell death data. Taken together, the results demonstrate synergy of the combination of siRNA knockdown of MADD and Sorafinib treatment, resulting in 39% cell death which far exceeds the additive effect of monotherapy with either MADD siRNA knockdown or Sorafinib monotherapy, the additive effect of each monotherapy being 25% cell death (Additive: Sorafinib+MADD siRNA=18+7=25% cell death).

In another embodiment, 0.975 μM Sorafinib was added as monotherapy to C643 thyroid cancer cells. Moreover, cells were transfected with MADD siRNA as monotherapy. In combination, 0.975 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 0.975 μM Sorafinib, and cells transfected with MADD siRNA and treated with 0.975 μM Sorafinib, was evaluated at 48 hours post Sorafinib treatment (Table 10).

TABLE 10

| Treatment | Observed % Cell death | Net % cell death* |
|---|---|---|
| Control (untreated) | 0 | 0 |
| Scrambled siRNA (alone) | 1 | 1 − 1 = 0 |
| MADD siRNA (alone) | 14 | 14 − 1 = 13 |
| Sorafinib (alone) | 3 | 3 |
| Sorafinib + MADD siRNA | 32 | 32 − 1 = 31 |

*Net % cell death after accounting for Scrambled (non-specific siRNA).

The results, as reported in Table 10, demonstrate that siRNA knockdown of MADD resulted in 13% cell death, Sorafinib monotherapy at 0.975 μM concentration resulted in 3% cell death, and addition of 0.975 μM Sorafinib to cells transfected with MADD siRNA resulted in 31% cell death. All results accommodated for transfection effect utilizing Scramble siRNA cell death data. Taken together, the results demonstrate synergy of the combination of siRNA knockdown of MADD and Sorafinib treatment, resulting in 31% cell death which far exceeds the additive effect of monotherapy with either MADD siRNA knockdown or Sorafinib monotherapy, the additive effect of each monotherapy being 16% cell death (Additive: Sorafinib+MADD siRNA=3+13=16% cell death).

In another embodiment, 0.375 μM Sorafinib was added as monotherapy to PLC/PRF/5 hepatic cancer cells. Moreover, cells were transfected with MADD siRNA as monotherapy. In combination, 0.375 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 0.375 μM Sorafinib, and cells transfected with MADD siRNA and treated with 0.375 μM Sorafinib, was evaluated at 24 hours post Sorafinib treatment (Table 11).

TABLE 11

| Treatment | Observed % Cell death | Net % cell death* |
|---|---|---|
| Control (untreated) | 0 | 0 |
| Scrambled siRNA (alone) | 5 | 5 − 5 = 0 |
| MADD siRNA (alone) | 25 | 25 − 5 = 20 |
| Sorafinib (alone) | 13 | 13 |
| Sorafinib + MADD siRNA | 90 | 90 − 5 = 85 |

*Net % cell death after accounting for Scrambled (non-specific siRNA).

The results, as reported in Table 11, demonstrate that siRNA knockdown of MADD resulted in 20% cell death, Sorafinib monotherapy at 0.375 μM concentration resulted in 13% cell death, and addition of 0.375 μM Sorafinib to cells transfected with MADD siRNA resulted in 85% cell death. All results accommodated for transfection effect utilizing Scramble siRNA cell death data. Taken together, the results demonstrate synergy of the combination of siRNA knockdown of MADD and Sorafinib treatment, resulting in 85% cell death which far exceeds the additive effect of monotherapy with either MADD siRNA knockdown or Sorafinib monotherapy, the additive effect of each monotherapy being 33% cell death (Additive: Sorafinib+MADD siRNA=13+20=33% cell death).

In another embodiment, 1.56 μM Sorafinib was added as monotherapy to H522 lung cancer cells. Moreover, cells were transfected with MADD siRNA as monotherapy. In combination, 1.56 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 1.56 μM Sorafinib, and cells transfected with MADD siRNA and treated with 1.56 μM Sorafinib, was evaluated at 48 hours post Sorafinib treatment (Table 12).

TABLE 12

| Treatment | Observed % Cell death | Net % cell death* |
|---|---|---|
| Control (untreated) | 0 | 0 |
| Scrambled siRNA (alone) | 30 | 30 − 30 = 0 |
| MADD siRNA (alone) | 37 | 37 − 30 = 7 |
| Sorafinib (alone) | 0 | 0 |
| Sorafinib + MADD siRNA | 49 | 49 − 30 = 19 |

*Net % cell death after accounting for Scrambled (non-specific siRNA).

The results, as reported in Table 12, demonstrate that siRNA knockdown of MADD resulted in 7% cell death, Sorafinib monotherapy at 1.56 μM concentration resulted in 0% cell death, and addition of 1.56 μM Sorafinib to cells transfected with MADD siRNA resulted in 19% cell death. All results accommodated for transfection effect utilizing Scramble siRNA cell death data. Taken together, the results demonstrate synergy of the combination of siRNA knockdown of MADD and Sorafinib treatment, resulting in 19% cell death which far exceeds the additive effect of monotherapy with either MADD siRNA knockdown or Sorafinib monotherapy, the additive effect of each monotherapy being 7% cell death (Additive: Sorafinib+MADD siRNA=0+7=7% cell death).

In another embodiment, 0.3125 μM Sorafinib was added as monotherapy to K562 chronic myelogenous leukemia cells. Moreover, cells were transfected with MADD siRNA as monotherapy. In combination, 0.3125 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 0.3125 μM Sorafinib, and cells transfected with MADD siRNA and treated with 0.3125 μM Sorafinib, was evaluated at 72 hours post Sorafinib treatment (Table 13).

TABLE 13

| Treatment | Observed % Cell death | Net % cell death* |
|---|---|---|
| Control (untreated) | 0 | 0 |
| Scrambled siRNA (alone) | 12 | 12 − 12 = 0 |
| MADD siRNA (alone) | 59 | 59 − 12 = 47 |
| Sorafinib (alone) | 0 | 0 |
| Sorafinib + MADD siRNA | 84 | 84 − 12 = 72 |

*Net % cell death after accounting for Scrambled (non-specific siRNA).

The results, as reported in Table 13, demonstrate that siRNA knockdown of MADD resulted in 47% cell death, Sorafinib monotherapy at 0.3125 μM concentration resulted in 0% cell death, and addition of 0.3125 μM Sorafinib to cells transfected with MADD siRNA resulted in 72% cell death. All results accommodated for transfection effect utilizing Scramble siRNA cell death data. Taken together, the results demonstrate synergy of the combination of siRNA knockdown of MADD and Sorafinib treatment, resulting in 72% cell death which far exceeds the additive effect of monotherapy with either MADD siRNA knockdown or Sorafinib monotherapy, the additive effect of each monotherapy being 47% cell death (Additive: Sorafinib+MADD siRNA=0+47=47% cell death).

In another embodiment, 1.25 μM Sorafinib was added as monotherapy to K562 chronic myelogenous leukemia cells. Moreover, cells were transfected with MADD siRNA as monotherapy. In combination, 1.25 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 1.25 μM Sorafinib, and cells transfected with MADD siRNA and treated with 1.25 μM Sorafinib, was evaluated at 48 hours post Sorafinib treatment (Table 14).

TABLE 14

| Treatment | Observed % Cell death | Net % cell death* |
|---|---|---|
| Control (untreated) | 0 | 0 |
| Scrambled siRNA (alone) | 49 | 49 − 49 = 0 |
| MADD siRNA (alone) | 53 | 53 − 49 = 4 |
| Sorafinib (alone) | 0 | 0 |
| Sorafinib + MADD siRNA | 73 | 73 − 49 = 24 |

*Net % cell death after accounting for Scrambled (non-specific siRNA).

The results, as reported in Table 14, demonstrate that siRNA knockdown of MADD resulted in 24% cell death, Sorafinib monotherapy at 1.25 μM concentration resulted in 0% cell death, and addition of 1.25 μM Sorafinib to cells transfected with MADD siRNA resulted in 24% cell death. All results accommodated for transfection effect utilizing Scramble siRNA cell death data. Taken together, the results demonstrate synergy of the combination of siRNA knockdown of MADD and Sorafinib treatment, resulting in 24% cell death which far exceeds the additive effect of monotherapy with either MADD siRNA knockdown or Sorafinib monotherapy, the additive effect of each monotherapy being 4% cell death (Additive: Sorafinib+MADD siRNA=0+4=4% cell death).

In another embodiment, 0.625 μM Sorafinib was added as monotherapy to AGS gastric adenocarcinoma cells. Moreover, cells were transfected with MADD siRNA as monotherapy. In combination, 0.625 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 0.625 μM Sorafinib, and cells transfected with MADD siRNA and treated with 0.625 μM Sorafinib, was evaluated at 48 hours post Sorafinib treatment (Table 15).

TABLE 15

| Treatment | Observed % Cell death | Net % cell death* |
|---|---|---|
| Control (untreated) | 0 | 0 |
| Scrambled siRNA (alone) | 9 | 9 − 9 = 0 |
| MADD siRNA (alone) | 14 | 14 − 9 = 5 |
| Sorafinib (alone) | 12 | 12 |
| Sorafinib + MADD siRNA | 42 | 42 − 9 = 33 |

*Net % cell death after accounting for Scrambled (non-specific siRNA).

The results, as reported in Table 15, demonstrate that siRNA knockdown of MADD resulted in 5% cell death, Sorafinib monotherapy at 0.625 μM concentration resulted in 12% cell death, and addition of 0.625 μM Sorafinib to cells transfected with MADD siRNA resulted in 33% cell death. All results accommodated for transfection effect utilizing Scramble siRNA cell death data. Taken together, the results demonstrate synergy of the combination of siRNA knockdown of MADD and Sorafinib treatment, resulting in 33% cell death which far exceeds the additive effect of monotherapy with either MADD siRNA knockdown or Sorafinib monotherapy, the additive effect of each monotherapy being 17% cell death (Additive: Sorafinib+MADD siRNA=12+5=17% cell death).

In another embodiment, 5 μM Sorafinib was added as monotherapy to OVCAR3 ovarian cancer cells. Moreover, cells were transfected with MADD siRNA as monotherapy. In combination, 5 μM Sorafinib was added to cells transfected with MADD siRNA. The amount of cell death in the cell cultures of the treatment paradigm represented by untreated control cells, control cells transfected with Scrambled siRNA, cells transfected with MADD siRNA, cells treated with 5 μM Sorafinib, and cells transfected with MADD siRNA and treated with 5 μM Sorafinib, was evaluated at 48 hours post Sorafinib treatment (Table 16).

TABLE 16

| Treatment | Observed % Cell death | Net % cell death* |
|---|---|---|
| Control (untreated) | 0 | 0 |
| Scrambled siRNA (alone) | 17 | 17 − 17 = 0 |
| MADD siRNA (alone) | 19 | 19 − 17 = 2 |
| Sorafinib (alone) | 17 | 17 |
| Sorafinib + MADD siRNA | 57 | 57 − 17 = 40 |

*Net % cell death after accounting for Scrambled (non-specific siRNA).

The results, as reported in Table 16, demonstrate that siRNA knockdown of MADD resulted in 2% cell death, Sorafinib monotherapy at 5 μM concentration resulted in 17% cell death, and addition of 5 μM Sorafinib to cells transfected with MADD siRNA resulted in 40% cell death. All results accommodated for transfection effect utilizing Scramble siRNA cell death data. Taken together, the results demonstrate synergy of the combination of siRNA knockdown of MADD and Sorafinib treatment, resulting in 40% cell death which far exceeds the additive effect of monotherapy with either MADD siRNA knockdown or Sorafinib monotherapy, the additive effect of each monotherapy being 19% cell death (Additive: Sorafinib+MADD siRNA=17+2=19% cell death).

Considering the results of the foregoing experiments, the instant assay demonstrates that combination of protein kinase inhibitor chemotherapeutic treatment and MADD knock-down results in surprisingly synergistic effects on inducing cancer cell death. The results demonstrate that the combination protein kinase inhibitor chemotherapy and MADD knock down results in more than an additive effect on cell death. As a result, dosages of the protein kinase inhibitor chemotherapeutic may be lowered to a level which was previously considered to be non-therapeutic, thereby providing a cancer therapy which exhibits an unexpected margin of safety and reduction of unwanted side effects.

Example 4: Effect of Anthracycline Chemotherapeutics on Cell Death in Cancer Cells with and without MADD Knockdown The cytotoxic effects of anthracycline chemotherapeutics on cancer cells in the presence or absence of MADD down-regulation may be determined.

SU.86.86, H2227, C643, PLC/PRF/5, JIMT1, N87, K562, and H522 cells are cultured in their respective culture medium with appropriate supplements as described above. See overview of protocol presented in Table 17.

TABLE 17

| | |
|---|---|
| Day 0 | Cell seeding in 100 $mm^3$ plates and 96 well plates |
| Day 1 | Transfection with Scrambled (Scr) or MADD siRNA |
| Day 2 | Media change |
| Day 3 | Cells Reseeding in 96-well plates<br>Cell viability analysis in 96-well plate before reseeding |
| Day 4 | Chemotherapeutic drugs addition |

Cells are cultured and maintained at 37° C. in a humidified atmosphere containing 5% $CO_2$ as described above. On Day 0, Cells are seeded in 100 $mm^3$ tissue culture dishes (Corning; Cat Number: 353003) to attain 60-70% confluence. In parallel, cells are also seeded in one 96-well plate (Corning; Cat number: 353072) for analysis of survival before reseeding. After 12-18 hours (Day 1), cells are transfected with Scramble or MADD siRNA at 10 nM concentration. The sequences of siRNAs (double stranded) used are:

```
MADD siRNA:
                                       (SEQ ID NO: 4)
5'-GAUUGUCAUAGAUUCGCCGTT-3'

Scramble siRNA:
                                       (SEQ ID NO: 5)
5'-UUGCUAAGCGUCGGUCAAUTT-3'
```

Stock siRNAs are reconstituted to 100 μM concentration in 1× siRNA dissolution buffer (GE Healthcare; Cat number: B-002000-UB-700) and stored at −20° C. For transfection, reaction mix per plate is prepared by adding 30 μl transfection mediating reagent sold under the trademark LIPOFECTAMINE® RNAimax (Invitrogen; Cat number 13778-150), 1 ml culture medium sold under the trademark OPTI-MEM® (Gibco; Cat number: 31985062), and an aliquot of the stock siRNA to obtain a final concentration of 10 nM siRNA per plate or wells of a plate containing 70% confluent cells. Reaction mix is incubated at room temperature for 10 minutes. Transfection mixture is added dropwise on to the plate containing 70% confluent cells in RPMI media with 10% FBS but no antibiotics. The transfection mix is added in parallel to cells plated in a 96-well plate.

Cells are incubated at 37° C. in humidified $CO_2$ incubator for 24 hours and the next day (Day 2) the media is replaced with complete RPMI (10% FBS and 1× antibiotic/antimycotic). Media is changed for all the cells.

After 48 hours of transfection (Day 3), cells are harvested by 0.05% trypsin (Gibco; Cat number: 25-300-054) treatment. Briefly, cells are washed with DPBS (Gibco; Cat number: 14190250) and treated with trypsin for 5 minutes. Subsequently, cells are detached and collected in 10 ml complete media. Cells suspension is centrifuged at 1500 rpm for 10 minutes. Supernatant is discarded and cell pellet is suspended in 5 ml complete RPMI. All cells [Control (untreated), Scramble and MADD siRNA transfected] are counted using hemocytometer before reseeding. For cell counting, equal volumes of cell suspension and Trypan Blue 0.4% (Lonza; Cat number: 17-942E) are mixed. 10 μl of cell suspension (with trypan blue) are placed on hemocytometer and cells are counted. Counting is performed twice and average is used to determine the cell number.

Equal number of cells [Control (untreated), Scramble and MADD siRNA transfected] are seeded in 96-well plates. On the same day (after 48 hours of transfection), an MTT assay is carried out to determine the relative cell survival before reseeding.

On Day 4, when cells are properly adhered and retained their shape in 96-well plates, drugs are added. Doxorubicin was added at a working concentration of 5.0 nM, 9.375 nM, 0.075 μM, 0.25 μM, 0.5 μM, and 0.8 μM. All drugs are diluted in complete media on the same day prior to the addition to the cells. In untreated cells, media is replaced with complete media. Two hundred μl volume of media (with or without drugs) is used for the drug treatment assay. Plates are incubated 24 hours, 48 hours and 72 hours at 37° C. in humidified $CO_2$ incubator.

An MTT assay is performed to determine relative survival after drug treatment as described above. MTT (3-[4,5-Dimethylthiazol-2-yl]-2,5-diphenyltetrazolium bromide; Thiazolyl blue) is purchased from Sigma Aldrich (Cat number: M5655). MTT is dissolved in sterile DPBS at the concentration of 5 mg/ml and filtered through 0.45 μM syringe filter (Corning; Cat number: 431220). Ten μl of MTT solution is added per well of 96-well plate. Plates are incubated for 2 hours at 37° C. in the humidified $CO_2$ incubator. After 2 hours, media is aspirated using vacuum inside the biosafety hood. Purple colored crystals formed in viable cells are dissolved by adding 100 μl of Dimethyl sulfoxide (Thermo Fisher Scientific; Cat number D128-500). Plates are kept on shaker for 10 minutes for compete dissolution of crystals and absorbance is recorded at 595 nm using Bio-Rad iMark microplate reader. Data is analyzed in MICROSOFT EXCEL® software. Relative survival is calculated with respect to absorbance of control (untreated cells) to determine the effect of transfection as well as combination treatment.

Transfection with Scramble siRNA results in little or no spontaneous cell death. Spontaneous cell death may be attributed to the sensitivity of the individual cell lines to the transfection reagent. A Scramble siRNA transfection is necessarily included as a transfection control in each experiment and establishes a baseline which reflects the amount of cell death which may occur due to the transfection reaction.

Each data set takes into account any spontaneous cell death which is observed upon transfection with Scramble siRNA; the amount of spontaneous cell death from Scramble siRNA transfection (baseline) is subtracted from the amount of cell death observed in each siRNA transfection reaction to yield a Net Percent (Net %) cell death after accounting for Scrambled siRNA-induced cell death.

In an embodiment, 5 nM Doxorubicin was added as monotherapy to SU.86.86 pancreatic cancer cells. Moreover, cells were transfected with MADD siRNA as monotherapy. In combination, 5 nM Doxorubicin was added to cells transfected with MADD siRNA. The amount of cell death in the cell cultures of the treatment paradigm represented by untreated control cells, control cells transfected with Scrambled siRNA, cells transfected with MADD siRNA, cells treated with 5 nM Doxorubicin, and cells transfected with MADD siRNA and treated with 5 nM Doxorubicin, was evaluated at 24 hours post Doxorubicin treatment (Table 18).

TABLE 18

| Treatment | Observed % Cell death | Net % cell death* |
|---|---|---|
| Control (untreated) | 0 | 0 |
| Scrambled siRNA (alone) | 11 | 11 − 11 = 0 |
| MADD siRNA (alone) | 9 | 9 − 11 = 0 |
| Doxorubicin (alone) | 36 | 36 |
| Doxorubicin + MADD siRNA | 63 | 63 − 11 = 52 |

*Net % cell death after accounting for Scrambled (non-specific siRNA).

The results, as reported in Table 18, demonstrate that siRNA knockdown of MADD resulted in 0% cell death, Doxorubicin monotherapy at 5 nM concentration resulted in 36% cell death, and addition of 5 nM Doxorubicin to cells transfected with MADD siRNA resulted in 52% cell death. All results accommodated for transfection effect utilizing Scramble siRNA cell death data. Taken together, the results demonstrate synergy of the combination of siRNA knockdown of MADD and Doxorubicin treatment, resulting in 52% cell death which far exceeds the additive effect of monotherapy with either MADD siRNA knockdown or Doxorubicin monotherapy, the additive effect of each monotherapy being 36% cell death (Additive: Doxorubicin+MADD siRNA=36+0=36% cell death).

In another embodiment, 9.375 nM Doxorubicin was added as monotherapy to H2227 lung cancer cells. Moreover, cells were transfected with MADD siRNA as monotherapy. In combination, 9.375 nM Doxorubicin was added to cells transfected with MADD siRNA. The amount of cell death in the cell cultures of the treatment paradigm represented by untreated control cells, control cells transfected with Scrambled siRNA, cells transfected with MADD siRNA, cells treated with 9.375 nM Doxorubicin, and cells transfected with MADD siRNA and treated with 9.375 nM Doxorubicin, was evaluated at 48 hours post Doxorubicin treatment (Table 19).

TABLE 19

| Treatment | Observed % Cell death | Net % cell death* |
|---|---|---|
| Control (untreated) | 0 | 0 |
| Scrambled siRNA (alone) | 28 | 28 − 28 = 0 |
| MADD siRNA (alone) | 35 | 35 − 28 = 7 |
| Doxorubicin (alone) | 3 | 3 |
| Doxorubicin + MADD siRNA | 66 | 66 − 28 = 38 |

*Net % cell death after accounting for Scrambled (non-specific siRNA).

The results, as reported in Table 19, demonstrate that siRNA knockdown of MADD resulted in 7% cell death, Doxorubicin monotherapy at 9.375 nM concentration resulted in 3% cell death, and addition of 9.375 nM Doxorubicin to cells transfected with MADD siRNA resulted in 38% cell death. All results accommodated for transfection effect utilizing Scramble siRNA cell death data. Taken together, the results demonstrate synergy of the combination of siRNA knockdown of MADD and Doxorubicin treatment, resulting in 38% cell death which far exceeds the additive effect of monotherapy with either MADD siRNA knockdown or Doxorubicin monotherapy, the additive effect of each monotherapy being 10% cell death (Additive: Doxorubicin+MADD siRNA=3+7=10% cell death).

In an embodiment, 0.075 μM Doxorubicin was added as monotherapy to JIMT1 breast cancer cells. Moreover, cells were transfected with MADD siRNA as monotherapy. In combination, 0.075 μM Doxorubicin was added to cells transfected with MADD siRNA. The amount of cell death in the cell cultures of the treatment paradigm represented by untreated control cells, control cells transfected with Scrambled siRNA, cells transfected with MADD siRNA, cells treated with 0.075 μM Doxorubicin, and cells transfected with MADD siRNA and treated with 0.075 μM Doxorubicin, was evaluated at 24 hours post Doxorubicin treatment (Table 20).

TABLE 20

| Treatment | Observed % Cell death | Net % cell death* |
|---|---|---|
| Control (untreated) | 0 | 0 |
| Scrambled siRNA (alone) | 33 | 33 − 33 = 0 |
| MADD siRNA (alone) | 59 | 59 − 33 = 26 |
| Doxorubicin (alone) | 17 | 17 |
| Doxorubicin + MADD siRNA | 92 | 92 − 33 = 59 |

*Net % cell death after accounting for Scrambled (non-specific siRNA).

The results, as reported in Table 20, demonstrate that siRNA knockdown of MADD resulted in 26% cell death, Doxorubicin monotherapy at 0.075 μM concentration resulted in 17% cell death, and addition of 0.075 μM Doxorubicin to cells transfected with MADD siRNA resulted in 59% cell death. All results accommodated for transfection effect utilizing Scramble siRNA cell death data. Taken together, the results demonstrate synergy of the combination of siRNA knockdown of MADD and Doxorubicin treatment, resulting in 59% cell death which far exceeds the additive effect of monotherapy with either MADD siRNA knockdown or Doxorubicin monotherapy, the additive effect of each monotherapy being 43% cell death (Additive: Doxorubicin+MADD siRNA=17+26=43% cell death).

In an embodiment, 0.8 μM Doxorubicin was added as monotherapy to N87 gastric carcinoma cells. Moreover, cells were transfected with MADD siRNA as monotherapy. In combination, 0.8 μM Doxorubicin was added to cells transfected with MADD siRNA. The amount of cell death in the cell cultures of the treatment paradigm represented by untreated control cells, control cells transfected with Scrambled siRNA, cells transfected with MADD siRNA, cells treated with 0.8 μM Doxorubicin, and cells transfected with MADD siRNA and treated with 0.8 μM Doxorubicin, was evaluated at 72 hours post Doxorubicin treatment (Table 21).

TABLE 21

| Treatment | Observed % Cell death | Net % cell death* |
|---|---|---|
| Control (untreated) | 0 | 0 |
| Scrambled siRNA (alone) | 14 | 14 − 14 = 0 |
| MADD siRNA (alone) | 21 | 21 − 14 = 7 |
| Doxorubicin (alone) | 38 | 38 |
| Doxorubicin + MADD siRNA | 70 | 70 − 14 = 56 |

*Net % cell death after accounting for Scrambled (non-specific siRNA).

The results, as reported in Table 21, demonstrate that siRNA knockdown of MADD resulted in 7% cell death, Doxorubicin monotherapy at 0.8 μM concentration resulted in 38% cell death, and addition of 0.8 μM Doxorubicin to cells transfected with MADD siRNA resulted in 56% cell death. All results accommodated for transfection effect utilizing Scramble siRNA cell death data. Taken together, the results demonstrate synergy of the combination of siRNA knockdown of MADD and Doxorubicin treatment, resulting in 56% cell death which far exceeds the additive effect of monotherapy with either MADD siRNA knockdown or Doxorubicin monotherapy, the additive effect of each monotherapy being 45% cell death (Additive: Doxorubicin+MADD siRNA=38+7=45% cell death).

In an embodiment, 0.25 μM Doxorubicin was added as monotherapy to K562 chronic myelogenous leukemia cells. Moreover, cells were transfected with MADD siRNA as monotherapy. In combination, 0.25 μM Doxorubicin was added to cells transfected with MADD siRNA. The amount of cell death in the cell cultures of the treatment paradigm represented by untreated control cells, control cells transfected with Scrambled siRNA, cells transfected with MADD siRNA, cells treated with 0.25 μM Doxorubicin, and cells transfected with MADD siRNA and treated with 0.25 μM Doxorubicin, was evaluated at 72 hours post Doxorubicin treatment (Table 22).

TABLE 22

| Treatment | Observed % Cell death | Net % cell death* |
|---|---|---|
| Control (untreated) | 0 | 0 |
| Scrambled siRNA (alone) | 12 | 12 − 12 = 0 |
| MADD siRNA (alone) | 59 | 59 − 12 = 47 |
| Doxorubicin (alone) | 11 | 11 |
| Doxorubicin + MADD siRNA | 88 | 88 − 12 = 76 |

*Net % cell death after accounting for Scrambled (non-specific siRNA).

The results, as reported in Table 22, demonstrate that siRNA knockdown of MADD resulted in 47% cell death, Doxorubicin monotherapy at 0.25 μM concentration resulted in 11% cell death, and addition of 0.25 μM Doxorubicin to cells transfected with MADD siRNA resulted in 76% cell death. All results accommodated for transfection effect utilizing Scramble siRNA cell death data. Taken together, the results demonstrate synergy of the combination of siRNA knockdown of MADD and Doxorubicin treatment, resulting in 76% cell death which far exceeds the additive effect of monotherapy with either MADD siRNA knockdown or Doxorubicin monotherapy, the additive effect of each monotherapy being 58% cell death (Additive: Doxorubicin+MADD siRNA=11+47=58% cell death).

In an embodiment, 0.5 μM Doxorubicin was added as monotherapy to K562 chronic myelogenous leukemia cells. Moreover, cells were transfected with MADD siRNA as monotherapy. In combination, 0.5 μM Doxorubicin was added to cells transfected with MADD siRNA. The amount of cell death in the cell cultures of the treatment paradigm represented by untreated control cells, control cells transfected with Scrambled siRNA, cells transfected with MADD siRNA, cells treated with 0.5 μM Doxorubicin, and cells transfected with MADD siRNA and treated with 0.5 μM Doxorubicin, was evaluated at 48 hours post Doxorubicin treatment (Table 23).

TABLE 23

| Treatment | Observed % Cell death | Net % cell death* |
|---|---|---|
| Control (untreated) | 0 | 0 |
| Scrambled siRNA (alone) | 49 | 49 − 49 = 0 |
| MADD siRNA (alone) | 53 | 53 − 49 = 4 |
| Doxorubicin (alone) | 0 | 0 |
| Doxorubicin + MADD siRNA | 72 | 72 − 49 = 23 |

*Net % cell death after accounting for Scrambled (non-specific siRNA).

The results, as reported in Table 23, demonstrate that siRNA knockdown of MADD resulted in 4% cell death, Doxorubicin monotherapy at 0.5 μM concentration resulted in 0% cell death, and addition of 0.5 μM Doxorubicin to cells transfected with MADD siRNA resulted in 23% cell death. All results accommodated for transfection effect utilizing Scramble siRNA cell death data. Taken together, the results demonstrate synergy of the combination of siRNA knockdown of MADD and Doxorubicin treatment, resulting in 23% cell death which far exceeds the additive effect of monotherapy with either MADD siRNA knockdown or Doxorubicin monotherapy, the additive effect of each monotherapy being 4% cell death (Additive: Doxorubicin+MADD siRNA=0+4=4% cell death).

Considering the results of the foregoing experiments, the instant assay demonstrates that combination of anthracycline chemotherapeutic treatment and MADD knock-down results in surprisingly synergistic effects on inducing cancer cell death. The results demonstrate that the combination anthracycline chemotherapy and MADD knock down results in more than an additive effect on cell death. As a result, dosages of the anthracycline chemotherapeutic may be lowered to a level which was previously considered to be non-therapeutic, thereby providing a cancer therapy which exhibits an unexpected margin of safety and reduction of unwanted side effects.

Example 5: Effect of Nucleoside Analog Chemotherapeutics on Cell Death in Cancer Cells with and without MADD Knockdown The cytotoxic effects of nucleoside analog chemotherapeutics on cancer cells in the presence or absence of MADD down-regulation may be determined.

All cells are cultured in their respective culture medium with appropriate supplements as described above. See overview of protocol presented in Table 24.

TABLE 24

| | |
|---|---|
| Day 0 | Cell seeding in 100 $mm^3$ plates and 96 well plates |
| Day 1 | Transfection with Scrambled (Scr) or MADD siRNA |
| Day 2 | Media change |
| Day 3 | Cells Reseeding in 96-well plates<br>Cell viability analysis in 96-well plate before reseeding |
| Day 4 | Chemotherapeutic drugs addition |

Cells are cultured and maintained at 37° C. in a humidified atmosphere containing 5% $CO_2$ as described above. On Day 0, Cells are seeded in 100 $mm^3$ tissue culture dishes (Corning; Cat Number: 353003) to attain 60-70% confluence. In parallel, cells are also seeded in one 96-well plate (Corning; Cat number: 353072) for analysis of survival before reseeding. After 12-18 hours (Day 1), cells are transfected with Scramble or MADD siRNA at 10 nM concentration. The sequences of siRNAs (double stranded) used are:

```
MADD siRNA:
                                        (SEQ ID NO: 4)
5'-GAUUGUCAUAGAUUCGCCGTT-3'

Scramble siRNA:
                                        (SEQ ID NO: 5)
5'-UUCCUAAGCGUCGGUCAAUTT-3'
```

Stock siRNAs are reconstituted to 100 μM concentration in 1× siRNA dissolution buffer (GE Healthcare; Cat number: B-002000-UB-700) and stored at −20° C. For transfection, reaction mix per plate is prepared by adding 30 μl transfection mediating reagent sold under the trademark LIPOFECTAMINE® RNAimax (Invitrogen; Cat number 13778-150), 1 ml culture medium sold under the trademark OPTI-MEM® (Gibco; Cat number: 31985062), and an aliquot of the stock siRNA to obtain a final concentration of 10 nM siRNA per plate or wells of a plate containing 70% confluent cells. Reaction mix is incubated at room temperature for 10 minutes. Transfection mixture is added dropwise on to the plate containing 70% confluent cells in RPMI media with 10% FBS but no antibiotics. The transfection mix is added in parallel to cells plated in a 96-well plate.

Cells are incubated at 37° C. in humidified $CO_2$ incubator for 24 hours and the next day (Day 2) the media is replaced with complete RPMI (10% FBS and 1× antibiotic/antimycotic). Media is changed for all the cells.

After 48 hours of transfection (Day 3), cells are harvested by 0.05% trypsin (Gibco; Cat number: 25-300-054) treatment. Briefly, cells are washed with DPBS (Gibco; Cat number: 14190250) and treated with trypsin for 5 minutes. Subsequently, cells are detached and collected in 10 ml complete media. Cells suspension is centrifuged at 1500 rpm for 10 minutes. Supernatant is discarded and cell pellet is suspended in 5 ml complete RPMI. All cells [Control (untreated), Scramble and MADD siRNA transfected] are counted using hemocytometer before reseeding. For cell counting, equal volumes of cell suspension and Trypan Blue 0.4% (Lonza; Cat number: 17-942E) are mixed. 10 μl of cell suspension (with trypan blue) are placed on hemocytometer and cells are counted. Counting is performed twice and average is used to determine the cell number.

Equal number of cells [Control (untreated), Scramble and MADD siRNA transfected] are seeded in 96-well plates. On the same day (after 48 hours of transfection), an MTT assay is carried out to determine the relative cell survival before reseeding.

On Day 4, when cells are properly adhered and retained their shape in 96-well plates, drugs are added. All drugs are diluted in complete media on the same day prior to the addition to the cells. In untreated cells, media is replaced with complete media. Two hundred μl volume of media (with or without drugs) is used for the drug treatment assay. Plates are incubated 24 hours, 48 hours and 72 hours at 37° C. in humidified $CO_2$ incubator.

An MTT assay is performed to determine relative survival after drug treatment as described above. MTT (3-[4,5-Dimethylthiazol-2-yl]-2,5-diphenyltetrazolium bromide; Thiazolyl blue) is purchased from Sigma Aldrich (Cat number: M5655). MTT is dissolved in sterile DPBS at the concentration of 5 mg/ml and filtered through 0.45 μM syringe filter (Corning; Cat number: 431220). Ten μl of MTT solution is added per well of 96-well plate. Plates are incubated for 2 hours at 37° C. in the humidified $CO_2$ incubator. After 2 hours, media is aspirated using vacuum inside the biosafety hood. Purple colored crystals formed in viable cells are dissolved by adding 100 μl of Dimethyl sulfoxide (Thermo Fisher Scientific; Cat number D128-500). Plates are kept on shaker for 10 minutes for compete dissolution of crystals and absorbance is recorded at 595 nm using Bio-Rad iMark microplate reader. Data is analyzed in MICROSOFT EXCEL® software. Relative survival is calculated with respect to absorbance of control (untreated cells) to determine the effect of transfection as well as combination treatment.

Transfection with Scramble siRNA results in little or no spontaneous cell death. Spontaneous cell death may be attributed to the sensitivity of the individual cell lines to the transfection reagent. A Scramble siRNA transfection is necessarily included as a transfection control in each experiment and establishes a baseline which reflects the amount of cell death which may occur due to the transfection reaction.

Each data set takes into account any spontaneous cell death which is observed upon transfection with Scramble siRNA; the amount of spontaneous cell death from Scramble siRNA transfection (baseline) is subtracted from the amount of cell death observed in each siRNA transfection reaction to yield a Net Percent (Net %) cell death after accounting for Scrambled siRNA-induced cell death.

In an embodiment, 25 nM Gemcitabine was added as monotherapy to H2227 lung cancer cells. Moreover, cells were transfected with MADD siRNA as monotherapy. In combination, 25 nM Gemcitabine was added to cells transfected with MADD siRNA. The amount of cell death in the cell cultures of the treatment paradigm represented by untreated control cells, control cells transfected with Scrambled siRNA, cells transfected with MADD siRNA, cells treated with 25 nM Gemcitabine, and cells transfected with MADD siRNA and treated with 25 nM Gemcitabine, was evaluated at 48 hours post Gemcitabine treatment (Table 25)

TABLE 25

| Treatment | Observed % Cell death | Net % cell death* |
|---|---|---|
| Control (untreated) | 0 | 0 |
| Scrambled siRNA (alone) | 28 | 28 − 28 = 0 |
| MADD siRNA (alone) | 35 | 35 − 28 = 7 |
| Gemcitabine (alone) | 15 | 15 |
| Gemcitabine + MADD siRNA | 66 | 66 − 28 = 38 |

*Net % cell death after accounting for Scrambled (non-specific siRNA).

The results, as reported in Table 25, demonstrate that siRNA knockdown of MADD resulted in 7% cell death, Gemcitabine monotherapy at 25 nM concentration resulted in 15% cell death, and addition of 25 nM Gemcitabine to cells transfected with MADD siRNA resulted in 38% cell death. All results accommodated for transfection effect utilizing Scramble siRNA cell death data. Taken together, the results demonstrate synergy of the combination of siRNA knockdown of MADD and Gemcitabine treatment, resulting in 38% cell death which far exceeds the additive effect of monotherapy with either MADD siRNA knockdown or Gemcitabine monotherapy, the additive effect of each monotherapy being 22% cell death (Additive: Gemcitabine+MADD siRNA=15+7=22% cell death).

In another embodiment, 8.2 nM Gemcitabine was added as monotherapy to H522 lung cancer cells. Moreover, cells were transfected with MADD siRNA as monotherapy. In combination, 8.2 nM Gemcitabine was added to cells transfected with MADD siRNA. The amount of cell death in the cell cultures of the treatment paradigm represented by untreated control cells, control cells transfected with Scrambled siRNA, cells transfected with MADD siRNA, cells treated with 8.2 nM Gemcitabine, and cells transfected with MADD siRNA and treated with 8.2 nM Gemcitabine, was evaluated at 48 hours post Gemcitabine treatment (Table 26).

TABLE 26

| Treatment | Observed % Cell death | Net % cell death* |
|---|---|---|
| Control (untreated) | 0 | 0 |
| Scrambled siRNA (alone) | 30 | 30 − 30 = 0 |
| MADD siRNA (alone) | 37 | 37 − 30 = 7 |
| Gemcitabine (alone) | 4 | 4 |
| Gemcitabine + MADD siRNA | 50 | 50 − 30 = 20 |

*Net % cell death after accounting for Scrambled (non-specific siRNA).

The results, as reported in Table 26, demonstrate that siRNA knockdown of MADD resulted in 7% cell death, Gemcitabine monotherapy at 8.2 μM concentration resulted in 4% cell death, and addition of 8.2 nM Gemcitabine to cells transfected with MADD siRNA resulted in 20% cell death. All results accommodated for transfection effect utilizing Scramble siRNA cell death data. Taken together, the results demonstrate synergy of the combination of siRNA knockdown of MADD and Gemcitabine treatment, resulting in 20% cell death which far exceeds the additive effect of monotherapy with either MADD siRNA knockdown or Gemcitabine monotherapy, the additive effect of each monotherapy being 11% cell death (Additive: Gemcitabine+MADD siRNA=4+7=11% cell death).

In another embodiment, 0.03125 μM Gemcitabine was added as monotherapy to PLC/PRF/5 hepatic cancer cells. Moreover, cells were transfected with MADD siRNA as monotherapy. In combination, 0.03125 μM Gemcitabine was added to cells transfected with MADD siRNA. The amount of cell death in the cell cultures of the treatment paradigm represented by untreated control cells, control cells transfected with Scrambled siRNA, cells transfected with MADD siRNA, cells treated with 0.03125 μM Gemcitabine, and cells transfected with MADD siRNA and treated with 0.03125 μM Gemcitabine, was evaluated at 24 hours post Gemcitabine treatment (Table 27).

TABLE 27

| Treatment | Observed % Cell death | Net % cell death* |
|---|---|---|
| Control (untreated) | 0 | 0 |
| Scrambled siRNA (alone) | 5 | 5 − 5 = 0 |
| MADD siRNA (alone) | 25 | 25 − 5 = 20 |
| Gemcitabine (alone) | 1 | 1 |
| Gemcitabine + MADD siRNA | 71 | 71 − 5 = 66 |

*Net % cell death after accounting for Scrambled (non-specific siRNA).

The results, as reported in Table 27, demonstrate that siRNA knockdown of MADD resulted in 20% cell death, Gemcitabine monotherapy at 0.03125 μM concentration resulted in 1% cell death, and addition of 0.03125 μM Gemcitabine to cells transfected with MADD siRNA resulted in 66% cell death. All results accommodated for transfection effect utilizing Scramble siRNA cell death data. Taken together, the results demonstrate synergy of the combination of siRNA knockdown of MADD and Gemcitabine treatment, resulting in 66% cell death which far exceeds the additive effect of monotherapy with either MADD siRNA knockdown or Gemcitabine monotherapy, the additive effect of each monotherapy being 20.69% cell death (Additive: Gemcitabine+MADD siRNA=1+20=21% cell death).

In another embodiment, 0.1 μM Gemcitabine was added as monotherapy to OVCAR3 ovarian cancer cells. Moreover, cells were transfected with MADD siRNA as monotherapy. In combination, 0.1 μM Gemcitabine was added to cells transfected with MADD siRNA. The amount of cell death in the cell cultures of the treatment paradigm represented by untreated control cells, control cells transfected with Scrambled siRNA, cells transfected with MADD siRNA, cells treated with 0.1 μM Gemcitabine, and cells transfected with MADD siRNA and treated with 0.1 μM Gemcitabine, was evaluated at 48 hours post Gemcitabine treatment (Table 28).

TABLE 28

| Treatment | Observed % Cell death | Net % cell death* |
|---|---|---|
| Control (untreated) | 0 | 0 |
| Scrambled siRNA (alone) | 17 | 17 − 17 = 0 |
| MADD siRNA (alone) | 19 | 19 − 17 = 2 |
| Gemcitabine (alone) | 28 | 28 |
| Gemcitabine + MADD siRNA | 57 | 57 − 17 = 40 |

*Net % cell death after accounting for Scrambled (non-specific siRNA).

The results, as reported in Table 28, demonstrate that siRNA knockdown of MADD resulted in 2% cell death, Gemcitabine monotherapy at 0.1 μM concentration resulted in 28% cell death, and addition of 0.1 μM Gemcitabine to cells transfected with MADD siRNA resulted in 40% cell death. All results accommodated for transfection effect utilizing Scramble siRNA cell death data. Taken together, the results demonstrate synergy of the combination of siRNA knockdown of MADD and Gemcitabine treatment, resulting in 40% cell death which exceeds the additive effect of monotherapy with either MADD siRNA knockdown or Gemcitabine monotherapy, the additive effect of each monotherapy being 30% cell death (Additive: Gemcitabine+MADD siRNA=28+2=30% cell death).

In another embodiment, 0.0125 μM Gemcitabine was added as monotherapy to OVCAR3 ovarian cancer cells. Moreover, cells were transfected with MADD siRNA as monotherapy. In combination, 0.0125 μM Gemcitabine was added to cells transfected with MADD siRNA. The amount of cell death in the cell cultures of the treatment paradigm represented by untreated control cells, control cells transfected with Scrambled siRNA, cells transfected with MADD siRNA, cells treated with 0.0125 μM Gemcitabine, and cells transfected with MADD siRNA and treated with 0.0125 μM Gemcitabine, was evaluated at 72 hours post Gemcitabine treatment (Table 29).

TABLE 29

| Treatment | Observed % Cell death | Net % cell death* |
|---|---|---|
| Control (untreated) | 0 | 0 |
| Scrambled siRNA (alone) | 26 | 26 − 26 = 0 |
| MADD siRNA (alone) | 23 | 23 − 26 = 0 |
| Gemcitabine (alone) | 19 | 19 |
| Gemcitabine + MADD siRNA | 79 | 79 − 26 = 53 |

*Net % cell death after accounting for Scrambled (non-specific siRNA).

The results, as reported in Table 29, demonstrate that siRNA knockdown of MADD resulted in 2% cell death, Gemcitabine monotherapy at 0.1 μM concentration resulted in 0% cell death, and addition of 0.0125 μM Gemcitabine to cells transfected with MADD siRNA resulted in 19% cell death. All results accommodated for transfection effect utilizing Scramble siRNA cell death data. Taken together, the results demonstrate synergy of the combination of siRNA knockdown of MADD and Gemcitabine treatment, resulting in 53% cell death which far exceeds the additive effect of monotherapy with either MADD siRNA knockdown or Gemcitabine monotherapy, the additive effect of each monotherapy being 19% cell death (Additive: Gemcitabine+MADD siRNA=19+0=19% cell death).

In another embodiment, 1 μM Gemcitabine was added as monotherapy to AGS gastric adenocarcinoma cells. Moreover, cells were transfected with MADD siRNA as monotherapy. In combination, 1 μM Gemcitabine was added to cells transfected with MADD siRNA. The amount of cell death in the cell cultures of the treatment paradigm represented by untreated control cells, control cells transfected with Scrambled siRNA, cells transfected with MADD siRNA, cells treated with 1 μM Gemcitabine, and cells transfected with MADD siRNA and treated with 1 μM Gemcitabine, was evaluated at 48 hours post Gemcitabine treatment (Table 30).

TABLE 30

| Treatment | Observed % Cell death | Net % cell death* |
|---|---|---|
| Control (untreated) | 0 | 0 |
| Scrambled siRNA (alone) | 9 | 9 − 9 = 0 |
| MADD siRNA (alone) | 14 | 14 − 9 = 5 |
| Gemcitabine (alone) | 38 | 38 |
| Gemcitabine + MADD siRNA | 59 | 59 − 9 = 50 |

*Net % cell death after accounting for Scrambled (non-specific siRNA).

The results, as reported in Table 30, demonstrate that siRNA knockdown of MADD resulted in 5% cell death, Gemcitabine monotherapy at 1 μM concentration resulted in 38% cell death, and addition of 1 μM Gemcitabine to cells transfected with MADD siRNA resulted in 50% cell death. All demonstrate synergy of the combination of siRNA knockdown of MADD and Gemcitabine treatment, resulting in 50% cell death which exceeds the additive effect of monotherapy with either MADD siRNA knockdown or Gemcitabine monotherapy, the additive effect of each monotherapy being 43% cell death (Additive: Gemcitabine+MADD siRNA=38+5=43% cell death).

In another embodiment, 25 μM 5-flurouracil was added as monotherapy to AGS gastric adenocarcinoma cells. Moreover, cells were transfected with MADD siRNA as monotherapy. In combination, 25 μM 5-flurouracil was added to cells transfected with MADD siRNA. The amount of cell death in the cell cultures of the treatment paradigm represented by untreated control cells, control cells transfected with Scrambled siRNA, cells transfected with MADD siRNA, cells treated with 25 μM 5-flurouracil, and cells transfected with MADD siRNA and treated with 25 μM 5-flurouracil, was evaluated at 72 hours post 5-flurouracil treatment (Table 31).

TABLE 31

| Treatment | Observed % Cell death | Net % cell death* |
|---|---|---|
| Control (untreated) | 0 | 0 |
| Scrambled siRNA (alone) | 17 | 17 − 17 = 0 |
| MADD siRNA (alone) | 20 | 20 − 17 = 3 |
| 5-flurouracil (alone) | 22 | 22 |
| 5-flurouracil + MADD siRNA | 47 | 47 − 17 = 30 |

*Net % cell death after accounting for Scrambled (non-specific siRNA).

The results, as reported in Table 31, demonstrate that siRNA knockdown of MADD resulted in 3% cell death, 5-flurouracil monotherapy at 25 μM concentration resulted in 22% cell death, and addition of 25 μM 5-flurouracil to cells transfected with MADD siRNA resulted in 30% cell death. All results accommodated for transfection effect utilizing Scramble siRNA cell death data. Taken together, the results demonstrate synergy of the combination of siRNA knockdown of MADD and 5-flurouracil treatment, resulting in 30% cell death which exceeds the additive effect of monotherapy with either MADD siRNA knockdown or 5-flurouracil monotherapy, the additive effect of each monotherapy being 25% cell death (Additive: 5-flurouracil+MADD siRNA=22+3=25% cell death).

Considering the results of the foregoing experiments, the instant assay demonstrates that combination of nucleoside analog chemotherapeutic treatment and MADD knockdown results in surprisingly synergistic effects on inducing cancer cell death. The results demonstrate that the combination nucleoside analog chemotherapy and MADD knock down results in more than an additive effect on cell death. As a result, dosages of the nucleoside analog chemotherapeutic may be lowered to a level which was previously considered to be non-therapeutic, thereby providing a cancer therapy which exhibits an unexpected margin of safety and reduction of unwanted side effects.

Example 6: Effect of Apoptosis-Inducing Molecular Therapeutics on Cell Death in Cancer Cells with and without MADD Knockdown The cytotoxic effects of apoptosis-inducing molecular therapeutics on cancer cells in the presence or absence of MADD down-regulation may be determined.

All cells are cultured in their respective culture medium with appropriate supplements as described above. See overview of protocol presented in Table 32.

TABLE 32

| | |
|---|---|
| Day 0 | Cell seeding in 100 $mm^3$ plates and 96 well plates |
| Day 1 | Transfection with Scrambled (Scr) or MADD siRNA |
| Day 2 | Media change |
| Day 3 | Cells Reseeding in 96-well plates<br>Cell viability analysis in 96-well plate before reseeding |
| Day 4 | Chemotherapeutic drugs addition |

Cells are cultured and maintained at 37° C. in a humidified atmosphere containing 5% $CO_2$ as described above. On Day 0, Cells are seeded in 100 $mm^3$ tissue culture dishes (Corning; Cat Number: 353003) to attain 60-70% confluence. In parallel, cells are also seeded in one 96-well plate (Corning; Cat number: 353072) for analysis of survival before reseeding. After 12-18 hours (Day 1), cells are transfected with Scramble or MADD siRNA at 10 nM concentration. The sequences of siRNAs (double stranded) used are:

```
MADD siRNA:
                                        (SEQ ID NO: 4)
5'-GAUUGUCAUAGAUUCGCCGTT-3'

Scramble siRNA:
                                        (SEQ ID NO: 5)
5'-UUGCUAAGCGUCGGUCAAUTT-3'
```

Stock siRNAs are reconstituted to 100 μM concentration in 1× siRNA dissolution buffer (GE Healthcare; Cat number: B-002000-UB-700) and stored at −20° C. For transfection, reaction mix per plate is prepared by adding 30 μl transfection mediating reagent sold under the trademark LIPOFECTAMINE® RNAimax (Invitrogen; Cat number 13778-

150), 1 ml culture medium sold under the trademark OPTI-MEM® (Gibco; Cat number: 31985062), and an aliquot of the stock siRNA to obtain a final concentration of 10 nM siRNA per plate or wells of a plate containing 70% confluent cells. Reaction mix is incubated at room temperature for 10 minutes. Transfection mixture is added dropwise on to the plate containing 70% confluent cells in RPMI media with 10% FBS but no antibiotics. The transfection mix is added in parallel to cells plated in a 96-well plate.

Cells are incubated at 37° C. in humidified $CO_2$ incubator for 24 hours and the next day (Day 2) the media is replaced with complete RPMI (10% FBS and 1× antibiotic/antimycotic). Media is changed for all the cells.

After 48 hours of transfection (Day 3), cells are harvested by 0.05% trypsin (Gibco; Cat number: 25-300-054) treatment. Briefly, cells are washed with DPBS (Gibco; Cat number: 14190250) and treated with trypsin for 5 minutes. Subsequently, cells are detached and collected in 10 ml complete media. Cells suspension is centrifuged at 1500 rpm for 10 minutes. Supernatant is discarded and cell pellet is suspended in 5 ml complete RPMI. All cells [Control (untreated), Scramble and MADD siRNA transfected] are counted using hemocytometer before reseeding. For cell counting, equal volumes of cell suspension and Trypan Blue 0.4% (Lonza; Cat number: 17-942E) are mixed. Ten μl of cell suspension (with trypan blue) are placed on hemocytometer and cells are counted. Counting is performed twice and average is used to determine the cell number.

Equal number of cells [Control (untreated), Scramble and MADD siRNA transfected] are seeded in 96-well plates. On the same day (after 48 hours of transfection), an MTT assay is carried out to determine the relative cell survival before reseeding.

On Day 4, when cells are properly adhered and retained their shape in 96-well plates, drugs are added. All drugs are diluted in complete media on the same day prior to the addition to the cells. In untreated cells, media is replaced with complete media. Two hundred μl volume of media (with or without drugs) is used for the drug treatment assay. Plates are incubated 24 h, 48 h and 72 hours at 37° C. in humidified $CO_2$ incubator.

An MTT assay is performed to determine relative survival after drug treatment as described above. MTT (3-[4,5-Dimethylthiazol-2-yl]-2,5-diphenyltetrazolium bromide; Thiazolyl blue) is purchased from Sigma Aldrich (Cat number: M5655). MTT is dissolved in sterile DPBS at the concentration of 5 mg/ml and filtered through 0.45 μM syringe filter (Corning; Cat number: 431220). Ten μl of MTT solution is added per well of 96-well plate. Plates are incubated for 2 hours at 37° C. in the humidified $CO_2$ incubator. After 2 hours, media is aspirated using vacuum inside the biosafety hood. Purple colored crystals formed in viable cells are dissolved by adding 100 μl of Dimethyl sulfoxide (Thermo Fisher Scientific; Cat number D128-500) Plates are kept on shaker for 10 minutes for compete dissolution of crystals and absorbance is recorded at 595 nm using Bio-Rad iMark microplate reader. Data is analyzed in MICROSOFT EXCEL® software. Relative survival is calculated with respect to absorbance of control (untreated cells) to determine the effect of transfection as well as combination treatment.

Transfection with Scramble siRNA results in little or no spontaneous cell death. Spontaneous cell death may be attributed to the sensitivity of the individual cell lines to the transfection reagent. A Scramble siRNA transfection is necessarily included as a transfection control in each experiment and establishes a baseline which reflects the amount of cell death which may occur due to the transfection reaction.

Each data set takes into account any spontaneous cell death which is observed upon transfection with Scramble siRNA; the amount of spontaneous cell death from Scramble siRNA transfection (baseline) is subtracted from the amount of cell death observed in each siRNA transfection reaction to yield a Net Percent (Net %) cell death after accounting for Scrambled siRNA-induced cell death.

In an embodiment, 100 ng/ml TRAIL was added as monotherapy to H522 lung cancer cells. Moreover, cells were transfected with MADD siRNA as monotherapy. In combination, 100 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 100 ng/ml TRAIL, and cells transfected with MADD siRNA and treated with 100 ng/ml TRAIL, was evaluated at 48 hours post TRAIL treatment (Table 33).

TABLE 33

| Treatment | Observed % Cell death | Net % cell death* |
|---|---|---|
| Control (untreated) | 0 | 0 |
| Scrambled siRNA (alone) | 30 | 30 − 30 = 0 |
| MADD siRNA (alone) | 37 | 37 − 30 = 7 |
| TRAIL (alone) | 0 | 0 |
| TRAIL + MADD siRNA | 45 | 45 − 30 = 15 |

*Net % cell death after accounting for Scrambled (non-specific siRNA).

The results, as reported in Table 33, demonstrate that siRNA knockdown of MADD resulted in 7% cell death, TRAIL monotherapy at 100 ng/ml concentration resulted in 0% cell death, and addition of 100 ng/ml TRAIL to cells transfected with MADD siRNA resulted in 15% cell death. All results accommodated for transfection effect utilizing Scramble siRNA cell death data. Taken together, the results demonstrate synergy of the combination of siRNA knockdown of MADD and TRAIL treatment, resulting in 15% cell death which far exceeds the additive effect of monotherapy with either MADD siRNA knockdown or TRAIL monotherapy, the additive effect of each monotherapy being 7% cell death (Additive: TRAIL+MADD siRNA=0+7=7% cell death).

In another embodiment, 50 ng/ml TRAIL was added as monotherapy to SKOV3 ovarian cancer cells. Moreover, cells were transfected with MADD siRNA as monotherapy. In combination, 50 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 50 ng/ml TRAIL, and cells transfected with MADD siRNA and treated with 50 ng/ml TRAIL, was evaluated at 48 hours post TRAIL treatment (Table 34).

TABLE 34

| Treatment | Observed % Cell death | Net % cell death* |
|---|---|---|
| Control (untreated) | 0 | 0 |
| Scrambled siRNA (alone) | 9 | 9 − 9 = 0 |
| MADD siRNA (alone) | 38 | 38 − 9 = 29 |

TABLE 34-continued

| Treatment | Observed % Cell death | Net % cell death* |
|---|---|---|
| TRAIL (alone) | 13 | 13 |
| TRAIL + MADD siRNA | 88 | 88 − 9 = 79 |

*Net % cell death after accounting for Scrambled (non-specific siRNA).

The results, as reported in Table 34, demonstrate that siRNA knockdown of MADD resulted in 29% cell death, TRAIL monotherapy at 50 ng/ml concentration resulted in 13% cell death, and addition of 50 ng/ml TRAIL to cells transfected with MADD siRNA resulted in 79% cell death. All results accommodated for tranfection effect utilizing Scramble siRNA cell death data. Taken together, the results demonstrate synergy of the combination of siRNA knockdown of MADD and TRAIL treatment, resulting in 79% cell death which far exceeds the additive effect of monotherapy with either MADD siRNA knockdown or TRAIL monotherapy, the additive effect of each monotherapy being 42% cell death (Additive: TRAIL+MADD siRNA=13+29=42% cell death).

In another embodiment, 6.25 ng/ml TRAIL was added as monotherapy to 8508C thyroid cancer cells. Moreover, cells were transfected with MADD siRNA as monotherapy. In combination, 6.25 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 6.25 ng/ml TRAIL, and cells transfected with MADD siRNA and treated with 6.25 ng/ml TRAIL, was evaluated at 48 hours post TRAIL treatment (Table 35).

TABLE 35

| Treatment | Observed % Cell death | Net % cell death* |
|---|---|---|
| Control (untreated) | 0 | 0 |
| Scrambled siRNA (alone) | 10 | 10 − 10 = 0 |
| MADD siRNA (alone) | 49 | 49 − 10 = 39 |
| TRAIL (alone) | 7 | 7 |
| TRAIL + MADD siRNA | 59 | 59 − 10 = 49 |

*Net % cell death after accounting for Scrambled (non-specific siRNA).

The results, as reported in Table 35, demonstrate that siRNA knockdown of MADD resulted in 39% cell death, TRAIL monotherapy at 6.25 ng/ml concentration resulted in 6.56% cell death, and addition of 6.25 ng/ml TRAIL to cells transfected with MADD siRNA resulted in 49% cell death. All results accommodated for tranfection effect utilizing Scramble siRNA cell death data. Taken together, the results demonstrate synergy of the combination of siRNA knockdown of MADD and TRAIL treatment, resulting in 49% cell death which exceeds the additive effect of monotherapy with either MADD siRNA knockdown or TRAIL monotherapy, the additive effect of each monotherapy being 46% cell death (Additive: TRAIL+MADD siRNA=7+39=46% cell death).

In another embodiment, 50 ng/ml TRAIL was added as monotherapy to PLC/PRF/5 hepatic cancer cells. Moreover, cells were transfected with MADD siRNA as monotherapy. In combination, 50 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 50 ng/ml TRAIL, and cells transfected with MADD siRNA and treated with 50 ng/ml TRAIL, was evaluated at 24 hours post TRAIL treatment (Table 36).

TABLE 36

| Treatment | Observed % Cell death | Net % cell death* |
|---|---|---|
| Control (untreated) | 0 | 0 |
| Scrambled siRNA (alone) | 5 | 5 − 5 = 0 |
| MADD siRNA (alone) | 25 | 25 − 5 = 20 |
| TRAIL (alone) | 0 | 0 |
| TRAIL + MADD siRNA | 57 | 57 − 5 = 52 |

*Net % cell death after accounting for Scrambled (non-specific siRNA).

The results, as reported in Table 36, demonstrate that siRNA knockdown of MADD resulted in 20% cell death, TRAIL monotherapy at 50 ng/ml concentration resulted in 0% cell death, and addition of 50 ng/ml TRAIL to cells transfected with MADD siRNA resulted in 52% cell death. All results accommodated for transfection effect utilizing Scramble siRNA cell death data. Taken together, the results demonstrate synergy of the combination of siRNA knockdown of MADD and TRAIL treatment, resulting in 52% cell death which far exceeds the additive effect of monotherapy with either MADD siRNA knockdown or TRAIL monotherapy, the additive effect of each monotherapy being 20% cell death (Additive: TRAIL+MADD siRNA=0+20=20% cell death).

In another embodiment, 50 ng/ml TRAIL was added as monotherapy to HCT116 colon cancer cells. Moreover, cells were transfected with MADD siRNA as monotherapy. In combination, 50 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 50 ng/ml TRAIL, and cells transfected with MADD siRNA and treated with 50 ng/ml TRAIL, was evaluated at 48 hours post TRAIL treatment (Table 37).

TABLE 37

| Treatment | Observed % Cell death | Net % cell death* |
|---|---|---|
| Control (untreated) | 0 | 0 |
| Scrambled siRNA (alone) | 27 | 27 − 27 = 0 |
| MADD siRNA (alone) | 43 | 43 − 27 = 16 |
| TRAIL (alone) | 27 | 27 |
| TRAIL + MADD siRNA | 73 | 73 − 27 = 46 |

*Net % cell death after accounting for Scrambled (non-specific siRNA).

The results, as reported in Table 37, demonstrate that siRNA knockdown of MADD resulted in 16% cell death, TRAIL monotherapy at 50 ng/ml concentration resulted in 27% cell death, and addition of 50 ng/ml TRAIL to cells transfected with MADD siRNA resulted in 52% cell death. All results accommodated for transfection effect utilzing Scramble siRNA cell death data. Taken together, the results demonstrate synergy of the combination of siRNA knockdown of MADD and TRAIL treatment, resulting in 46% cell death which exceeds the additive effect of monotherapy with either MADD siRNA knockdown or TRAIL monotherapy, the additive effect of each monotherapy being 43% cell death (Additive: TRAIL+MADD siRNA=27+16=43% cell death).

In another embodiment, 12.5 ng/ml TRAIL was added as monotherapy to K562 chronic myelogenous leukemia cancer cells. Moreover, cells were transfected with MADD siRNA as monotherapy. In combination, 12.5 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 12.5 ng/ml TRAIL, and cells transfected with MADD siRNA and treated with 12.5 ng/ml TRAIL, was evaluated at 48 hours post TRAIL treatment (Table 38).

TABLE 38

| Treatment | Observed % Cell death | Net % cell death* |
|---|---|---|
| Control (untreated) | 0 | 0 |
| Scrambled siRNA (alone) | 49 | 49 − 49 = 0 |
| MADD siRNA (alone) | 53 | 53 − 49 = 4 |
| TRAIL (alone) | 0 | 0 |
| TRAIL + MADD siRNA | 65 | 65 − 49 = 16 |

*Net % cell death after accounting for Scrambled (non-specific siRNA).

The results, as reported in Table 38, demonstrate that siRNA knockdown of MADD resulted in 4% cell death, TRAIL monotherapy at 12.5 ng/ml concentration resulted in 0% cell death, and addition of 12.5 ng/ml TRAIL to cells transfected with MADD siRNA resulted in 16% cell death. All results accommodated for transfection effect utilizing Scramble siRNA cell death data. Taken together, the results demonstrate synergy of the combination of siRNA knockdown of MADD and TRAIL treatment, resulting in 16% cell death which exceeds the additive effect of monotherapy with either MADD siRNA knockdown or TRAIL monotherapy, the additive effect of each monotherapy being 4% cell death (Additive: TRAIL+MADD siRNA=0+4=4% cell death).

In another embodiment, 6.25 ng/ml TRAIL was added as monotherapy to K562 chronic myelogenous leukemia cancer cells. Moreover, cells were transfected with MADD siRNA as monotherapy. In combination, 6.25 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 6.25 ng/ml TRAIL, and cells transfected with MADD siRNA and treated with 6.25 ng/ml TRAIL, was evaluated at 72 hours post TRAIL treatment (Table 39).

TABLE 39

| Treatment | Observed % Cell death | Net % cell death* |
|---|---|---|
| Control (untreated) | 0 | 0 |
| Scrambled siRNA (alone) | 12 | 12 − 12 = 0 |
| MADD siRNA (alone) | 59 | 59 − 12 = 47 |
| TRAIL (alone) | 0 | 0 |
| TRAIL + MADD siRNA | 81 | 81 − 12 = 69 |

*Net % cell death after accounting for Scrambled (non-specific siRNA).

The results, as reported in Table 39, demonstrate that siRNA knockdown of MADD resulted in 47% cell death, TRAIL monotherapy at 6.25 ng/ml concentration resulted in 0% cell death, and addition of 6.25 ng/ml TRAIL to cells transfected with MADD siRNA resulted in 69% cell death. All results accommodated for transfection effect utilizing Scramble siRNA cell death data. Taken together, the results demonstrate synergy of the combination of siRNA knockdown of MADD and TRAIL treatment, resulting in 69% cell death which exceeds the additive effect of monotherapy with either MADD siRNA knockdown or TRAIL monotherapy, the additive effect of each monotherapy being 59% cell death (Additive: TRAIL+MADD siRNA=0+59=59% cell death).

In another embodiment, 6.25 ng/ml TRAIL was added as monotherapy to AGS gastric adenocarcinoma cancer cells. Moreover, cells were transfected with MADD siRNA as monotherapy. In combination, 6.25 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 6.25 ng/ml TRAIL, and cells transfected with MADD siRNA and treated with 6.25 ng/ml TRAIL, was evaluated at 72 hours post TRAIL treatment (Table 40).

TABLE 40

| Treatment | Observed % Cell death | Net % cell death* |
|---|---|---|
| Control (untreated) | 0 | 0 |
| Scrambled siRNA (alone) | 17 | 17 − 17 = 0 |
| MADD siRNA (alone) | 20 | 20 − 17 = 3 |
| TRAIL (alone) | 7 | 7 |
| TRAIL + MADD siRNA | 41 | 41 − 17 = 24 |

*Net % cell death after accounting for Scrambled (non-specific siRNA).

The results, as reported in Table 40, demonstrate that siRNA knockdown of MADD resulted in 3% cell death, TRAIL monotherapy at 6.25 ng/ml concentration resulted in 0% cell death, and addition of 6.25 ng/ml TRAIL to cells transfected with MADD siRNA resulted in 24% cell death. All results accommodated for transfection effect utilizing Scramble siRNA cell death data. Taken together, the results demonstrate synergy of the combination of siRNA knockdown of MADD and TRAIL treatment, resulting in 24% cell death which far exceeds the additive effect of monotherapy with either MADD siRNA knockdown or TRAIL monotherapy, the additive effect of each monotherapy being 10% cell death (Additive: TRAIL+MADD siRNA=7+3=10% cell death).

In another embodiment, 12.5 ng/ml TRAIL was added as monotherapy to CFPAC-1 pancreatic cancer cells. Moreover, cells were transfected with MADD siRNA as monotherapy. In combination, 12.5 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 12.5 ng/ml TRAIL, and cells transfected with MADD siRNA and treated with 12.5 ng/ml TRAIL, was evaluated at 72 hours post TRAIL treatment (Table 41).

TABLE 41

| Treatment | Observed % Cell death | Net % cell death* |
|---|---|---|
| Control (untreated) | 0 | 0 |
| Scrambled siRNA (alone) | 0 | 0 − 0 = 0 |
| MADD siRNA (alone) | 53 | 53 − 0 = 53 |

TABLE 41-continued

| Treatment | Observed % Cell death | Net % cell death* |
|---|---|---|
| TRAIL (alone) | 8 | 8 |
| TRAIL + MADD siRNA | 94 | 65 − 0 = 94 |

*Net % cell death after accounting for Scrambled (non-specific siRNA).

The results, as reported in Table 41, demonstrate that siRNA knockdown of MADD resulted in 53% cell death, TRAIL monotherapy at 12.5 ng/ml concentration resulted in 0% cell death, and addition of 12.5 ng/ml TRAIL to cells transfected with MADD siRNA resulted in 8% cell death. All results accommodated for transfection effect utilizing Scramble siRNA cell death data. Taken together, the results demonstrate synergy of the combination of siRNA knockdown of MADD and TRAIL treatment, resulting in 94% cell death which far exceeds the additive effect of monotherapy with either MADD siRNA knockdown or TRAIL monotherapy, the additive effect of each monotherapy being 61% cell death (Additive: TRAIL+MADD siRNA=8+53=61% cell death).

In another embodiment, 6.25 ng/ml TRAIL was added as monotherapy to CFPAC-1 pancreatic cancer cells. Moreover, cells were transfected with MADD siRNA as monotherapy. In combination, 6.25 ng/ml TRAIL was added to cells transfected with MADD siRNA. The amount of cell death in the cell cultures of the treatment paradigm represented by untreated control cells, control cells transfected with Scrambled siRNA, cells transfected with MADD siRNA, cells treated with 6.25 ng/ml TRAIL, and cells transfected with MADD siRNA and treated with 6.25 ng/ml TRAIL, was evaluated at 72 hours post TRAIL treatment (Table 42).

TABLE 42

| Treatment | Observed % Cell death | Net % cell death* |
|---|---|---|
| Control (untreated) | 0 | 0 |
| Scrambled siRNA (alone) | 0 | 17 − 17 = 0 |
| MADD siRNA (alone) | 53 | 53 − 0 = 53 |
| TRAIL (alone) | 30 | 30 |
| TRAIL + MADD siRNA | 91 | 91 − 0 = 91 |

*Net % cell death after accounting for Scrambled (non-specific siRNA).

The results, as reported in Table 42, demonstrate that siRNA knockdown of MADD resulted in 53% cell death, TRAIL monotherapy at 6.25 ng/ml concentration resulted in 30% cell death, and addition of 6.25 ng/ml TRAIL to cells transfected with MADD siRNA resulted in 91% cell death. All results accommodated for transfection effect utilizing Scramble siRNA cell death data. Taken together, the results demonstrate synergy of the combination of siRNA knockdown of MADD and TRAIL treatment, resulting in 91% cell death which far exceeds the additive effect of monotherapy with either MADD siRNA knockdown or TRAIL monotherapy, the additive effect of each monotherapy being 83% cell death (Additive: TRAIL+MADD siRNA=30+53=83% cell death).

Considering the results of the foregoing experiments, the instant assay demonstrates that combination of apoptosis-inducing molecular therapeutic treatment and MADD knock-down results in surprisingly synergistic effects on inducing cancer cell death. The results demonstrate that the combination cytokine chemotherapy and MADD knock down results in more than an additive effect on cell death. As a result, dosages of the apoptosis-inducing molecular therapeutic may be lowered to a level which was previously considered to be non-therapeutic, thereby providing a cancer therapy which exhibits an unexpected margin of safety and reduction of unwanted side effects.

Example 7: Effect of Alkylating Agent Chemotherapeutics on Cell Death in Cancer Cells with and without MADD Knockdown The cytotoxic effects of alkylating agent chemotherapeutics on cancer cells in the presence or absence of MADD down-regulation may be determined.

SU.86.86, H2227, C643, PLC/PRF/5, JIMT1, HTH7, 8505C and H522 cells are cultured in their respective culture medium with appropriate supplements as described above. See overview of protocol presented in Table 43.

TABLE 43

| | |
|---|---|
| Day 0 | Cell seeding in 100 mm$^3$ plates and 96 well plates |
| Day 1 | Transfection with Scrambled (Scr) or MADD siRNA |
| Day 2 | Media change |
| Day 3 | Cells Reseeding in 96-well plates<br>Cell viability analysis in 96-well plate before reseeding |
| Day 4 | Chemotherapeutic drugs addition |

Cells are cultured and maintained at 37° C. in a humidified atmosphere containing 5% $CO_2$ as described above. On Day 0, Cells are seeded in 100 mm$^3$ tissue culture dishes (Corning; Cat Number: 353003) to attain 60-70% confluence. In parallel, cells are also seeded in one 96-well plate (Corning; Cat number: 353072) for analysis of survival before reseeding. After 12-18 hours (Day 1), cells are transfected with Scramble or MADD siRNA at 10 nM concentration. The sequences of siRNAs (double stranded) used are:

```
MADD siRNA:
                                        (SEQ ID NO: 4)
5'-GAUUGUCAUAGAUUCGCCGTT-3'

Scramble siRNA:
                                        (SEQ ID NO: 5)
5'-UUGCUAAGCGUCGGUCAAUTT-3'
```

Stock siRNAs are reconstituted to 100 μM concentration in 1× siRNA dissolution buffer (GE Healthcare; Cat number: B-002000-UB-700) and stored at −20° C. For transfection, reaction mix per plate is prepared by adding 30 μl transfection mediating reagent sold under the trademark LIPOFECTAMINE® RNAimax (Invitrogen; Cat number 13778-150), 1 ml culture medium sold under the trademark OPTI-MEM® (Gibco; Cat number: 31985062), and an aliquot of the stock siRNA to obtain a final concentration of 10 nM siRNA per plate or wells of a plate containing 70% confluent cells. Reaction mix is incubated at room temperature for 10 minutes. Transfection mixture is added dropwise on to the plate containing 70% confluent cells in RPMI media with 10% FBS but no antibiotics. The transfection mix is added in parallel to cells plated in a 96-well plate.

Cells are incubated at 37° C. in humidified $CO_2$ incubator for 24 hours and the next day (Day 2) the media is replaced with complete RPMI (10% FBS and 1× antibiotic/antimycotic). Media is changed for all the cells.

After 48 hours of transfection (Day 3), cells are harvested by 0.05% trypsin (Gibco; Cat number: 25-300-054) treatment. Briefly, cells are washed with DPBS (Gibco; Cat number: 14190250) and treated with trypsin for 5 minutes. Subsequently, cells are detached and collected in 10 ml complete media. Cells suspension is centrifuged at 1500 rpm for 10 minutes. Supernatant is discarded and cell pellet is suspended in 5 ml complete RPMI. All cells (Control (untreated), Scramble and MADD siRNA transfected) are counted using hemocytometer before reseeding. For cell counting, equal volumes of cell suspension and Trypan Blue 0.4% (Lonza; Cat number: 17-942E) are mixed. Ten μl of cell suspension (with trypan blue) are placed on hemocytometer and cells are counted. Counting is performed twice and average is used to determine the cell number.

Equal number of cells (Control (untreated), Scramble and MADD siRNA transfected) are seeded in 96-well plates. On the same day (after 48 hours of transfection), an MTT assay is carried out to determine the relative cell survival before reseeding.

On Day 4, when cells are properly adhered and retained their shape in 96-well plates, drugs are added. All drugs are diluted in complete media on the same day prior to the addition to the cells. In untreated cells, media is replaced with complete media. Two hundred μl volume of media (with or without drugs) is used for the drug treatment assay. Plates are incubated 24 hours, 48 hours and 72 hours at 37° C. in humidified $CO_2$ incubator.

An MTT assay is performed to determine relative survival after drug treatment as described above. MTT (3-[4,5-Dimethylthiazol-2-yl]-2,5-diphenyltetrazolium bromide; Thiazolyl blue) is purchased from Sigma Aldrich (Cat number: M5655). MTT is dissolved in sterile DPBS at the concentration of 5 mg/ml and filtered through 0.45 μM syringe filter (Corning; Cat number: 431220). Ten μl of MTT solution is added per well of 96-well plate. Plates are incubated for 2 hours at 37° C. in the humidified $CO_2$ incubator. After 2 hours, media is aspirated using vacuum inside the biosafety hood. Purple colored crystals formed in viable cells are dissolved by adding 100 μl of Dimethyl sulfoxide (Thermo Fisher Scientific; Cat number D128-500) Plates are kept on shaker for 10 minutes for compete dissolution of crystals and absorbance is recorded at 595 nm using Bio-Rad iMark microplate reader. Data is analyzed in MICROSOFT EXCEL® software. Relative survival is calculated with respect to absorbance of control (untreated cells) to determine the effect of transfection as well as combination treatment.

Transfection with Scramble siRNA results in little or no spontaneous cell death. Spontaneous cell death may be attributed to the sensitivity of the individual cell lines to the transfection reagent. A Scramble siRNA transfection is necessarily included as a transfection control in each experiment and establishes a baseline which reflects the amount of cell death which may occur due to the transfection reaction.

Each data set takes into account any spontaneous cell death which is observed upon transfection with Scramble siRNA; the amount of spontaneous cell death from Scramble siRNA transfection (baseline) is subtracted from the amount of cell death observed in each siRNA transfection reaction to yield a Net Percent (Net %) cell death after accounting for Scrambled siRNA-induced cell death.

In an embodiment, 2.5 μM Cisplatin was added as monotherapy to 8505C thyroid cancer cells. Moreover, cells were transfected with MADD siRNA as monotherapy. In combination, 2.5 AM Cisplatin was added to cells transfected with MADD siRNA. The amount of cell death in the cell cultures of the treatment paradigm represented by untreated control cells, control cells transfected with Scrambled siRNA, cells transfected with MADD siRNA, cells treated with 2.5 μM Cisplatin, and cells transfected with MADD siRNA and treated with 2.5 μM Cisplatin, was evaluated at 48 hours post Cisplatin treatment (Table 44).

TABLE 44

| Treatment | Observed % Cell death | Net % cell death* |
|---|---|---|
| Control (untreated) | 0 | 0 |
| Scrambled siRNA (alone) | 10 | 10 |
| MADD siRNA (alone) | 49 | 49 − 10 = 39 |
| Cisplatin (alone) | 19 | 19 |
| Cisplatin + MADD siRNA | 73 | 73 − 10 = 63 |

*Net % cell death after accounting for Scrambled (non-specific siRNA).

The results, as reported in Table 44, demonstrate that siRNA knockdown of MADD resulted in 39% cell death, Cisplatin monotherapy at 2.5 μM concentration resulted in 19% cell death, and addition of 2.5 μM Cisplatin to cells transfected with MADD siRNA resulted in 63% cell death. All results accommodated for transfection effect utilizing Scramble siRNA cell death data. Taken together, the results demonstrate synergy of the combination of siRNA knockdown of MADD and Cisplatin treatment, resulting in 63% cell death which exceeds the additive effect of monotherapy with either MADD siRNA knockdown or Cisplatin monotherapy, the additive effect of each monotherapy being 58% cell death (Additive: Cisplatin+MADD siRNA=19+39=58% cell death).

In another embodiment, 5 μM Cisplatin was added as monotherapy to HTH7 thyroid cancer cells. Moreover, cells were transfected with MADD siRNA as monotherapy. In combination, 5 μM Cisplatin was added to cells transfected with MADD siRNA. The amount of cell death in the cell cultures of the treatment paradigm represented by untreated control cells, control cells transfected with Scrambled siRNA, cells transfected with MADD siRNA, cells treated with 5 μM Cisplatin, and cells transfected with MADD siRNA and treated with 5 μM Cisplatin, was evaluated at 24 hours post Cisplatin treatment (Table 45).

TABLE 45

| Treatment | Observed % Cell death | Net % cell death* |
|---|---|---|
| Control (untreated) | 0 | 0 |
| Scrambled siRNA (alone) | 0 | 0 − 0 = 0 |
| MADD siRNA (alone) | 6 | 6 − 0 = 6 |
| Cisplatin (alone) | 13 | 13 |
| Cisplatin + MADD siRNA | 31 | 31 − 0 = 31 |

*Net % cell death after accounting for Scrambled (non-specific siRNA).

The results, as reported in Table 45, demonstrate that siRNA knockdown of MADD resulted in 6% cell death, Cisplatin monotherapy at 5 μM concentration resulted in 13% cell death, and addition of 5 μM Cisplatin to cells transfected with MADD siRNA resulted in 31% cell death. All results accommodated for transfection effect utilizing demonstrate synergy of the combination of siRNA knockdown of MADD and Cisplatin treatment, resulting in 31% cell death which far exceeds the additive effect of monotherapy with either MADD siRNA knockdown or Cisplatin monotherapy, the additive effect of each monotherapy being 19% cell death (Additive: Cisplatin+MADD siRNA=13+6=19% cell death).

In another embodiment, 1.25 μM Cisplatin was added as monotherapy to HTH7 thyroid cancer cells. Moreover, cells were transfected with MADD siRNA as monotherapy. In combination, 1.25 μM Cisplatin was added to cells transfected with MADD siRNA. The amount of cell death in the cell cultures of the treatment paradigm represented by untreated control cells, control cells transfected with Scrambled siRNA, cells transfected with MADD siRNA, cells treated with 1.25 μM Cisplatin, and cells transfected with MADD siRNA and treated with 1.25 μM Cisplatin, was evaluated at 72 hours post Cisplatin treatment (Table 46).

TABLE 46

| Treatment | Observed % Cell death | Net % cell death* |
|---|---|---|
| Control (untreated) | 0 | 0 |
| Scrambled siRNA (alone) | 0 | 0 − 0 = 0 |
| MADD siRNA (alone) | 54 | 54 − 0 = 54 |
| Cisplatin (alone) | 0 | 0 |
| Cisplatin + MADD siRNA | 67 | 67 − 0 = 67 |

*Net % cell death after accounting for Scrambled (non-specific siRNA).

The results, as reported in Table 46, demonstrate that siRNA knockdown of MADD resulted in 54% cell death, Cisplatin monotherapy at 1.25 μM concentration resulted in 0% cell death, and addition of 1.25 μM Cisplatin to cells transfected with MADD siRNA resulted in 67% cell death. All results accommodated for transfection effect utilizing Scramble siRNA cell death data. Taken together, the results demonstrate synergy of the combination of siRNA knockdown of MADD and Cisplatin treatment, resulting in 67% cell death which far exceeds the additive effect of monotherapy with either MADD siRNA knockdown or Cisplatin monotherapy, the additive effect of each monotherapy being 54% cell death (Additive: Cisplatin+MADD siRNA=0+54=54% cell death).

In another embodiment, 1.875 μM Cisplatin was added as monotherapy to PLC/PRF/5 hepatic cancer cells. Moreover, cells were transfected with MADD siRNA as monotherapy. In combination, 1.875 μM Cisplatin was added to cells transfected with MADD siRNA. The amount of cell death in the cell cultures of the treatment paradigm represented by untreated control cells, control cells transfected with Scrambled siRNA, cells transfected with MADD siRNA, cells treated with 1.875 μM Cisplatin, and cells transfected with MADD siRNA and treated with 1.875 μM Cisplatin, was evaluated at 24 hours post Cisplatin treatment (Table 47).

TABLE 47

| Treatment | Observed % Cell death | Net % cell death* |
|---|---|---|
| Control (untreated) | 0 | 0 |
| Scrambled siRNA (alone) | 5 | 5 − 5 = 0 |
| MADD siRNA (alone) | 25 | 25 − 5 = 20 |
| Cisplatin (alone) | 41 | 41 |
| Cisplatin + MADD siRNA | 91 | 91 − 5 = 86 |

*Net % cell death after accounting for Scrambled (non-specific siRNA).

The results, as reported in Table 47, demonstrate that siRNA knockdown of MADD resulted in 20% cell death, Cisplatin monotherapy at 1.875 μM concentration resulted in 41% cell death, and addition of 1.875 μM Cisplatin to cells transfected with MADD siRNA resulted in 86% cell death. All results accommodated for transfection effect utilizing Scramble siRNA cell death data. Taken together, the results demonstrate synergy of the combination of siRNA knockdown of MADD and Cisplatin treatment, resulting in 86% cell death which far exceeds the additive effect of monotherapy with either MADD siRNA knockdown or Cisplatin monotherapy, the additive effect of each monotherapy being 61% cell death (Additive: Cisplatin+MADD siRNA=41+20=61% cell death).

Considering the results of the foregoing experiments, the instant assay demonstrates that combination of alkylating agent chemotherapeutic treatment and MADD knock-down results in surprisingly synergistic effects on inducing cancer cell death. The results demonstrate that the combination alkylating agent chemotherapy and MADD knock down results in more than an additive effect on cell death. As a result, dosages of the alkylating agent chemotherapeutic may be lowered to a level which was previously considered to be non-therapeutic, thereby providing a cancer therapy which exhibits an unexpected margin of safety and reduction of unwanted side effects.

What is claimed is:

1. A combination of antineoplastic agents useful for treating cancer comprising (a) an effective amount of one or more nucleic acid molecules comprising GAUUGUCAUAGAUUCGCCGTT (SEQ ID NO:4) or GAUUGUCAUAGAUUCGCCG (SEQ ID NO:10), or a complementary sequence thereto, and (b) a subthreshold amount of one or more protein kinase inhibitor chemotherapeutic, one or more anthracycline chemotherapeutic, one or more nucleoside analog chemotherapeutic, one or more apoptosis-inducing molecular therapeutic, or one or more alkylating agent chemotherapeutic.

2. The combination of claim 1, wherein the one or more nucleic acid molecules are selected from siRNA, shRNA and antisense oligonucleotides.

3. The combination of claim 2, wherein the siRNA or shRNA comprises a nucleic acid having the sequence CGGCGAAUCUAUGACAAUC (SEQ ID NO:2).

4. The combination of claim 2, wherein the one or more nucleic acid molecules are comprised in a drug delivery system comprising a targeted liposome formulation or a lentivirus vector.

5. The combination of claim 1, wherein the one or more protein kinase inhibitor chemotherapeutic is selected from Imatinib, trastuzumab, bevacizumab, gefitinib, cetuximab, Sorafenib, toceranib, erlotinib, lapatinib, sunitinib, nilotinib, bosutinib, neratinib and vatalanib.

6. The combination of claim 1, wherein the one or more anthracycline chemotherapeutic is selected from daunorubicin, doxorubicin, epirubicin, idarubicin and valrubicin.

7. The combination of claim 1, wherein the one or more nucleoside analog chemotherapeutic is selected from Gemcitabine, 5-Fluorouracil and Cytarabine.

8. The combination of claim 1, wherein the one or more apoptosis-inducing molecular therapeutic is selected from Interleukin 2 (IL2), Interferon-α (IFN-α) and Tumor necrosis factor α-related apoptosis-inducing ligand (TRAIL).

9. The combination of claim 1, wherein the one or more alkylating agent chemotherapeutic is selected from cyclophosphamide, mechlorethane, cisplatin, carboplatin, procarbazine, ifosfamide, melphalan, chlorambucil, cyclophosphamide, streptozocin, carmustine, lomustine, busulfan, and dacarbazine.

10. A method of treating cancer in a subject in need thereof, comprising administering an effective amount of a combination of antineoplastic agents comprising an effective amount of one or more nucleic acid molecules comprising GAUUGUCAUAGAUUCGCCGTT (SEQ ID NO:4) or GAUUGUCAUAGAUUCGCCG (SEQ ID NO:10), or a complementary sequence thereto, and a subthreshold amount of:

(a) one or more protein kinase inhibitor chemotherapeutic when the cancer is chronic myeloid leukemia, breast cancer, lung cancer, colorectal cancer, primary kidney cancer, liver cancer or thyroid cancer, or other type of solid tumor cancer as well as Kaposi's sarcoma;

(b) one or more anthracycline chemotherapeutic when the cancer is leukemia, lymphoma, breast cancer, stomach cancer, uterine cancer, pancreatic cancer, ovarian cancer, cervical cancer, prostate cancer, melanoma, esophageal cancer, bladder cancer, liver cancer, thyroid tumor, or lung cancer, or other type of solid tumor cancer as well as Kaposi's sarcoma;

(c) one or more nucleoside analog chemotherapeutic when the cancer is breast cancer, non-small cell lung cancer, pancreatic cancer, bladder cancer, biliary tract cancer and colon cancer, esophageal cancer, stomach cancer, pancreatic cancer, breast cancer, cervical cancer, or other type of solid tumor cancer;

(d) one or more apoptosis-inducing molecular therapeutic when the cancer is circulatory cancers such as leukemia and lymphoma, melanoma, bladder and kidney cancers, or other type of solid tumor cancer; or (e) one or more alkylating agent chemotherapeutic when the cancer is slow growing solid tumors and leukemia, lung cancer, ovarian cancer, breast cancer, lymphomas, sarcomas, myelomas, Hodgkin's disease, topical treatment for skin lesions of mycosis fungoides (cutaneous T-cell lymphoma), both Hodgkin's and non-Hodgkin's lymphoma, testicular cancer, germ cell tumors, bladder cancer, head and neck cancer, cervical cancer, multiple myeloma, neuroblastoma, rhabdomyosarcoma, lymphocytic leukemia, malignant lymphomas including lymphosarcoma, giant follicular lymphoma, Burkitt's lymphoma, chronic lymphocytic leukemia, chronic myelocytic leukemia, acute myelocytic leukemia, acute lymphocytic leukemia, t-cell lymphoma, multiple myeloma, retinoblastoma, Ewing's sarcoma, endometrial cancer, islet cell pancreatic cancer, brain tumors, glioblastoma, brainstem glioma, medulloblastoma, astrocytoma, ependymoma, and metastatic brain tumors, colon cancer, fibrosarcomas, anaplastic astrocytoma, or glioblastoma multiforme.

11. The method of claim 10, wherein the one or more nucleic acid molecules are selected from siRNA, shRNA and antisense oligonucleotides.

12. The method of claim 11, wherein the siRNA and shRNA comprise a nucleic acid having the sequence CGGCGAAUCUAUGACAAUC (SEQ ID NO:2).

13. The method of claim 11, wherein the one or more siRNA, shRNA and antisense oligonucleotides are administered in the form of a liposomal formulation or by lentivirus transfection.

14. The method of claim 10, wherein the one or more protein kinase inhibitor chemotherapeutic is selected from Imatinib, trastuzumab, bevacizumab, gefitinib, cetuximab, Sorafenib, toceranib, erlotinib, lapatinib, sunitinib, nilotinib, bosutinib, neratinib and vatalanib.

15. The method of claim 10, wherein the one or more anthracycline chemotherapeutic is selected from daunorubicin, doxorubicin, epirubicin, idarubicin and valrubicin.

16. The method of claim 10, wherein the one or more nucleoside analog chemotherapeutic is selected from Gemcitabine, 5-Fluorouracil and Cytarabine.

17. The method of claim 10, wherein the one or more apoptosis-inducing molecular therapeutic is selected from Interleukin 2 (IL2), Interferon-α (IFN-α) and Tumor necrosis factor α-related apoptosis-inducing ligand (TRAIL).

18. The method of claim 10, wherein the one or more alkylating agent chemotherapeutic is selected from cyclophosphamide, mechlorethane, cisplatin, carboplatin, procarbazine, Ifosfamide, melphalan, chlorambucil, cyclophosphamide, streptozocin, carmustine, lomustine, busulfan, and dacarbazine.

* * * * *

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1

cggcgaatct atgacaatc                                          19


<210> SEQ ID NO 2
<211> LENGTH: 19
<212> TYPE: RNA
<213> ORGANISM: Artificial sequence
<220> FEATURE:
<223> OTHER INFORMATION: Synthetic oligonucleotide
```

<400> SEQUENCE: 2
cggcgaaucu augacaauc 19

<210> SEQ ID NO 3
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 3
cgaatctatg acaatcttca agagagattg tcatagattc gccg 44

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
gauugucaua gauucgccgt t 21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
uugcuaagcg ucggucaaut t 21

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
agccccaata tggctttccc 20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ctgatccact aacgccctcc 20

<210> SEQ ID NO 8
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 8
atctggcacc acaccttcta caatgagctg cg 32

```
<210> SEQ ID NO 9
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 9

cgtcatactc ctgcttgctg atccacatct gc                                 32


<210> SEQ ID NO 10
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 10

gauugucaua gauucgccg                                                19


<210> SEQ ID NO 11
<211> LENGTH: 6006
<212> TYPE: DNA
<213> ORGANISM: Homo sapiens

<400> SEQUENCE: 11

ggatttcagc gctaaggcgt cggcggtgca cctcacgtgc atgtgtagca tgccttggtt     60

tttcctttgg catctgaaaa aggcacaacc tgaaagacct agaacccagt gtcggtcccc    120

aggccctttg ggacaggaag agaagagccg tgtggccgcg gggaggatgt cctgaggcgg    180

ggctgtcctc gcggactgac tggactccat ctcccagcgg gcgccgcggc gcggccacgc    240

ccccccactc cccgcgcgcg cccggtggag acttcgattt tcagaattcc tcctgggaat    300

gctgactcct tgcttggtgc cctgatgctt ctctgagata aactgatgaa ttggaaccat    360

ggtgcaaaag aagaagttct gtcctcggtt acttgactat ctagtgatcg taggggccag    420

gcacccgagc agtgatagcg tggcccagac tcctgaattg ctacggcgat accccttgga    480

ggatcacact gagtttcccc tgcccccaga tgtagtgttc ttctgccagc ccgagggctg    540

cctgagcgtg cggcagcggc gcatgagcct tcgggatgat acctcttttg tcttcaccct    600

cactgacaag gacactggag tcacgcgata tggcatctgt gttaacttct accgctcctt    660

ccaaaagcga atctctaagg agaaggggga aggtggggca gggtcccgtg ggaaggaagg    720

aacccatgcc acctgtgcct cagaagaggg tggcactgag agctcagaga gtggctcatc    780

cctgcagcct ctcagtgctg actctacccc tgatgtgaac cagtctcctc ggggcaaacg    840

ccgggccaag gcggggagcc gctcccgcaa cagtactctc acgtccctgt gcgtgctcag    900

ccactaccct ttcttctcca ccttccgaga gtgtttgtat actctcaagc gcctggtgga    960

ctgctgtagt gagcgccttc tgggcaagaa actgggcatc cctcgaggcg tacaaaggga   1020

caccatgtgg cggatcttta ctggatcgct gctggtagag gagaagtcaa gtgcccttct   1080

gcatgacctt cgagagattg aggcctggat ctatcgattg ctgcgctccc cagtacccgt   1140

ctctgggcag aagcgagtag acatcgaggt cctaccccaa gagctccagc cagctctgac   1200

ctttgctctt ccagacccat ctcgattcac cctagtggat ttcccactgc accttccctt   1260

ggaacttcta ggtgtggacg cctgtctcca ggtgctaacc tgcattctgt tagagcacaa   1320

ggtggtgcta cagtcccgag actacaatgc actctccatg tctgtgatgg cattcgtggc   1380

aatgatctac ccactggagt atatgtttcc tgtcatcccg ctgctaccca cctgcatggc   1440
```

-continued

```
atcagcagag cagctgctgt tggctccaac cccgtacatc attggggttc ctgccagctt   1500
cttcctctac aaactggact tcaaaatgcc tgatgatgta tggctagtgg atctggacag   1560
caatagggtg attgccccca ccaatgcaga agtgctgcct atcctgccag aaccagaatc   1620
actagagctg aaaaagcatt taaagcaggc cttggccagc atgagtctca acacccagcc   1680
catcctcaat ctggagaaat ttcatgaggg ccaggagatc cccctctct tgggaaggcc    1740
ttctaatgac ctgcagtcca caccgtccac tgaattcaac ccactcatct atggcaatga   1800
tgtggattct gtggatgttg caaccagggt tgccatggta cggttcttca attccgccaa   1860
cgtgctgcag ggatttcaga tgcacacgcg taccctgcgc ctctttcctc ggcctgtggt   1920
agcttttcaa gctggctcct ttctagcctc acgtccccgg cagactcctt ttgccgagaa   1980
attggccagg actcaggctg tggagtactt tggggaatgg atccttaacc ccaccaacta   2040
tgcctttcag cgaattcaca acaatatgtt tgatccagcc ctgattggtg acaagccaaa   2100
gtggtatgct catcagctgc agcctatcca ctatcgcgtc tatgacagca attcccagct   2160
ggctgaggcc ctgagtgtac caccagagcg ggactctgac tccgaaccta ctgatgatag   2220
tggcagtgat agtatggatt atgacgattc aagctcttct tactcctccc ttggtgactt   2280
tgtcagtgaa atgatgaaat gtgacattaa tggtgatact cccaatgtgg accctctgac   2340
acatgcagca ctgggggatg ccagcgaggt ggagattgac gagctgcaga atcagaagga   2400
agcagaagag cctggcccag acagtgagaa ctctcaggaa aaccccccac tgcgctccag   2460
ctctagcacc acagccagca gcagccccag cactgtcatc cacggagcca actctgaacc   2520
tgctgactct acggagatgg atgataaggc agcagtaggc gtctccaagc cctcccttc    2580
cgtgcctccc agcattggca aatcgaacgt ggacagacgt caggcagaaa ttggagaggg   2640
gtcagtgcgc cggcgaatct atgacaatcc atacttcgag ccccaatatg gctttccccc   2700
tgaggaagat gaggatgagc aggggaaag ttacactccc cgattcagcc aacatgtcag    2760
tggcaatcgg gctcaaaagc tgctgcggcc caacagcttg agactggcaa gtgactcaga   2820
tgcagagtca gactctcggg caagctctcc caactccacc gtctccaaca ccagcaccga   2880
gggcttcggg ggcatcatgt cttttgccag cagcctctat cggaaccaca gtaccagctt   2940
cagtctttca aacctcacac tgcccaccaa aggtgcccga gagaaggcca cgcccttccc   3000
cagtctgaaa ggaaacagga gggcgttagt ggatcagaag tcatctgtca ttaaacacag   3060
cccaacagtg aaaagagaac ctccatcacc ccagggtcga tccagcaatt ctagtgagaa   3120
ccagcagttc ctgaaggagg tggtgcacag cgtgctggac ggccagggag ttggctggct   3180
caacatgaaa aaggtgcgcc ggctgctgga gagcgagcag ctgcgagtct ttgtcctgag   3240
caagctgaac cgcatggtgc agtcagagga cgatgcccgg caggacatca tcccggatgt   3300
ggagatcagt cggaaggtgt acaagggaat gttagacctc ctcaagtgta cagtcctcag   3360
cttggagcag tcctatgccc acgcgggtct gggtggcatg gccagcatct ttgggctttt   3420
ggagattgcc cagacccact actatagtaa agaaccagac aagcggaaga gaagtccaac   3480
agaaagtgta aataccccag ttggcaagga tcctggccta gctgggcggg gggacccaaa   3540
ggctatggca caactgagag ttccacaact gggacctcgg gcaccaagtg ccacaggaaa   3600
gggtcctaag gaactggaca ccagaagttt aaaggaagaa aattttatag catctattgg   3660
gcctgaagta atcaaacctg tctttgacct tggtgagaca gaggagaaaa agtcccagat   3720
cagcgcagac agtggtgtga gcctgacgtc tagttcccag aggactgatc aagactctgt   3780
catcggcgtg agtccagctg ttatgatccg cagctcaagt caggattctg aagttagcac   3840
```

```
cgtggtgagt aatagctctg gagagaccct tggagctgac agtgacttga gcagcaatgc   3900

aggtgatgga ccaggtggcg agggcagtgt tcacctggca agctctcggg gcactttgtc   3960

tgatagtgaa attgagacca actctgccac aagcaccatc tttggtaaag cccacagctt   4020

gaagccaagc ataaaggaga agctggcagg cagccccatt cgtacttctg aagatgtgag   4080

ccagcgagtc tatctctatg agggactcct aggcaaagag cgttctactt tatgggacca   4140

aatgcaattc tgggaagatg ccttcttaga tgctgtgatg ttggagagag aagggatggg   4200

tatggaccag ggtccccagg aaatgatcga caggtacctg tcccttggag aacatgaccg   4260

gaagcgcctg gaagatgatg aagatcgctt gttggccaca cttctgcaca acctcatctc   4320

ctacatgctg ctgatgaagg taaataagaa tgacatccgc aagaaggtga ggcgcctaat   4380

gggaaagtcg cacattgggc ttgtgtacag ccagcaaatc aatgaggtgc ttgatcagct   4440

ggcgaacctg aatggacgcg atctctctat ctggtccagt ggcagccggc acatgaagaa   4500

gcagacattt gtggtacatg cagggacaga tacaaacgga gatatctttt tcatggaggt   4560

gtgcgatgac tgtgtggtgt tgcgtagtaa catcggaaca gtgtatgagc gctggtggta   4620

cgagaagctc atcaacatga cctactgtcc caagacgaag gtgttgtgct tgtggcgtag   4680

aaatggctct gagacccagc tcaacaagtt ctatactaaa aagtgtcggg agctgtacta   4740

ctgtgtgaag gacagcatgg agcgcgctgc cgcccgacag caaagcatca aacccggacc   4800

tgaattgggt ggcgagttcc ctgtgcagga cctgaagact ggtgagggtg gcctgctgca   4860

ggtgaccctg gaagggatca acctcaaatt catgcacaat caggttttca tagagctgaa   4920

tcacattaaa aagtgcaata cagttcgagg cgtctttgtc ctggaggaat ttgttcctga   4980

aattaaagaa gtggtgagcc acaagtacaa gacaccaatg gcccacgaaa tctgctactc   5040

cgtattatgt ctcttctcgt acgtggctgc agttcatagc agtgaggaag atctcagaac   5100

cccgccccgg cctgtctcta gctgatggag aggggctacg cagctgcccc agcccagggc   5160

acgcccctgg ccccttgctg ttcccaagtg cacgatgctg ctgtgactga ggagtggatg   5220

atgctcgtgt gtcctctgca agccccctgc tgtggcttgg ttggttaccg gttatgtgtc   5280

cctctgagtg tgtcttgagc gtgtccacct tctccctctc cactcccaga agaccaaact   5340

gccttcccct cagggctcaa gaatgtgtac agtctgtggg gccggtgtga acccactatt   5400

ttgtgtcctt gagacatttg tgttgtggtt ccttgtcctt gtccctggcg ttataactgt   5460

ccactgcaag agtctggctc tcccttctct gtgacccggc atgactgggc gcctggagca   5520

gtttcactct gtgaggagtg agggaaccct ggggctcacc ctctcagagg aagggcacag   5580

agaggaaggg aagaattggg gggcagccgg agtgagtggc agcctccctg cttccttctg   5640

cattcccaag ccggcagcta ctgcccaggg cccgcagtgt tggctgctgc ctgccacagc   5700

ctctgtgact gcagtggagc ggcgaattcc ctgtggcctg ccatgccttc ggcatcagag   5760

gatggagtgg tcgaggctag tggagtccca gggaccgctg gctgctctgc ctgagcatca   5820

gggagggggc aggaaagacc aagctgggtt tgcacatctg tctgcaggct gtctctccag   5880

gcacggggtg tcaggaggga gagacagcct gggtatgggc aagaaatgac tgtaaatatt   5940

tcagccccac attatttata gaaaatgtac agttgtgtga atgtgaaata aatgtcctca   6000

actccc                                                              6006
```

<210> SEQ ID NO 12
<211> LENGTH: 1588
<212> TYPE: PRT
<213> ORGANISM: Homo sapiens

<400> SEQUENCE: 12

```
Met Val Gln Lys Lys Lys Phe Cys Pro Arg Leu Leu Asp Tyr Leu Val
1               5                   10                  15

Ile Val Gly Ala Arg His Pro Ser Ser Asp Ser Val Ala Gln Thr Pro
            20                  25                  30

Glu Leu Leu Arg Arg Tyr Pro Leu Glu Asp His Thr Glu Phe Pro Leu
        35                  40                  45

Pro Pro Asp Val Val Phe Phe Cys Gln Pro Glu Gly Cys Leu Ser Val
    50                  55                  60

Arg Gln Arg Arg Met Ser Leu Arg Asp Asp Thr Ser Phe Val Phe Thr
65                  70                  75                  80

Leu Thr Asp Lys Asp Thr Gly Val Thr Arg Tyr Gly Ile Cys Val Asn
                85                  90                  95

Phe Tyr Arg Ser Phe Gln Lys Arg Ile Ser Lys Glu Lys Gly Glu Gly
            100                 105                 110

Gly Ala Gly Ser Arg Gly Lys Glu Gly Thr His Ala Thr Cys Ala Ser
        115                 120                 125

Glu Glu Gly Gly Thr Glu Ser Ser Glu Ser Gly Ser Ser Leu Gln Pro
    130                 135                 140

Leu Ser Ala Asp Ser Thr Pro Asp Val Asn Gln Ser Pro Arg Gly Lys
145                 150                 155                 160

Arg Arg Ala Lys Ala Gly Ser Arg Ser Arg Asn Ser Thr Leu Thr Ser
                165                 170                 175

Leu Cys Val Leu Ser His Tyr Pro Phe Phe Ser Thr Phe Arg Glu Cys
            180                 185                 190

Leu Tyr Thr Leu Lys Arg Leu Val Asp Cys Cys Ser Glu Arg Leu Leu
        195                 200                 205

Gly Lys Lys Leu Gly Ile Pro Arg Gly Val Gln Arg Asp Thr Met Trp
    210                 215                 220

Arg Ile Phe Thr Gly Ser Leu Leu Val Glu Glu Lys Ser Ser Ala Leu
225                 230                 235                 240

Leu His Asp Leu Arg Glu Ile Glu Ala Trp Ile Tyr Arg Leu Leu Arg
                245                 250                 255

Ser Pro Val Pro Val Ser Gly Gln Lys Arg Val Asp Ile Glu Val Leu
            260                 265                 270

Pro Gln Glu Leu Gln Pro Ala Leu Thr Phe Ala Leu Pro Asp Pro Ser
        275                 280                 285

Arg Phe Thr Leu Val Asp Phe Pro Leu His Leu Pro Leu Glu Leu Leu
    290                 295                 300

Gly Val Asp Ala Cys Leu Gln Val Leu Thr Cys Ile Leu Leu Glu His
305                 310                 315                 320

Lys Val Val Leu Gln Ser Arg Asp Tyr Asn Ala Leu Ser Met Ser Val
                325                 330                 335

Met Ala Phe Val Ala Met Ile Tyr Pro Leu Glu Tyr Met Phe Pro Val
            340                 345                 350

Ile Pro Leu Leu Pro Thr Cys Met Ala Ser Ala Glu Gln Leu Leu Leu
        355                 360                 365

Ala Pro Thr Pro Tyr Ile Ile Gly Val Pro Ala Ser Phe Phe Leu Tyr
    370                 375                 380

Lys Leu Asp Phe Lys Met Pro Asp Asp Val Trp Leu Val Asp Leu Asp
385                 390                 395                 400

Ser Asn Arg Val Ile Ala Pro Thr Asn Ala Glu Val Leu Pro Ile Leu
                405                 410                 415
```

-continued

```
Pro Glu Pro Glu Ser Leu Glu Leu Lys Lys His Leu Lys Gln Ala Leu
            420                 425                 430

Ala Ser Met Ser Leu Asn Thr Gln Pro Ile Leu Asn Leu Glu Lys Phe
        435                 440                 445

His Glu Gly Gln Glu Ile Pro Leu Leu Leu Gly Arg Pro Ser Asn Asp
    450                 455                 460

Leu Gln Ser Thr Pro Ser Thr Glu Phe Asn Pro Leu Ile Tyr Gly Asn
465                 470                 475                 480

Asp Val Asp Ser Val Asp Val Ala Thr Arg Val Ala Met Val Arg Phe
                485                 490                 495

Phe Asn Ser Ala Asn Val Leu Gln Gly Phe Gln Met His Thr Arg Thr
            500                 505                 510

Leu Arg Leu Phe Pro Arg Pro Val Val Ala Phe Gln Ala Gly Ser Phe
        515                 520                 525

Leu Ala Ser Arg Pro Arg Gln Thr Pro Phe Ala Glu Lys Leu Ala Arg
    530                 535                 540

Thr Gln Ala Val Glu Tyr Phe Gly Glu Trp Ile Leu Asn Pro Thr Asn
545                 550                 555                 560

Tyr Ala Phe Gln Arg Ile His Asn Asn Met Phe Asp Pro Ala Leu Ile
                565                 570                 575

Gly Asp Lys Pro Lys Trp Tyr Ala His Gln Leu Gln Pro Ile His Tyr
            580                 585                 590

Arg Val Tyr Asp Ser Asn Ser Gln Leu Ala Glu Ala Leu Ser Val Pro
        595                 600                 605

Pro Glu Arg Asp Ser Asp Ser Glu Pro Thr Asp Asp Ser Gly Ser Asp
    610                 615                 620

Ser Met Asp Tyr Asp Asp Ser Ser Ser Ser Tyr Ser Ser Leu Gly Asp
625                 630                 635                 640

Phe Val Ser Glu Met Met Lys Cys Asp Ile Asn Gly Asp Thr Pro Asn
                645                 650                 655

Val Asp Pro Leu Thr His Ala Ala Leu Gly Asp Ala Ser Glu Val Glu
            660                 665                 670

Ile Asp Glu Leu Gln Asn Gln Lys Glu Ala Glu Glu Pro Gly Pro Asp
        675                 680                 685

Ser Glu Asn Ser Gln Glu Asn Pro Pro Leu Arg Ser Ser Ser Ser Thr
    690                 695                 700

Thr Ala Ser Ser Ser Pro Ser Thr Val Ile His Gly Ala Asn Ser Glu
705                 710                 715                 720

Pro Ala Asp Ser Thr Glu Met Asp Asp Lys Ala Ala Val Gly Val Ser
                725                 730                 735

Lys Pro Leu Pro Ser Val Pro Pro Ser Ile Gly Lys Ser Asn Val Asp
            740                 745                 750

Arg Arg Gln Ala Glu Ile Gly Glu Gly Ser Val Arg Arg Arg Ile Tyr
        755                 760                 765

Asp Asn Pro Tyr Phe Glu Pro Gln Tyr Gly Phe Pro Pro Glu Glu Asp
    770                 775                 780

Glu Asp Glu Gln Gly Glu Ser Tyr Thr Pro Arg Phe Ser Gln His Val
785                 790                 795                 800

Ser Gly Asn Arg Ala Gln Lys Leu Leu Arg Pro Asn Ser Leu Arg Leu
                805                 810                 815

Ala Ser Asp Ser Asp Ala Glu Ser Asp Ser Arg Ala Ser Ser Pro Asn
            820                 825                 830
```

-continued

```
Ser Thr Val Ser Asn Thr Ser Thr Glu Gly Phe Gly Gly Ile Met Ser
        835                 840                 845

Phe Ala Ser Ser Leu Tyr Arg Asn His Ser Thr Ser Phe Ser Leu Ser
    850                 855                 860

Asn Leu Thr Leu Pro Thr Lys Gly Ala Arg Glu Lys Ala Thr Pro Phe
865                 870                 875                 880

Pro Ser Leu Lys Gly Asn Arg Arg Ala Leu Val Asp Gln Lys Ser Ser
                885                 890                 895

Val Ile Lys His Ser Pro Thr Val Lys Arg Glu Pro Pro Ser Pro Gln
            900                 905                 910

Gly Arg Ser Ser Asn Ser Ser Glu Asn Gln Gln Phe Leu Lys Glu Val
        915                 920                 925

Val His Ser Val Leu Asp Gly Gln Gly Val Gly Trp Leu Asn Met Lys
    930                 935                 940

Lys Val Arg Arg Leu Leu Glu Ser Glu Gln Leu Arg Val Phe Val Leu
945                 950                 955                 960

Ser Lys Leu Asn Arg Met Val Gln Ser Glu Asp Asp Ala Arg Gln Asp
                965                 970                 975

Ile Ile Pro Asp Val Glu Ile Ser Arg Lys Val Tyr Lys Gly Met Leu
            980                 985                 990

Asp Leu Leu Lys Cys Thr Val Leu  Ser Leu Glu Gln Ser  Tyr Ala His
        995                 1000                1005

Ala Gly  Leu Gly Gly Met Ala  Ser Ile Phe Gly Leu  Leu Glu Ile
    1010                1015                1020

Ala Gln  Thr His Tyr Tyr Ser  Lys Glu Pro Asp Lys  Arg Lys Arg
    1025                1030                1035

Ser Pro  Thr Glu Ser Val Asn  Thr Pro Val Gly Lys  Asp Pro Gly
    1040                1045                1050

Leu Ala  Gly Arg Gly Asp Pro  Lys Ala Met Ala Gln  Leu Arg Val
    1055                1060                1065

Pro Gln  Leu Gly Pro Arg Ala  Pro Ser Ala Thr Gly  Lys Gly Pro
    1070                1075                1080

Lys Glu  Leu Asp Thr Arg Ser  Leu Lys Glu Glu Asn  Phe Ile Ala
    1085                1090                1095

Ser Ile  Gly Pro Glu Val Ile  Lys Pro Val Phe Asp  Leu Gly Glu
    1100                1105                1110

Thr Glu  Glu Lys Lys Ser Gln  Ile Ser Ala Asp Ser  Gly Val Ser
    1115                1120                1125

Leu Thr  Ser Ser Ser Gln Arg  Thr Asp Gln Asp Ser  Val Ile Gly
    1130                1135                1140

Val Ser  Pro Ala Val Met Ile  Arg Ser Ser Ser Gln  Asp Ser Glu
    1145                1150                1155

Val Ser  Thr Val Val Ser Asn  Ser Ser Gly Glu Thr  Leu Gly Ala
    1160                1165                1170

Asp Ser  Asp Leu Ser Ser Asn  Ala Gly Asp Gly Pro  Gly Gly Glu
    1175                1180                1185

Gly Ser  Val His Leu Ala Ser  Ser Arg Gly Thr Leu  Ser Asp Ser
    1190                1195                1200

Glu Ile  Glu Thr Asn Ser Ala  Thr Ser Thr Ile Phe  Gly Lys Ala
    1205                1210                1215

His Ser  Leu Lys Pro Ser Ile  Lys Glu Lys Leu Ala  Gly Ser Pro
    1220                1225                1230
```

```
Ile Arg  Thr Ser Glu Asp Val  Ser Gln Arg Val Tyr  Leu Tyr Glu
    1235                 1240                 1245

Gly Leu  Leu Gly Lys Glu Arg  Ser Thr Leu Trp Asp  Gln Met Gln
    1250                 1255                 1260

Phe Trp  Glu Asp Ala Phe Leu  Asp Ala Val Met Leu  Glu Arg Glu
    1265                 1270                 1275

Gly Met  Gly Met Asp Gln Gly  Pro Gln Glu Met Ile  Asp Arg Tyr
    1280                 1285                 1290

Leu Ser  Leu Gly Glu His Asp  Arg Lys Arg Leu Glu  Asp Asp Glu
    1295                 1300                 1305

Asp Arg  Leu Leu Ala Thr Leu  Leu His Asn Leu Ile  Ser Tyr Met
    1310                 1315                 1320

Leu Leu  Met Lys Val Asn Lys  Asn Asp Ile Arg Lys  Lys Val Arg
    1325                 1330                 1335

Arg Leu  Met Gly Lys Ser His  Ile Gly Leu Val Tyr  Ser Gln Gln
    1340                 1345                 1350

Ile Asn  Glu Val Leu Asp Gln  Leu Ala Asn Leu Asn  Gly Arg Asp
    1355                 1360                 1365

Leu Ser  Ile Trp Ser Ser Gly  Ser Arg His Met Lys  Lys Gln Thr
    1370                 1375                 1380

Phe Val  Val His Ala Gly Thr  Asp Thr Asn Gly Asp  Ile Phe Phe
    1385                 1390                 1395

Met Glu  Val Cys Asp Asp Cys  Val Val Leu Arg Ser  Asn Ile Gly
    1400                 1405                 1410

Thr Val  Tyr Glu Arg Trp Trp  Tyr Glu Lys Leu Ile  Asn Met Thr
    1415                 1420                 1425

Tyr Cys  Pro Lys Thr Lys Val  Leu Cys Leu Trp Arg  Arg Asn Gly
    1430                 1435                 1440

Ser Glu  Thr Gln Leu Asn Lys  Phe Tyr Thr Lys Lys  Cys Arg Glu
    1445                 1450                 1455

Leu Tyr  Tyr Cys Val Lys Asp  Ser Met Glu Arg Ala  Ala Ala Arg
    1460                 1465                 1470

Gln Gln  Ser Ile Lys Pro Gly  Pro Glu Leu Gly Gly  Glu Phe Pro
    1475                 1480                 1485

Val Gln  Asp Leu Lys Thr Gly  Glu Gly Gly Leu Leu  Gln Val Thr
    1490                 1495                 1500

Leu Glu  Gly Ile Asn Leu Lys  Phe Met His Asn Gln  Val Phe Ile
    1505                 1510                 1515

Glu Leu  Asn His Ile Lys Lys  Cys Asn Thr Val Arg  Gly Val Phe
    1520                 1525                 1530

Val Leu  Glu Glu Phe Val Pro  Glu Ile Lys Glu Val  Val Ser His
    1535                 1540                 1545

Lys Tyr  Lys Thr Pro Met Ala  His Glu Ile Cys Tyr  Ser Val Leu
    1550                 1555                 1560

Cys Leu  Phe Ser Tyr Val Ala  Ala Val His Ser Ser  Glu Glu Asp
    1565                 1570                 1575

Leu Arg  Thr Pro Pro Arg Pro  Val Ser Ser
    1580                 1585
```

<210> SEQ ID NO 13
<211> LENGTH: 47
<212> TYPE: DNA
<213> ORGANISM: Artificial sequence
<220> FEATURE:
<223> OTHER INFORMATION: Synthetic oligonucleotide -continued

```
<400> SEQUENCE: 13

cggcgaatct atgacaatct tcaagagaga ttgtcataga ttcgccg                47


<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 14

gtaccagctt cagtctttc                                               19
```